US007855205B2

(12) United States Patent
Huang et al.

(10) Patent No.: US 7,855,205 B2
(45) Date of Patent: Dec. 21, 2010

(54) PYRIMIDINYL SUBSTITUTED FUSED-PYRROLYL COMPOUNDS USEFUL IN TREATING KINASE DISORDERS

(75) Inventors: Shenlin Huang, Raritan, NJ (US); Ronghua Li, Bridgewater, NJ (US); Peter J. Connolly, New Providence, NJ (US); Stuart L. Emanuel, Doylestown, PA (US); Steven A. Middleton, Flemington, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 795 days.

(21) Appl. No.: 11/260,986

(22) Filed: Oct. 28, 2005

(65) Prior Publication Data

US 2006/0183900 A1 Aug. 17, 2006

Related U.S. Application Data

(60) Provisional application No. 60/623,654, filed on Oct. 29, 2004.

(51) Int. Cl.
*C07D 403/04* (2006.01)
*A61K 31/407* (2006.01)

(52) U.S. Cl. ............................ 514/235.8; 514/253.04; 514/275; 544/122; 544/295; 544/331

(58) Field of Classification Search ................. 544/122, 544/295, 331; 514/235.8, 253.04, 275
See application file for complete search history.

(56) References Cited

U.S. PATENT DOCUMENTS

| 2004/0097506 | A1 | 5/2004 | Thomas |
| 2005/0107384 | A1 | 5/2005 | Angibaud et al. |
| 2007/0043048 | A1* | 2/2007 | Bollbuck et al. ............ 514/241 |

FOREIGN PATENT DOCUMENTS

| WO | WO 0114375 A1 | 3/2001 |
| WO | WO 02079193 A1 | 10/2002 |
| WO | WO 02102783 A1 | 12/2002 |
| WO | WO 03011836 A1 | 2/2003 |
| WO | WO 03011837 A1 | 2/2003 |
| WO | WO 03051886 A1 | 6/2003 |
| WO | WO 03/092686 | 11/2003 |
| WO | WO 2004005282 A1 | 1/2004 |
| WO | WO 2004005283 A1 | 1/2004 |
| WO | WO 2005/095400 | * 10/2005 |

OTHER PUBLICATIONS

Bollbuck et al., CAPLUS Abstract 141:379931, 2004.*
Traxler, Protein Kinase inhibitors in cancer treatment, Expert Opinion on Therapeutic Patents, 7(6), pp. 571-588, 1997.*
Lu Valle et al., Cell Cycle Control in Growth Plate Chondrocytes, Frontiers in Biosciences 5, d493-503, May 2000.*
Blain et al., Differential Interaction of the Cyclin-dependent Kinase (Cdk) Inhibitor p27Kip1 with Cyclin A-Cdk2 and Cyclin D2-Cdk4, The Journal of Biological Chemistry, vol. 272, No. 41, pp. 25863-25872, Oct. 1997.*
Simone, Oncology: Introduction, Cecil Textbook of Medicine, 20th Edition, vol. 1, pp. 1004-1010, 1996.*
Damasio, Alzheimer's Disease and Related Dementias, Cecil Textbook of Medicine, 20th Edition, vol. 2, pp. 1992-1996, 1996.*
Doublas, Jr., Introduction to Viral Diseases, Cecil Textbook of Medicine, 20th Edition, vol. 2, pp. 1739-1747, 1996.*
Layzer, Degenerative Diseases of the Nervous System, Cecil Textbook of Medicine, 20th Edition, vol. 2, pp. 2050-2057, 1996.*
International Search Report re: PCT/US05/38905 dated Apr. 13, 2006.
X. Wang, et al., "Epidermal Growth Factor Receptor is A Cellular Receptor for Human Cytomegalovirus," *Nature*, Jul. 24, 2003, vol. 424.
K. Nasmyth, "Viewpoint: Putting The Cell Cycle in Order," *Science*, vol. 274 (1996) p. 1643-1677.
D. O. Morgan, "Cyclin-Dependent Kinases: Engines, Clocks, and Microprocessors," *Annu.Rev Cell Dev. Biol.*, vol. 13 13 (1997), p. 261-291.
J. Lukas, et al., "Cyclin E-induced S Phase Without Activation of The pRb/E2F Pathway," *Genes and Dav.*, vol. 11 (1997), p. 1479-1492.
J.W. Harper, "Cyclin Dependent Kinase Inhibitors," *Cancer Surv.*, vol. 29 (1997), p. 91-107.
M. Hall, et al., "Genetic Alerations of Cyclins, Cyclin-Dependent Kinases, and Cdk Inhibitors in Human Cancer," *Adv. Cancer Res.*, vol. 68 (1996), p. 67-108.
A. Kamb, et al., "A Cell Cycle Regulator Potentially Involved in Genesis of Many Tumor Types," *Science*, vol. 264 (1994), p. 436-440.

(Continued)

*Primary Examiner*—Deepak Rao

(57) ABSTRACT

The present invention provides pyrimidinyl substituted fused-pyrrolyl compounds of Formula (I)

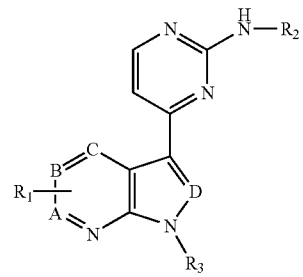

and pharmaceutical compositions comprising the compounds and methods of synthesis and use thereof. The compounds are kinase inhibitors useful in treating or ameliorating a kinase mediated, angiogenesis-mediated or hyperproliferative disorder. The invention thus also provides a therapeutic or prophylactic method of use for the compounds and/or pharmaceutical compositions to treat such disorders.

88 Claims, No Drawings

OTHER PUBLICATIONS

G. Delsal, et al., "Cell Cycle and Cancer: Critical Events at The G1 Restriction Point," *Critical Rev. Oncogenesis*, vol. 71 (1996), p. 127-142.

R. Ross, "The Pathogenesis of Atherosclerosis: A Perspective for The 1990's," *Nature*, 1993, 362, p. 801-809.

G. L. Wei, et al., "Temporally and Spatially Coordinated Expression of Cell Cycle Regulatory Factors after Angioplasty," *Circ. Res.*, (1997), 80, p. 418-426.

E. E. Brooks, "CVT-313, A Specific and Potent Inhibitor of CDK2 That Prevents Neointimal Proliferation," *J. Biol. Chem.*, (1997), 272(46): p. 29207-29211.

* cited by examiner

PYRIMIDINYL SUBSTITUTED FUSED-PYRROLYL COMPOUNDS USEFUL IN TREATING KINASE DISORDERS

CROSS REFERENCE TO RELATED APPLICATIONS

This present application claims benefit of U.S. Provisional Patent Application Ser. No. 60/623,654, filed Oct. 29, 2004, which is incorporated herein by reference in its entirety and for all purposes.

FIELD OF THE INVENTION

The present invention relates to a series of pyrimidinyl substituted fused-pyrrolyl compounds, pharmaceutical compositions and methods for use thereof. More particularly, the pyrimidinyl substituted 7-azaindolyl compounds of the present invention are kinase inhibitors useful in treating or ameliorating a kinase mediated, angiogenesis-mediated or hyperproliferative disorder.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR-α, PDGFR-β, Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (1-4), CamKK, Chk1 and 2 (Checkpoint kinases), CK1, CK2, Erk, IKK-1 (also IKK-ALPHA or CHUK), IKK-2 (also IKK-BETA), Ilk, Jnk (1-3), LimK (1 and 2), MLK3, Raf (A, B, and C), CDK (1-10), PKC (including all PKC subtypes), Plk (1-3), NIK, Pak (1-3), PDK1, PKR, RhoK, RIP, RIP-2, GSK3 (A and B), PKA, P38, Erk (1-3), PKB (including all PKB subtypes) (also AKT-1, AKT-2, AKT-3 or AKT3-1), IRAKI, FRK, SGK, TAKI or Tpl-2 (also COT).

Protein kinases play very important roles in the normal regulation of cell growth. However, as a result of either mutation or overexpression of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Uncontrolled signaling for cell growth due to defective control of protein phosphorylation has also been implicated in a number of diseases and disease conditions, such as osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus CMV), heart disease (such as atherosclerosis, neointima formation or transplantation-induced vasculopathies (such as restenosis and the like), lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like). Therefore, kinase inhibitors have potential use as therapeutic agents.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG1478 has been shown to reduce the viral load in cells that were infected in the presence of the tyrphostin (Wang, et al., Nature, 24 Jul. 2003, Vol 424). Accordingly, potent EGFR selective inhibitors may be useful in anti-CMV therapy.

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

CDKs constitute a class of enzymes that play critical roles in regulating the transitions between different phases of the cell cycle, such as the progression from a quiescent stage in G$_1$ (the gap between mitosis and the onset of DNA replication for a new round of cell division) to S (the period of DNA synthesis), or the progression from G$_2$ to M phase, in which active mitosis and cell-division occur. See, e.g., the articles compiled in *Science*, vol. 274 (1996), p. 1643-1677; and *Ann. Rev. Cell Dev. Biol*, vol. 13 (1997), pp. 261-291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell cycle.

The D cyclins are sensitive to extracellular growth signals and become activated in response to mitogens during the G$_1$ phase of the cell cycle. CDK4/cyclin D plays an important role in cell cycle progression by phosporylating, and thereby inactivating, the retinoblastoma protein (Rb). Hypophosphorylated Rb binds to the E2F family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the G$_1$ phase, whereby sensitivity to extracellular growth or inhibitory signals is lost and the cell is committed to cell division. During late G$_1$, Rb is also phosphorylated and inactivated by CDK2/cyclin E, and recent evidence indicates that CDK2/cyclin E can regulate progression into S phase through a parallel pathway that is independent of Rb phosphorylation (see Lukas et al., "Cyclin E-induced S Phase Without Activation of the pRb/E2F Pathway," *Genes and Dev.*, vol. 11 (1997), pp. 1479-1492).

The progression from G$_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be "reigned in", in response to DNA damage or negative growth stimuli, by the induction of endogenous inhibitory proteins. These naturally occurring protein inhibitors include p21$^{WAF1/CIP1}$, p27$^{KIP1}$, and the p16$^{INK4}$ family, the latter of which inhibit CDK4 exclusively (see Harper, "Cyclin Dependent Kinase Inhibitors," *Cancer Surv.*, vol. 29 (1997), pp. 91-107). Aberrations in this control system, particularly those that affect the function of CDK4 and CDK2, are implicated in the advancement of cells to the highly proliferative state characteristic of malignancies, such as familial melanomas, esophageal carcinomas, and pancreatic cancers (see, e.g., Hall and Peters, "Genetic Alterations of Cyclins, Cyclin-Dependent Kinases, and CDK Inhibitors in Human Cancer," *Adv. Cancer Res.*, vol. 68 (1996), pp. 67-108; and Kamb et al., "A Cell Cycle Regulator Potentially Involved in Genesis of Many Tumor Types," *Science*, vol. 264 (1994), pp. 436-440). Over-expression of cyclin D1 is linked to esophageal, breast, and squamous cell carcinomas (see, e.g., DelSal et al., "Cell Cycle and Cancer: Critical Events at the G$_1$ Restriction Point," *Critical Rev. Oncogenesis*, vol. 71 (1996), pp. 127-142).

Angiogenesis plays a role in various processes including development of the vasculature, wound healing and maintenance of the female reproductive system. Pathological angiogenesis is associated with disease states such as cancer, diabetic retinopathy, rheumatoid arthritis, endometriosis and psoriasis. Solid-tumor cancers, in particular, are dependent on angiogenesis for their growth. The vascular endothelial growth factors (VEGFs) are mediators of both normal and pathologic angiogenesis. VEGF transmits signals into cells through their cognate receptors, which belong to the receptor tyrosine kinase (RTK) family of transmembrane receptors. These receptors are tripartite, consisting of an extracellular ligand-binding domain, a transmembrane domain, which anchors the receptor in the membrane of the cell, and an intracellular tyrosine kinase domain.

One subfamily of RTKs comprises the receptors Flt1/VEGF-R1 and KDR/Flk1/VEGF-R2, which bind VEGFs. Binding of the VEGF ligand to the receptor results in stimulation of the receptor tyrosine kinase activity and transduction of biological signals into the cell. The KDR/Flk1/VEGF-R2 receptor mediates the biological activities of mitogenesis and proliferation of endothelial cells while the Flt1/VEGF-R1 receptor mediates functions such as endothelial cell adhesion. Inhibition of KDR/Flk1/VEGF-R2 signalling has been shown to inhibit the process of angiogenesis. Inhibitors of this receptor are likely useful in controlling or limiting angiogenesis.

Another RTK subfamily, the epidermal growth factor receptor (EGFR) tyrosine-kinase family, includes the receptors EGFR (also referred to as EGFR-1 or Erb-B1), HER-2 (or neu), EGFR3 and EGFR4. The Epidermal Growth Factor (EGF) and, Transforming Growth Factor-α (TGF-α) and HER-2 ligand heregulin are three of the ligands that bind to the EGFR receptors.

For example, EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs. Diseases associated with increased EGFR expression include proliferative glomerulonephritis, diabetes-induced renal disease and chronic pancreatitis. Overexpression of HER2 has been associated with breast and ovarian cancer. Diseases associated with the overproduction of TGF-α, rather than overexpression of EGFR, include psoriasis, a cell-proliferative skin disorder. Since EGFR expression levels in uterine tissues are elevated during implantation of a fertilized egg, an EGFR inhibitor may also have potential use as a contraceptive to reduce fertility.

Aurora kinases are highly conserved and found in all organisms where they function to regulate microtubule dynamics during the M phase of the cell cycle. Aurora-A associates with the centrosome around the pericentriolar material, as well as the mnicrotubules at the bipolar mitotic-spindle poles and the midbody microtubules. The kinase is involved in centrosome separation, duplication and maturation as well as in bipolar spindle assembly and stability. Aurora-A is overexpressed in a number of different human cancers and tumor cell lines. Overexpression of Aurora is sufficient to induce growth in soft agar and transforms cells making them tumorigenic. Inhibition of Aurora activity results in centrosome/chromosome segregation defects leading to monopolar spindles and polyploidy which arrests cells and induces apoptosis.

Germline mutations in the RET proto-oncogene are responsible for multiple endocrine neoplasia type 2, a dominantly inherited cancer syndrome. Moreover, somatic rearrangements of RET are causally involved in the genesis of papillary thyroid carcinoma. Rearrangements of RET in papillary thyroid carcinoma (called RET/PTC), juxtapose the region coding for the tyrosine kinase domain with the 5 prime-terminal regions of a variety of unrelated genes. RET/PTC oncogenes code for fusion proteins that display a constitutive tyrosine kinase activity. The receptor tyrosine kinase encoded by the RET gene normally functions as the subunit of a complex that binds four distinct ligands and activates a signalling network crucial for neural and kidney development.

There is a need, for small-molecule compounds that may be readily synthesized and are potent inhibitors of one or more CDK, VEGF-R2 kinase, HER2 kinase, Aurora-A kinase, or RET receptor kinase that possess anti-tumor cell proliferation activity, and as such are useful in treating or ameliorating a CDK, VEGF-R2 kinase, HER2 kinase, Aurora-A kinase, or RET receptor kinase mediated, angiogenesis-mediated or hyperproliferative disorder.

SUMMARY OF THE INVENTION

Accordingly, one object of the invention is to attain compounds and drug compositions that inhibit the activity of one or more of the CDK, VEGF-R2 kinase, HER2 kinase, Aurora-A kinase, or RET kinase receptors. A further object is to provide an effective method of treating cancer indications and kinase mediated, angiogenesis-mediated or hyperproliferative disorders through CDK, VEGF-R2, HER2, Aurora-A or RET inhibition. Another object is to achieve pharmaceutical compositions containing compounds effective to inhibit the proliferation of cancer cells. These and other objects and advantages of the invention, which will become apparent in light of the detailed description below, are achieved through use of the compounds of the invention described below.

The present invention provides pyrimidinyl substituted fused-pyrrolyl compounds of Formula (I):

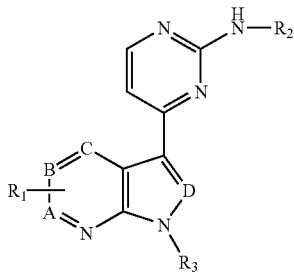

Formula (I)

and pharmaceutically acceptable forms thereof, wherein
A, B, and C are independently selected from the group consisting of CH and N,
D is selected from the group consisting of N and C—$R_4$,
$R_1$ is hydrogen or one, two or three independently selected substituents substituted on a carbon atom selected from the group consisting of
(1) $C_{1-8}$alkyl,
(2) $C_{2-8}$alkenyl,
(3) $C_{2-8}$alkynyl,
(4) $C_{1-8}$alkoxy,
wherein (1), (2), (3) and (4) are optionally substituted with one, two or three substituents independently selected from the group consisting of $C_{1-8}$alkoxy, $NH_2$, $NH(C_{1-8}$alkyl), $N(C_{1-8}$alkyl$)_2$, $NH(C_{1-8}$alkyl-$C_{1-8}$alkoxy), $N(C_{1-8}$alkyl-$C_{1-8}$alkoxy$)_2$, nitro, cyano, (halogen$)_{1-3}$ and hydroxy; and
wherein (1), (2), (3) and (4) are optionally substituted with a ring system selected from the group consisting of $C_{3-8}$cycloalkyl, aryl, heteroaryl, and heterocyclyl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen$)_{1-3}$, $C_{1-8}$alkoxy(halogen$)_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, $NH(C_{1-8}$alkyl), $N(C_{1-8}$alkyl$)_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl$)_2$, $S(C_{1-8}$alkyl), $S(O)(C_{1-8}$alkyl), $SO_2(C_{1-8}$alkyl), C(O)$NH_2$, C(O)NH($C_{1-8}$alkyl), C(O)N($C_{1-8}$alkyl$)_2$, NHC(O)$NH_2$, NHC(O)NH($C_{1-8}$alkyl), NHC(O)N($C_{1-8}$alkyl$)_2$, $NHSO_2NH_2$, $NHSO_2NH(C_{1-8}$alkyl), $NHSO_2N(C_{1-8}$alkyl$)_2$, $SO_2NH_2$, $SO_2NH(C_{1-8}$alkyl), and $SO_2N(C_{1-8}$alkyl$)_2$,
(5) N substituted with two substituents independently selected from the group consisting of
(a) hydrogen,
(b) $C_{1-8}$alkyl optionally substituted with a substituent selected from the group consisting of $C_{1-8}$alkoxy, $NH_2$, $NH(C_{1-8}$alkyl), $N(C_{1-8}$alkyl$)_2$, $NH(C_{1-8}$alkyl-$C_{1-8}$alkoxy), $N(C_{1-8}$alkyl-$C_{1-8}$alkoxy$)_2$, nitro, cyano, (halogen$)_{1-3}$, hydroxy and a ring system, and
(c) a ring system, wherein the (b) and (c) ring system is selected from the group consisting of $C_{3-8}$cycloalkyl, heterocyclyl, aryl and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen$)_{1-3}$, $C_{1-8}$alkoxy(halogen$)_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, $NH(C_{1-8}$alkyl), $N(C_{1-8}$alkyl$)_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl$)_2$, $S(C_{1-8}$alkyl), $S(O)(C_{1-8}$alkyl), $SO_2(C_{1-8}$alkyl), C(O)$NH_2$, C(O)NH($C_{1-8}$alkyl), C(O)N($C_{1-8}$alkyl$)_2$, NHC(O)$NH_2$, NHC(O)NH($C_{1-8}$alkyl), NHC(O)N($C_{1-8}$alkyl$)_2$, $NHSO_2NH_2$, $NHSO_2NH(C_{1-8}$alkyl), $NHSO_2N(C_{1-8}$alkyl$)_2$, $SO_2NH_2$, $SO_2NH(C_{1-8}$alkyl), and $SO_2N(C_{1-8}$alkyl$)_2$,
(6) $NHSO_2$ substituted on $SO_2$ with a substituent selected from the group consisting of
(a) $C_{1-8}$alkyl optionally substituted with a substituent selected from the group consisting of $C_{1-8}$alkoxy, $NH_2$, $NH(C_{1-8}$alkyl), $N(C_{1-8}$alkyl$)_2$, $NH(C_{1-8}$alkyl-$C_{1-8}$alkoxy), $N(C_{1-8}$alkyl-$C_{1-8}$alkoxy$)_2$, nitro, cyano, (halogen$)_{1-3}$, hydroxy and a ring system, and
(b) a ring system, wherein the (a) and (b) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen$)_{1-3}$, $C_{1-8}$alkoxy(halogen$)_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, $NH(C_{1-8}$alkyl), $N(C_{1-8}$alkyl$)_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl$)_2$, $S(C_{1-8}$alkyl), $S(O)(C_{1-8}$alkyl), $SO_2(C_{1-8}$alkyl), C(O)$NH_2$, C(O)NH($C_{1-8}$alkyl), C(O)N($C_{1-8}$alkyl$)_2$, NHC(O)$NH_2$, NHC(O)NH($C_{1-8}$alkyl), NHC(O)N($C_{1-8}$alkyl$)_2$, $NHSO_2NH_2$, $NHSO_2NH(C_{1-8}$alkyl), $NHSO_2N(C_{1-8}$alkyl$)_2$, $SO_2NH_2$, $SO_2NH(C_{1-8}$alkyl), and $SO_2N(C_{1-8}$alkyl$)_2$,
(7) $SO_2N$ substituted on N with two substituents independently selected from the group consisting of
(a) hydrogen,
(b) $C_{1-8}$alkyl optionally substituted with a substituent selected from the group consisting of $C_{1-8}$alkoxy, $NH_2$, $NH(C_{1-8}$alkyl), $N(C_{1-8}$alkyl$)_2$, $NH(C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and (c) a ring system, wherein the (b) and (c) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2(C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (8) $SO_2$ substituted with a substituent selected from the group consisting of (a) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and (b) a ring system, wherein the (a) and (b) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2(C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (9) S substituted with a substituent selected from the group consisting of (a) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and (b) a ring system, wherein the (a) and (b) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2(C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$,

(10) S(O) substituted with a substituent selected from the group consisting of (a) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and (b) a ring system, wherein the (a) and (b) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2(C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$,

(11) $NHSO_2$N substituted on N with two substituents independently selected from the group consisting of (a) hydrogen, (b) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and (c) a ring system, wherein the (b) and (c) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2(C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$,

(12) C(O)N substituted on N with two substituents independently selected from the group consisting of (a) hydrogen, (b) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and (c) a ring system, wherein the (b) and (c) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-NH$_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), SO$_2$($C_{1-8}$alkyl), C(O)NH$_2$, C(O)NH($C_{1-8}$alkyl), C(O)N($C_{1-8}$alkyl)$_2$, NHC(O)NH$_2$, NHC(O)NH($C_{1-8}$alkyl), NHC(O)N($C_{1-8}$alkyl)$_2$, NHSO$_2$NH$_2$, NHSO$_2$NH($C_{1-8}$alkyl), NHSO$_2$N($C_{1-8}$alkyl)$_2$, SO$_2$NH$_2$, SO$_2$NH($C_{1-8}$alkyl), and SO$_2$N($C_{1-8}$alkyl)$_2$,

(13) NHC(O), substituted on C(O) with a substituent selected from the group consisting of
 (a) hydrogen,
 (b) $C_{1-8}$alkyl optionally substituted with a substituent selected from the group consisting of $C_{1-8}$alkoxy, NH$_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
 (c) a ring system, wherein the (b) and (c) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), CO$_2$H, CO$_2$($C_{1-8}$alkyl), COH, C(O)($C_{1-8}$alkyl), NH$_2$, NH($C_{1-8}$alkyl), N($C_{1-8}$alkyl)$_2$, cyano, halogen, hydroxy, nitro, $C_{1-8}$alkyl-NH$_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), SO$_2$($C_{1-8}$alkyl), C(O)NH$_2$, C(O)NH($C_{1-8}$alkyl), C(O)N($C_{1-8}$alkyl)$_2$, NHC(O)NH$_2$, NHC(O)NH($C_{1-8}$alkyl), NHC(O)N($C_{1-8}$alkyl)$_2$, NHSO$_2$NH$_2$, NHSO$_2$NH($C_{1-8}$alkyl), NHSO$_2$N($C_{1-8}$alkyl)$_2$, SO$_2$NH$_2$, SO$_2$NH($C_{1-8}$alkyl), and SO$_2$N($C_{1-8}$alkyl)$_2$,

(14) C(O) substituted with a substituent selected from the group consisting of
 (a) hydrogen,
 (b) $C_{1-8}$alkyl optionally substituted with a substituent selected from the group consisting of $C_{1-8}$alkoxy, NH$_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
 (c) a ring system, wherein the (b) and (c) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), CO$_2$H, CO$_2$($C_{1-8}$alkyl), COH, C(O)($C_{1-8}$alkyl), NH$_2$, NH($C_{1-8}$alkyl), N($C_{1-8}$alkyl)$_2$, cyano, halogen, hydroxy, nitro, $C_{1-8}$alkyl-NH$_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), SO$_2$($C_{1-8}$alkyl), C(O)NH$_2$, C(O)NH($C_{1-8}$alkyl), C(O)N($C_{1-8}$alkyl)$_2$, NHC(O)NH$_2$, NHC(O)NH($C_{1-8}$alkyl), NHC(O)N($C_{1-8}$alkyl)$_2$, NHSO$_2$NH$_2$, NHSO$_2$NH($C_{1-8}$alkyl), NHSO$_2$N($C_{1-8}$alkyl)$_2$, SO$_2$NH$_2$, SO$_2$NH($C_{1-8}$alkyl), and SO$_2$N($C_{1-8}$alkyl)$_2$,

(15) NHC(O)N, substituted on N with two substituents independently selected from the group consisting of
 (a) hydrogen,
 (b) $C_{1-8}$alkyl optionally substituted with a substituent selected from the group consisting of $C_{1-8}$alkoxy, NH$_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
 (c) a ring system, wherein the (b) and (c) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), CO$_2$H, CO$_2$($C_{1-8}$alkyl), COH, C(O)($C_{1-8}$alkyl), NH$_2$, NH($C_{1-8}$alkyl), N($C_{1-8}$alkyl)$_2$, cyano, halogen, hydroxy, nitro, $C_{1-8}$alkyl-NH$_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), SO$_2$($C_{1-8}$alkyl), C(O)NH$_2$, C(O)NH($C_{1-8}$alkyl), C(O)N($C_{1-8}$alkyl)$_2$, NHC(O)NH$_2$, NHC(O)NH($C_{1-8}$alkyl), NHC(O)N($C_{1-8}$alkyl)$_2$, NHSO$_2$NH$_2$, NHSO$_2$NH($C_{1-8}$alkyl), NHSO$_2$N($C_{1-8}$alkyl)$_2$, SO$_2$NH$_2$, SO$_2$NH($C_{1-8}$alkyl), and SO$_2$N($C_{1-8}$alkyl)$_2$,

(16) halogen,
(17) hydroxy,
(18) cyano,
(19) nitro, and
(20) a ring system selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), CO$_2$H, CO$_2$($C_{1-8}$alkyl), COH, C(O)($C_{1-8}$alkyl), NH$_2$, NH($C_{1-8}$alkyl), N($C_{1-8}$alkyl)$_2$, cyano, halogen, hydroxy, nitro, $C_{1-8}$alkyl-NH$_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), SO$_2$($C_{1-8}$alkyl), C(O)NH$_2$, C(O)NH($C_{1-8}$alkyl), C(O)N($C_{1-8}$alkyl)$_2$, NHC(O)NH$_2$, NHC(O)NH($C_{1-8}$alkyl), NHC(O)N($C_{1-8}$alkyl)$_2$, NHSO$_2$NH$_2$, NHSO$_2$NH($C_{1-8}$alkyl), NHSO$_2$N($C_{1-8}$alkyl)$_2$, SO$_2$NH$_2$, SO$_2$NH($C_{1-8}$alkyl), and SO$_2$N($C_{1-8}$alkyl)$_2$, R$_2$ is selected from the group consisting of
(1) $C_{3-8}$cycloalkyl,
(2) aryl,
(3) heteroaryl,
(4) heterocyclyl, and
(5) $C_{1-8}$alkyl substituted with $C_{3-8}$cycloalkyl, aryl, heteroaryl, or heterocyclyl, wherein (1), (2), (3) and (4) and the $C_{3-8}$cycloalkyl, aryl, heteroaryl and heterocyclyl portion of (5) are each optionally substituted on a ring carbon atom or saturated nitrogen atom with from one, two, three, four or five substituents each independently selected from the group consisting of
(A) $C_{1-8}$alkyl,
(B) $C_{2-8}$alkenyl,
(C) $C_{2-8}$alkynyl,
(D) $C_{1-8}$alkoxy, wherein (A), (B), (C) and (D) are optionally substituted with one, two or three substituents independently selected from the group consisting of $C_{1-8}$alkoxy, NH$_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$ and hydroxy; and wherein (A), (B), (C) and (D) are optionally substituted with a ring system selected from the group consisting of $C_{3-8}$cycloalkyl, aryl, heteroaryl, and heterocyclyl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), CO$_2$H, CO$_2$($C_{1-8}$alkyl), COH, C(O)($C_{1-8}$alkyl), NH$_2$, NH($C_{1-8}$alkyl), N($C_{1-8}$alkyl)$_2$, cyano, halogen, hydroxy, nitro, $C_{1-8}$alkyl-NH$_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (E) N substituted with two substituents independently selected from the group consisting of
(i) hydrogen,
(ii) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2$($C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (F) $NHSO_2$ substituted on $SO_2$ with a substituent selected from the group consisting of
(i) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
(ii) a ring system, wherein the (i) and (ii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2$($C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (G) $SO_2$N substituted on N with two substituents independently selected from the group consisting of
(i) hydrogen,
(ii) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2$($C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (H) $SO_2$ substituted with a substituent selected from the group consisting of
(i) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
(ii) a ring system, wherein the (i) and (ii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2$($C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (I) S substituted with a substituent selected from the group consisting of
(i) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
(ii) a ring system, wherein the (i) and (ii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2$($C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, (J) S(O) substituted with a substituent selected from the group consisting of
(i) $C_{1-8}$alkyl optionally substituted with a substituent selected from the group consisting of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, (halogen)$_{1-3}$, hydroxy and a ring system, and
(ii) a ring system, wherein the (i) and (ii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy (halogen)$_{1-3}$, $C_{1-8}$alkyl(hydroxy), $C_{1-8}$alkoxy(hydroxy), $CO_2H$, $CO_2(C_{1-8}$alkyl), COH, $C(O)(C_{1-8}$alkyl), $NH_2$, $NH(C_{1-8}$alkyl), $N(C_{1-8}$alkyl)$_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl)$_2$, $S(C_{1-8}$alkyl), $S(O)(C_{1-8}$alkyl), $SO_2(C_{1-8}$alkyl), $C(O)NH_2$, $C(O)NH(C_{1-8}$alkyl), $C(O)N(C_{1-8}$alkyl)$_2$, $NHC(O)NH_2$, $NHC(O)NH(C_{1-8}$alkyl), $NHC(O)N(C_{1-8}$alkyl)$_2$, $NHSO_2NH_2$, $NHSO_2NH(C_{1-8}$alkyl), $NHSO_2N(C_{1-8}$alkyl)$_2$, $SO_2NH_2$, $SO_2NH(C_{1-8}$alkyl), and $SO_2N(C_{1-8}$alkyl)$_2$, (K) $NHSO_2N$ substituted on N with two substituents independently selected from the group consisting of
(i) hydrogen,
(ii) $C_{1-8}$alkyl optionally substituted with a substituent selected from the group consisting of $C_{1-8}$alkoxy, $NH_2$, $NH(C_{1-8}$alkyl), $N(C_{1-8}$alkyl)$_2$, $NH(C_{1-8}$alkyl-$C_{1-8}$alkoxy), $N(C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, $C(O)(C_{1-8}$alkyl), $NH_2$, $NH(C_{1-8}$alkyl), $N(C_{1-8}$alkyl)$_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl)$_2$, $S(C_{1-8}$alkyl), $S(O)(C_{1-8}$alkyl), $SO_2(C_{1-8}$alkyl), $C(O)NH_2$, $C(O)NH(C_{1-8}$alkyl), $C(O)N(C_{1-8}$alkyl)$_2$, $NHC(O)NH_2$, $NHC(O)NH(C_{1-8}$alkyl), $NHC(O)N(C_{1-8}$alkyl)$_2$, $NHSO_2NH_2$, $NHSO_2NH(C_{1-8}$alkyl), $NHSO_2N(C_{1-8}$alkyl)$_2$, $SO_2NH_2$, $SO_2NH(C_{1-8}$alkyl), and $SO_2N(C_{1-8}$alkyl)$_2$, (L) C(O)N substituted on N with two substituents independently selected from the group consisting of
(i) hydrogen,
(ii) $C_{1-8}$alkyl optionally substituted with a substituent selected from the group consisting of $C_{1-8}$alkoxy, $NH_2$, $NH(C_{1-8}$alkyl), $N(C_{1-8}$alkyl)$_2$, $NH(C_{1-8}$alkyl-$C_{1-8}$alkoxy), $N(C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, $C(O)(C_{1-8}$alkyl), $NH_2$, $NH(C_{1-8}$alkyl), $N(C_{1-8}$alkyl)$_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl)$_2$, $S(C_{1-8}$alkyl), $S(O)(C_{1-8}$alkyl), $SO_2(C_{1-8}$alkyl), $C(O)NH_2$, $C(O)NH(C_{1-8}$alkyl), $C(O)N(C_{1-8}$alkyl)$_2$, $NHC(O)NH_2$, $NHC(O)NH(C_{1-8}$alkyl), $NHC(O)N(C_{1-8}$alkyl)$_2$, $NHSO_2NH_2$, $NHSO_2NH(C_{1-8}$alkyl), $NHSO_2N(C_{1-8}$alkyl)$_2$, $SO_2NH_2$, $SO_2NH(C_{1-8}$alkyl), and $SO_2N(C_{1-8}$alkyl)$_2$, (M) NHC(O) substituted on C(O) with a substituent selected from the group consisting of
(i) hydrogen,
(ii) $C_{1-8}$alkyl optionally substituted with a substituent selected from the group consisting of $C_{1-8}$alkoxy, $NH_2$, $NH(C_{1-8}$alkyl), $N(C_{1-8}$alkyl)$_2$, $NH(C_{1-8}$alkyl-$C_{1-8}$alkoxy), $N(C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, $C(O)(C_{1-8}$alkyl), $NH_2$, $NH(C_{1-8}$alkyl), $N(C_{1-8}$alkyl)$_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl)$_2$, $S(C_{1-8}$alkyl), $S(O)(C_{1-8}$alkyl), $SO_2(C_{1-8}$alkyl), $C(O)NH_2$, $C(O)NH(C_{1-8}$alkyl), $C(O)N(C_{1-8}$alkyl)$_2$, $NHC(O)NH_2$, $NHC(O)NH(C_{1-8}$alkyl), $NHC(O)N(C_{1-8}$alkyl)$_2$, $NHSO_2NH_2$, $NHSO_2NH(C_{1-8}$alkyl), $NHSO_2N(C_{1-8}$alkyl)$_2$, $SO_2NH_2$, —$SO_2NH(C_{1-8}$alkyl), and $SO_2N(C_{1-8}$alkyl)$_2$, (N) C(O) substituted with a substituent selected from the group consisting of
(i) hydrogen,
(ii) $C_{1-8}$alkyl optionally substituted with a substituent selected from the group consisting of $C_{1-8}$alkoxy, $NH_2$, $NH(C_{1-8}$alkyl), $N(C_{1-8}$alkyl)$_2$, $NH(C_{1-8}$alkyl-$C_{1-8}$alkoxy), $N(C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, $C(O)(C_{1-8}$alkyl), $NH_2$, $NH(C_{1-8}$alkyl), $N(C_{1-8}$alkyl)$_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl)$_2$, $S(C_{1-8}$alkyl), $S(O)(C_{1-8}$alkyl), $SO_2(C_{1-8}$alkyl), $C(O)NH_2$, $C(O)NH(C_{1-8}$alkyl), $C(O)N(C_{1-8}$alkyl)$_2$, $NHC(O)NH_2$, $NHC(O)NH(C_{1-8}$alkyl), $NHC(O)N(C_{1-8}$alkyl)$_2$, $NHSO_2NH_2$, $NHSO_2NH(C_{1-8}$alkyl), $NHSO_2N(C_{1-8}$alkyl)$_2$, $SO_2NH_2$, $SO_2NH(C_{1-8}$alkyl), and $SO_2N(C_{1-8}$alkyl)$_2$, (O) NHC(O)N, substituted on N with two substituents independently selected from the group consisting of
(i) hydrogen,
(ii) $C_{1-8}$alkyl optionally substituted with a substituent selected from the group consisting of $C_{1-8}$alkoxy, $NH_2$, $NH(C_{1-8}$alkyl), $N(C_{1-8}$alkyl)$_2$, $NH(C_{1-8}$alkyl-$C_{1-8}$alkoxy), $N(C_{1-8}$alkyl-$C_{1-8}$alkoxy)$_2$, nitro, cyano, (halogen)$_{1-3}$, hydroxy and a ring system, and
(iii) a ring system, wherein the (ii) and (iii) ring system is selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, $C(O)(C_{1-8}$alkyl), $NH_2$, $NH(C_{1-8}$alkyl), $N(C_{1-8}$alkyl)$_2$, cyano, halogen, hydroxy, nitro, $C_{1-8}$alkyl-$NH_2$, $C_{1-8}$alkyl-$NH(C_{1-8}$alkyl), $C_{1-8}$alkyl-$N(C_{1-8}$alkyl)$_2$, $S(C_{1-8}$alkyl), $S(O)(C_{1-8}$alkyl), $SO_2(C_{1-8}$alkyl), $C(O)NH_2$, $C(O)NH(C_{1-8}$alkyl), $C(O)N(C_{1-8}$alkyl)$_2$, $NHC(O)NH_2$, $NHC(O)NH(C_{1-8}$alkyl), $NHC(O)N(C_{1-8}$alkyl)$_2$, $NHSO_2NH_2$, $NHSO_2NH(C_{1-8}$alkyl), $NHSO_2N(C_{1-8}$alkyl)$_2$, $SO_2NH_2$, $SO_2NH(C_{1-8}$alkyl), and $SO_2N(C_{1-8}$alkyl)$_2$, (P) halogen,
(Q) hydroxy,
(R) cyano,
(S) nitro, and
(T) a ring system selected from the group consisting of $C_{3-8}$cycloalkyl, heterocyclyl, aryl, and heteroaryl; wherein the ring system is optionally substituted with from one, two, three, four or five substituents independently selected from the group consisting of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy (halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen; hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2(C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, $R_3$ is selected from the group consisting of hydrogen, $C_{1-8}$alkyl, $C_{1-8}$alkyl($C_{1-8}$alkoxy), $C_{1-8}$alkyl(halogen)$_{1-3}$, $C_{1-8}$alkyl(hydroxy), $CO_2H$, $CO_2(C_{1-8}$alkyl), COH, C(O)($C_{1-8}$alkyl), hydroxy, $C_{1-8}$alkyl-$NH_2$, $C_{1-8}$alkyl-NH($C_{1-8}$alkyl), $C_{1-8}$alkyl-N($C_{1-8}$alkyl)$_2$, $C_{1-8}$alkyl(hydroxy)-NH($C_{1-8}$alkyl), $C_{1-8}$alkyl(hydroxy)-N($C_{1-8}$alkyl)$_2$, $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$, and $R_4$ is selected from the group consisting of hydrogen, $C_{1-8}$alkyl, $C_{1-8}$alkoxy, $C_{1-8}$alkyl($C_{1-8}$alkoxy), $C_{1-8}$alkyl (halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)$NH_2$, C(O)NH($C_{1-8}$alkyl), C(O)N($C_{1-8}$alkyl)$_2$, NHC(O)$NH_2$, NHC(O)NH($C_{1-8}$alkyl), NHC(O)N($C_{1-8}$alkyl)$_2$, $NHSO_2NH_2$, $NHSO_2$NH($C_{1-8}$alkyl), $NHSO_2$N($C_{1-8}$alkyl)$_2$, $SO_2NH_2$, $SO_2$NH($C_{1-8}$alkyl), and $SO_2$N($C_{1-8}$alkyl)$_2$.

An example of the present invention is a pyrimidinyl substituted fused-pyrrolyl compound of Formula (I), wherein the compound is a CDK, VEGF-R2 kinase, HER2 kinase, Aurora-A kinase, or RET kinase inhibitor.

The present invention provides a method for using compounds of Formula (I) in treating or ameliorating a kinase receptor-mediated disorder.

An example of the method includes inhibiting unregulated kinase activity comprising contacting the kinase domain with one or more compounds of Formula (I).

An example of the method includes inhibiting a kinase by contacting the kinase receptor with a compound of Formula (I).

An example of the method includes inhibiting increased or unregulated kinase expression or signaling leading to unregulated cell proliferation comprising contacting a kinase receptor with one or more compounds of Formula (I).

The present invention also provides a method for using the pyrimidinyl substituted fused-pyrrolyl compounds of Formula (I) in treating or ameliorating a CDK, VEGF-R2 kinase, HER2 kinase, Aurora-A kinase, or RET receptor kinase-mediated, angiogenesis-mediated, or hyperproliferative disorder.

These properties could be used for the treatment of disease mediated by abnormal cell cycles and cell proliferation such as cancers (solid tumors and leukemias), fibroproliferative and differentiative disorders, psoriasis, acute and chronic nephropathies, rheumatoid arthritis, Kaposi's sarcoma, haemangioma atheroma, atherosclerosis, arterial restenosis, autoimmune disease, acute and chronic inflammation, bone diseases and ocular diseased with retinal vessel proliferation.

The present invention is further directed to a method for inhibiting a kinase selected from the group consisting of CDK, VEGF-R2 kinase, HER2 kinase, Aurora-A kinase and RET kinase by contacting the kinase receptor with a compound of Formula (I).

An example of the method includes inhibiting a cyclin dependent kinase by contacting the kinase receptor with a compound of Formula (I).

An example of the method includes inhibiting the unregulated expression of a cyclin dependent kinase and the like.

Accordingly, the present invention is also directed to a method for treating or ameliorating a kinase mediated disorder in a patient in need thereof comprising administering to the patient an effective amount of a compound of Formula (I).

The present invention further provides a method for treating or ameliorating a CDK, VEGF-R2 kinase, HER2 kinase, Aurora-A kinase, or RET receptor kinase mediated disorder in a patient in need thereof comprising administering to the patient an effective amount of a compound of Formula (I) for treating or ameliorating a CDK, VEGF-R2 kinase, HER2 kinase, Aurora-A kinase, or RET receptor kinase mediated disorder.

DETAILED DESCRIPTION OF THE INVENTION

The present invention is directed to a compound of Formula (Ia):

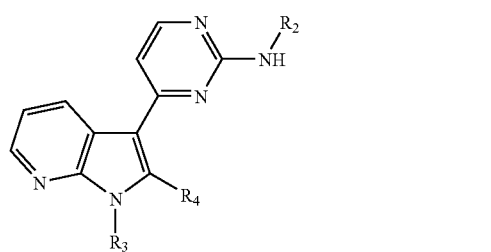

Formula (Ia)

and pharmaceutically acceptable forms thereof, wherein $R_2$ is selected from $C_{3-8}$cycloalkyl, aryl, heteroaryl, heterocyclyl or $C_{1-8}$alkyl substituted with $C_{3-8}$cycloalkyl, aryl, heteroaryl or heterocyclyl, optionally substituted on each of $C_{3-8}$cycloalkyl, aryl, heteroaryl and heterocyclyl with one or more of $C_{1-8}$alkyl, $C_{2-8}$alkenyl, $C_{2-8}$alkynyl, $C_{1-8}$alkoxy, —N—, —$NHSO_2$—, —$SO_2$N—, —$SO_2$—, —S—, —S(O)—, —$NHSO_2$N—, —C(O)N—, —NHC(O)—, —C(O)—, —NHC(O)N—, nitro, cyano, halogen, hydroxy or $R_{2a}$, wherein $C_{1-8}$alkyl, $C_{2-8}$alkenyl, $C_{2-8}$alkynyl and $C_{1-8}$alkoxy are each optionally substituted with one or more of $C_{1-8}$alkoxy, $NH_2$, NH($C_{1-8}$alkyl), N($C_{1-8}$alkyl)$_2$, NH($C_{1-8}$alkyl-$C_{1-8}$alkoxy), N($C_{1-8}$alkyl-$C_{1-8}$alkoxy)$_2$, nitro, cyano, halogen, hydroxy, $C_{3-8}$cycloalkyl, aryl, heteroaryl or heterocyclyl, optionally substituted on each of $C_{3-8}$cycloalkyl, aryl, heteroaryl and heterocyclyl with one or more of $C_{1-8}$alkyl, $C_{1-8}$alkoxy, $C_{1-8}$alkyl($C_{1-8}$alkoxy), $C_{1-8}$alkyl(halogen)$_{1-3}$, $C_{1-8}$alkoxy(halogen)$_{1-3}$, $C_{1-8}$alkyl(hydroxy), $C_{1-8}$alkoxy(hydroxy), $CO_2H$, $CO_2(C_{1-8}$alkyl), COH, C(O)($C_{1-8}$alkyl), $NH_2$, NH($C_{1-8}$alkyl), N($C_{1-8}$alkyl)$_2$, cyano, halogen, hydroxy, nitro, $C_{1-8}$alkyl-$NH_2$, $C_{1-8}$alkyl-NH($C_{1-8}$alkyl), $C_{1-8}$alkyl-N($C_{1-8}$alkyl)$_2$, S($C_{1-8}$alkyl), S(O)($C_{1-8}$alkyl), $SO_2$($C_{1-8}$alkyl), C(O)NH$_2$, C(O)NH(C$_{1-8}$alkyl), C(O)N(C$_{1-8}$alkyl)$_2$, NHC(O)NH$_2$, NHC(O)NH(C$_{1-8}$alkyl), NHC(O)N(C$_{1-8}$alkyl)$_2$, NHSO$_2$NH$_2$, NHSO$_2$NH(C$_{1-8}$alkyl), NHSO$_2$N(C$_{1-8}$alkyl)$_2$, SO$_2$NH$_2$, SO$_2$NH(C$_{1-8}$alkyl) or SO$_2$N(C$_{1-8}$alkyl)$_2$, wherein N is substituted with two substituents each selected from hydrogen, C$_{1-8}$alkyl, C$_{3-8}$cycloalkyl, heterocyclyl, aryl or heteroaryl, optionally substituted on C$_{1-8}$alkyl with one or more of C$_{1-8}$alkoxy, NH$_2$, NH(C$_{1-5}$alkyl), N(C$_{1-8}$alkyl)$_2$, NH(C$_{1-8}$alkyl-C$_{1-8}$alkoxy), N(C$_{1-8}$alkyl-C$_{1-8}$alkoxy)$_2$, nitro, cyano, halogen, hydroxy, C$_{3-8}$cycloalkyl, heterocyclyl, aryl or heteroaryl, wherein NHSO$_2$ and SO$_2$ are each substituted on SO$_2$ with C$_{1-8}$alkyl, C$_{3-8}$cycloalkyl, heterocyclyl, aryl or heteroaryl, optionally substituted on C$_{1-8}$alkyl with one or more of C$_{1-8}$alkoxy, NH$_2$, NH(C$_{1-8}$alkyl), N(C$_{1-8}$alkyl)$_2$, NH(C$_{1-8}$alkyl-C$_{1-8}$alkoxy), N(C$_{1-8}$alkyl-C$_{1-8}$alkoxy)$_2$, nitro, cyano, halogen, hydroxy, C$_{3-8}$cycloalkyl, heterocyclyl, aryl or heteroaryl, wherein SO$_2$N, NHSO$_2$N, C(O)N and NHC(O)N are each substituted on N with two substituents each selected from hydrogen, C$_{1-8}$alkyl, C$_{3-8}$cycloalkyl, heterocyclyl, aryl or heteroaryl, optionally substituted on C$_{1-8}$alkyl with one or more of C$_{1-8}$alkoxy, NH$_2$, NH(C$_8$alkyl), N(C$_{1-8}$alkyl)$_2$, NH(C$_{1-8}$alkyl-C$_{1-8}$alkoxy), N(C$_{1-8}$alkyl-C$_{1-8}$alkoxy)$_2$, nitro, cyano, halogen, hydroxy, C$_{3-8}$cycloalkyl, heterocyclyl, aryl or heteroaryl, wherein S and S(O) are each substituted with C$_{1-8}$alkyl, C$_{3-8}$cycloalkyl, heterocyclyl, aryl or heteroaryl, optionally substituted on C$_{1-8}$alkyl with one or more of C$_{1-8}$alkoxy, NH$_2$, NH(C$_{1-8}$alkyl), N(C$_{1-8}$alkyl)$_2$, NH(C$_{1-8}$alkyl-C$_{1-8}$alkoxy), N(C$_{1-8}$alkyl-C$_{1-8}$alkoxy)$_2$, nitro, cyano, halogen, hydroxy, C$_{3-8}$cycloalkyl, heterocyclyl, aryl or heteroaryl, wherein NHC(O) and C(O) are each substituted on C(O) with C$_{1-8}$alkyl, C$_{3-8}$cycloalkyl, heterocyclyl, aryl or heteroaryl, optionally substituted on C$_{1-8}$alkyl with one or more of C$_{1-8}$alkoxy, NH$_2$, NH(C$_{1-8}$alkyl), N(C$_{1-8}$alkyl)$_2$, NH(C$_{1-8}$alkyl-C$_{1-8}$alkoxy), N(C$_{1-8}$alkyl-C$_{1-8}$alkoxy)$_2$, nitro, cyano, halogen, hydroxy, C$_{3-8}$cycloalkyl, heterocyclyl, aryl or heteroaryl, R$_{2a}$ is selected from C$_{3-8}$cycloalkyl, heterocyclyl, aryl or heteroaryl each optionally substituted with one or more of C$_{1-8}$alkyl, C$_{1-8}$alkoxy, C$_{1-8}$alkyl(C$_{1-8}$alkoxy), C$_{1-8}$alkyl(halogen)$_{1-3}$, C$_{1-8}$alkoxy(halogen)$_{1-3}$, C$_{1-8}$alkyl(hydroxy), C$_{1-8}$alkoxy(hydroxy), CO$_2$H, CO$_2$(C$_{1-8}$alkyl), COH, C(O)(C$_{1-8}$alkyl), NH$_2$, NH(C$_{1-8}$alkyl), N(C$_{1-8}$alkyl)$_2$, cyano, halogen, hydroxy, nitro, C$_{1-8}$alkyl-NH$_2$, C$_{1-8}$alkyl-NH(C$_{1-8}$alkyl), C$_{1-8}$alkyl-N(C$_{1-8}$alkyl)$_2$, S(C$_{1-8}$alkyl), S(O)(C$_{1-8}$alkyl), SO$_2$(C$_{1-8}$alkyl), C(O)NH$_2$, C(O)NH(C$_{1-8}$alkyl), C(O)N(C$_{1-8}$alkyl)$_2$, NHC(O)NH$_2$, NHC(O)NH(C$_{1-8}$alkyl), NHC(O)N(C$_{1-8}$alkyl)$_2$, NHSO$_2$NH$_2$, NHSO$_2$NH(C$_{1-8}$alkyl), NHSO$_2$N(C$_{1-8}$alkyl)$_2$, SO$_2$NH$_2$, SO$_2$NH(C$_{1-8}$alkyl) or SO$_2$N(C$_{1-8}$alkyl)$_2$, R$_3$ is selected from hydrogen, C$_{1-8}$alkyl, C$_{1-8}$alkyl(C$_{1-8}$alkoxy), C$_{1-8}$alkyl(halogen)$_{1-3}$, C$_{1-8}$alkyl(hydroxy), CO$_2$H, CO$_2$(C$_{1-8}$alkyl), COH, C(O)(C$_{1-8}$alkyl), hydroxy, C$_{1-8}$alkyl-NH$_2$, C$_{1-8}$alkyl-NH(C$_{1-8}$alkyl), C$_{1-8}$alkyl-N(C$_{1-8}$alkyl)$_2$, C$_{1-8}$alkyl(hydroxy)-NH(C$_{1-8}$alkyl), C$_{1-8}$alkyl(hydroxy)-N(C$_{1-8}$alkyl)$_2$, SO$_2$(C$_{1-8}$alkyl), C(O)NH$_2$, C(O)NH(C$_{1-8}$alkyl), C(O)N(C$_{1-8}$alkyl)$_2$, NHC(O)NH$_2$, NHC(O)NH(C$_{1-8}$alkyl), NHC(O)N(C$_{1-8}$alkyl)$_2$, NHSO$_2$NH$_2$, NHSO$_2$NH(C$_{1-8}$alkyl), NHSO$_2$N(C$_{1-8}$alkyl)$_2$, SO$_2$NH$_2$, SO$_2$NH(C$_{1-8}$alkyl) or SO$_2$N(C$_{1-8}$alkyl)$_2$, and R$_4$ is selected from hydrogen, C$_{1-8}$alkyl, C$_{1-8}$alkyl(C$_{1-8}$alkoxy), C$_{1-8}$alkyl(halogen)$_{1-3}$, C$_{1-8}$alkyl(hydroxy), CO$_2$H, CO$_2$(C$_{1-8}$alkyl), COH, C(O)(C$_{1-8}$alkyl), hydroxy, C$_{1-8}$alkyl-NH$_2$, C$_{1-8}$alkyl-NH(C$_{1-8}$alkyl), C$_{1-8}$alkyl-N(C$_{1-8}$alkyl)$_2$, C$_{1-8}$alkyl(hydroxy)-NH(C$_{1-8}$alkyl), C$_{1-8}$alkyl(hydroxy)-N(C$_{1-8}$alkyl)$_2$, SO$_2$(C$_{1-8}$alkyl), C(O)NH$_2$, C(O)NH(C$_{1-8}$alkyl), C(O)N(C$_{1-8}$alkyl)$_2$, NHC(O)NH$_2$, NHC(O)NH(C$_{1-8}$alkyl), NHC(O)N(C$_{1-8}$alkyl)$_2$, NHSO$_2$NH$_2$, NHSO$_2$NH(C$_{1-8}$alkyl), NHSO$_2$N(C$_{1-8}$alkyl)$_2$, SO$_2$NH$_2$, SO$_2$NH(C$_{1-8}$alkyl) or SO$_2$N(C$_{1-8}$alkyl)$_2$.

An example of the invention includes a compound of Formula (Ia) and pharmaceutically acceptable forms thereof, wherein R$_2$ is selected from C$_{3-8}$cycloalkyl, aryl, heteroaryl, heterocyclyl or C$_{1-8}$alkyl substituted with C$_{3-8}$cycloalkyl, aryl, heteroaryl or heterocyclyl, optionally substituted on each of C$_{3-8}$cycloalkyl, aryl, heteroaryl and heterocyclyl with one or more of C$_{1-8}$alkyl, C$_{1-8}$alkoxy, —N—, —NHC(O)— or —C(O)—, wherein C$_{1-8}$alkyl and C$_{1-8}$alkoxy are each optionally substituted with one or more of C$_{1-8}$alkoxy, NH$_2$, NH(C$_{1-8}$alkyl), N(C$_{1-8}$alkyl)$_2$, NH(C$_{1-8}$alkyl-C$_{1-8}$alkoxy), N(C$_{1-8}$alkyl-C$_{1-8}$alkoxy)$_2$, nitro, cyano, halogen, hydroxy, C$_{3-8}$cycloalkyl, aryl, heteroaryl or heterocyclyl, optionally substituted on each of C$_{3-8}$cycloalkyl, aryl, heteroaryl and heterocyclyl with one or more of C$_{1-8}$alkyl, C$_{1-8}$alkoxy, C$_{1-8}$alkyl(C$_{1-8}$alkoxy), C$_{1-8}$alkyl(halogen)$_{1-3}$, C$_{1-8}$alkoxy(halogen)$_{1-3}$, C$_{1-8}$alkyl(hydroxy), C$_{1-8}$alkoxy(hydroxy), CO$_2$H, CO$_2$(C$_{1-8}$alkyl), COH, C(O)(C$_{1-8}$alkyl), NH$_2$, NH(C$_{1-8}$alkyl), N(C$_{1-8}$alkyl)$_2$, cyano, halogen, hydroxy, nitro, wherein N is substituted with two substituents each selected from hydrogen or C$_{1-8}$alkyl, and wherein NHC(O) and C(O) are each substituted on C(O) with C$_{1-8}$alkyl.

An example of the invention includes a compound of Formula (Ia) and pharmaceutically acceptable forms thereof, wherein R$_3$ is selected from hydrogen, C$_{1-8}$alkyl, C$_{1-8}$alkyl(C$_{1-8}$alkoxy), C$_{1-8}$alkyl(halogen)$_{1-3}$, C$_{1-8}$alkyl(hydroxy), CO$_2$H, CO$_2$(C$_{1-8}$alkyl), COH, C(O)(C$_{1-8}$alkyl), hydroxy, C$_{1-8}$alkyl-NH$_2$, C$_{1-8}$alkyl-NH(C$_{1-8}$alkyl), C$_{1-8}$alkyl-N(C$_{1-8}$alkyl)$_2$, C$_{1-8}$alkyl(hydroxy)-NH(C$_{1-8}$alkyl), C$_{1-8}$alkyl(hydroxy)-N(C$_{1-8}$alkyl)$_2$ or SO$_2$(C$_{1-8}$alkyl).

An example of the invention includes a compound of Formula (Ia) and pharmaceutically acceptable forms thereof, wherein R$_4$ is selected from hydrogen, C$_{1-8}$alkyl, C$_{1-8}$alkyl(halogen)$_{1-3}$, C$_{1-8}$alkyl(hydroxy), hydroxy, C$_{1-8}$alkyl-NH$_2$, C$_{1-8}$alkyl-NH(C$_{1-8}$alkyl) or C$_{1-8}$alkyl-N(C$_{1-8}$alkyl)$_2$.

An example of the invention includes a compound of Formula (Ia) and pharmaceutically acceptable forms thereof, wherein R$_2$ is selected from C$_{3-8}$cycloalkyl, aryl, heterocyclyl or C$_{1-8}$alkyl substituted with C$_{3-8}$cycloalkyl, optionally substituted on each of C$_{3-8}$cycloalkyl, aryl and heterocyclyl with one or more of C$_{1-8}$alkyl, C$_{1-8}$alkoxy, —N—, —NHC(O)— or —C(O)—, wherein C$_{1-8}$alkyl and C$_{1-8}$alkoxy are each optionally substituted with one or more of NH(C$_{1-8}$alkyl), N(C$_{1-8}$alkyl)$_2$, halogen, hydroxy or heterocyclyl, optionally substituted on heterocyclyl with one or more of C$_{1-8}$alkyl, wherein N is substituted with two substituents each selected from hydrogen or C$_{1-8}$alkyl, and wherein NHC(O) and C(O) are each substituted on C(O) with C$_{1-8}$alkyl;

$R_3$ is selected from hydrogen, $C_{1-8}$alkyl, $C_{1-8}$alkyl(hydroxy), C(O)($C_{1-8}$alkyl), $C_{1-8}$alkyl-NH($C_{1-8}$alkyl), $C_{1-8}$alkyl-N($C_{1-8}$alkyl)$_2$, $C_{1-8}$alkyl(hydroxy)-N($C_{1-8}$alkyl)$_2$ or SO$_2$($C_{1-8}$alkyl); and $R_4$ is selected from hydrogen or $C_{1-8}$alkyl.

Another example of the invention includes a compound of Formula (Ia), wherein $R_2$, $R_3$ and $R_4$ are selected from

| Cpd | $R_2$ | $R_3$ | $R_4$ |
|---|---|---|---|
| 1 | 4-[HO(CH$_2$)$_2$]-phenyl | H | H |
| 2 | 3,4,5-(CH$_3$O)$_3$-phenyl | H | H |
| 3 | phenyl | H | H |
| 4 | 4-[HO(CH$_2$)$_2$O]-phenyl | H | H |
| 5 | 4-CH$_3$O-phenyl | H | H |
| 6 | 3-CH$_3$O-phenyl | H | H |
| 7 | 2-CH$_3$O-phenyl | H | H |
| 8 | 2-CH$_3$-phenyl | H | H |
| 9 | 3-CH$_3$-phenyl | H | H |
| 10 | 4-CH$_3$-phenyl | H | H |
| 11 | 4-Cl-phenyl | H | H |
| 12 | 2-Cl-phenyl | H | H |
| 13 | cyclohexyl | H | H |
| 14 | cyclopentyl | H | H |
| 15 | cycloheptyl | H | H |
| 16 | cyclohexyl-CH$_2$ | H | H |
| 17 | 4-CH$_3$-cyclohexyl | H | H |
| 18 | (trans)-4-HO-cyclohexyl | H | H |
| 19 | 4-[pyrrolidin-1-yl-(CH$_2$)$_2$]-phenyl | H | H |
| 20 | 4-[piperazin-1-yl-(CH$_2$)$_2$]-phenyl | H | H |
| 21 | 4-[4-CH$_3$-piperazin-1-yl-(CH$_2$)$_2$]-phenyl | H | H |
| 22 | 4-[morpholin-4-yl-(CH$_2$)$_2$]-phenyl | H | H |
| 23 | 4-[(CH$_3$)$_2$N(CH$_2$)$_2$]-phenyl | H | H |
| 24 | 4-[(CH$_3$CH$_2$)$_2$N(CH$_2$)$_2$]-phenyl | H | H |
| 25 | 4-[CH$_3$NH(CH$_2$)$_2$]-phenyl | H | H |
| 26 | 4-[CH$_3$CH$_2$NH(CH$_2$)$_2$]-phenyl | H | H |
| 27 | 4-CH$_3$O-2-CH$_3$-phenyl | H | H |
| 28 | 2-Br-phenyl | H | H |
| 29 | 2-CF$_3$-phenyl | H | H |
| 30 | 2-HO-phenyl | H | H |
| 31 | 2-F-phenyl | H | H |
| 32 | 2-CH$_3$CH$_2$-phenyl | H | H |
| 33 | 2,4-(CH$_3$)$_2$-phenyl | H | H |
| 34 | -2,3-(CH$_3$)$_2$-phenyl | H | H |
| 35 | 2,6-(CH$_3$)$_2$-phenyl | H | H |
| 36 | -2,4-Cl$_2$-phenyl | H | H |
| 37 | 4-NH$_2$-phenyl | H | H |
| 38 | 4-(CH$_3$)$_2$N-phenyl | H | H |
| 39 | 4-HO-phenyl | H | H |
| 40 | 4-CH$_3$CH$_2$O-phenyl | H | H |
| 41 | 4-Br-2-CH$_3$-phenyl | H | H |
| 42 | (trans)-4-NH$_2$-cyclohexyl | H | H |
| 43 | 4-NH$_2$-cyclohexyl | H | H |
| 44 | 4-HO(CH$_2$)$_2$-2-CH$_3$-phenyl | H | H |
| 45 | 4-[CH$_3$NH(CH$_2$)$_2$]-2-CH$_3$-phenyl | H | H |
| 46 | 4-[(CH$_3$)$_2$N(CH$_2$)$_2$]-2-CH$_3$-phenyl | H | H |
| 47 | 4-[(CH$_3$CH$_2$)$_2$N(CH$_2$)$_2$]-2-CH$_3$-phenyl | H | H |
| 48 | 4-[pyrrolidin-1-yl-(CH$_2$)$_2$]-2-CH$_3$-phenyl | H | H |
| 49 | 4-[morpholin-4-yl-(CH$_2$)$_2$]-2-CH$_3$-phenyl | H | H |
| 50 | 4-[piperidin-1-yl-(CH$_2$)$_2$]-2-CH$_3$-phenyl | H | H |
| 51 | 4-[(4-CH$_3$-piperazin-1-yl)-(CH$_2$)$_2$]-2-CH$_3$-phenyl | H | H |
| 52 | 4-HO(CH$_2$)$_2$-2-Cl-phenyl | H | H |
| 53 | 4-[CH$_3$NH(CH$_2$)$_2$]-2-Cl-phenyl | H | H |
| 54 | 4-[(CH$_3$)$_2$N(CH$_2$)$_2$]-2-Cl-phenyl | H | H |
| 55 | 4-[(4-CH$_3$-piperazin-1-yl)-(CH$_2$)$_2$]-2-Cl-phenyl | H | H |
| 56 | 4-[morpholin-4-yl-(CH$_2$)$_2$]-2-Cl-phenyl | H | H |
| 57 | (trans)-4-NH$_2$-cyclohexyl | H | CH$_3$ |
| 58 | (2R)-bicyclo[2,2,1]hept-2-yl | H | H |
| 59 | (2S)-bicyclo[2,2,1]hept-2-yl | H | H |
| 60 | tetrahydro-pyran-4-yl | H | H |
| 61 | 1-CH$_3$-piperidin-4-yl | H | H |
| 62 | 4-NH$_2$-piperidin-1-yl | H | H |
| 63 | 4-[CH$_3$C(O)NH]-piperidin-1-yl | H | H |
| 64 | 1-[CH$_3$C(O)]-piperidin-4-yl | H | H |
| 65 | piperidin-4-yl | H | H |
| 66 | cyclohexyl | CH$_3$ | H |
| 67 | cyclohexyl | SO$_2$CH$_3$ | H |
| 68 | cyclohexyl | C(O)CH$_3$ | H |
| 69 | cyclohexyl | (CH$_2$)$_2$N(CH$_3$)$_2$ | H |
| 70 | cyclohexyl | (CH$_2$)$_2$OH | H |
| 71 | (trans)-4-HO-cyclohexyl | CH$_3$ | H |
| 72 | (trans)-4-HO-cyclohexyl | (CH$_2$)$_2$OH | H |
| 73 | (trans)-4-HO-cyclohexyl | (CH$_2$)$_2$NHCH$_3$ | H |
| 74 | (trans)-4-HO-cyclohexyl | (CH$_2$)$_2$N(CH$_3$)$_2$ | H |
| 75 | (trans)-4-CH$_3$O-cyclohexyl | H | H |
| 76 | (trans)-4-HO-cyclohexyl | CH$_2$CH(OH)—CH$_2$N(CH$_3$)$_2$ | H |
| 77 | (trans)-4-HO(CH$_2$)$_2$-cyclohexyl | H | H |
| 78 | (trans)-4-CH$_3$NH(CH$_2$)$_2$-cyclohexyl | H | H |
| 79 | 4-HO-2-CH$_3$-phenyl | H | H |
| 80 | 4-CH$_3$NH(CH$_2$)$_2$O-2-CH$_3$-phenyl | H | H |
| 81 | 4-(CH$_3$)$_2$N(CH$_2$)$_2$O-2-CH$_3$-phenyl | H | H |

An example of the present invention includes a compound selected from:

Cpd 1

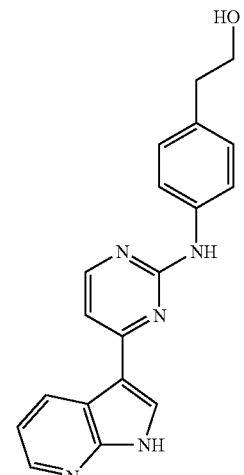

Cpd 2

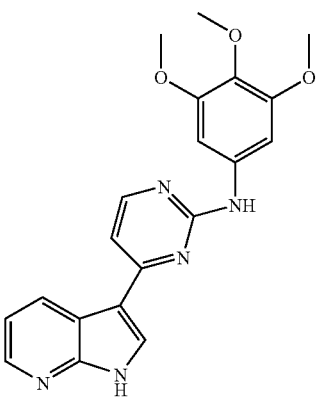

-continued
Cpd 3
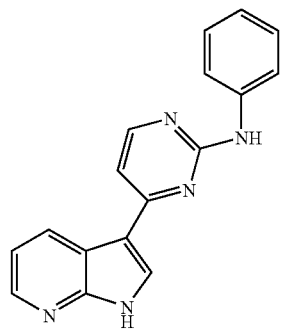
Cpd 4
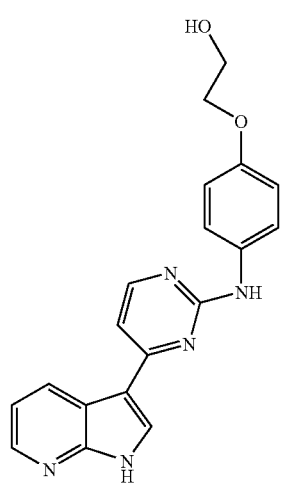
Cpd 5
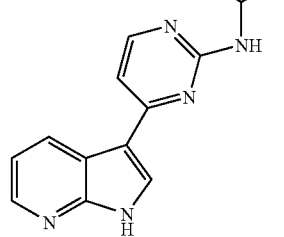
Cpd 6
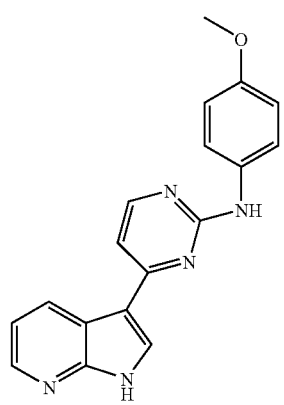
-continued
Cpd 7
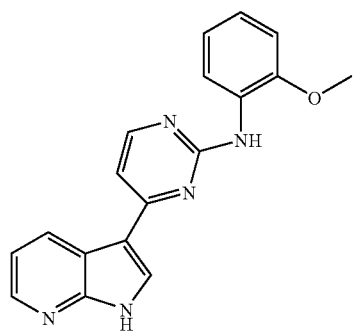
Cpd 8
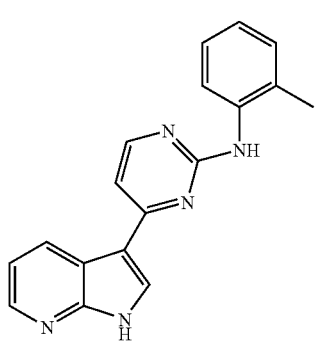
Cpd 9
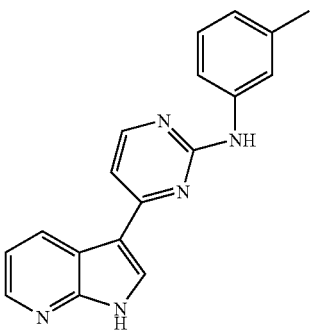
Cpd 10
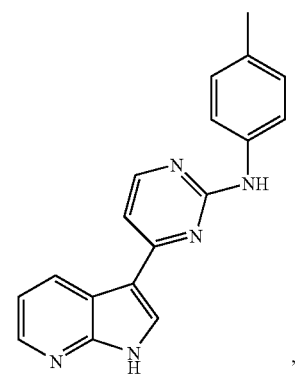

-continued
Cpd 11
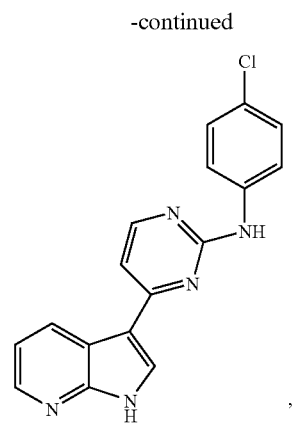
Cpd 12
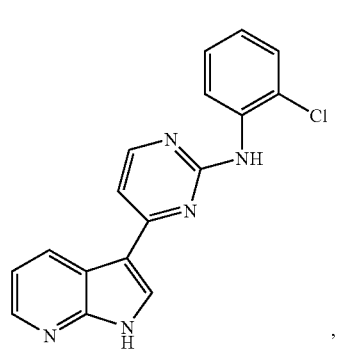
Cpd 13
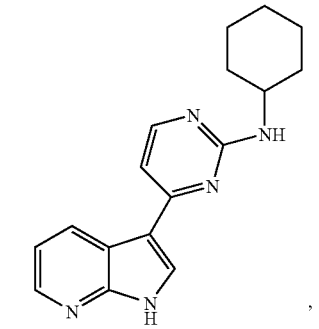
Cpd 14
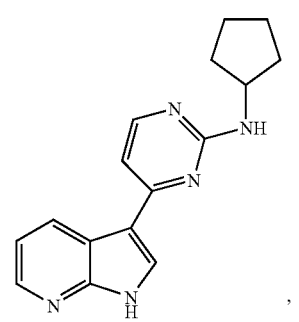
-continued
Cpd 15
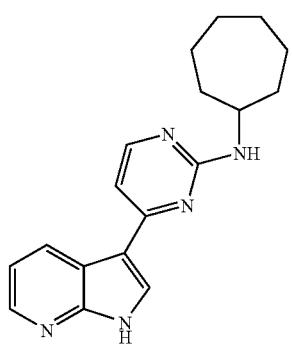
Cpd 16
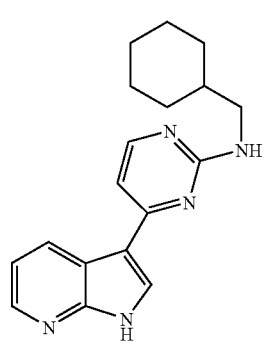
Cpd 17
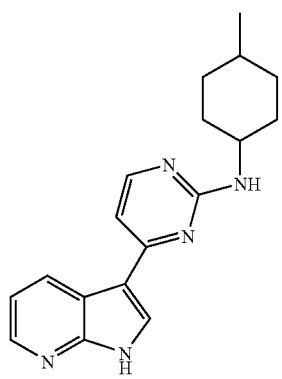
Cpd 18
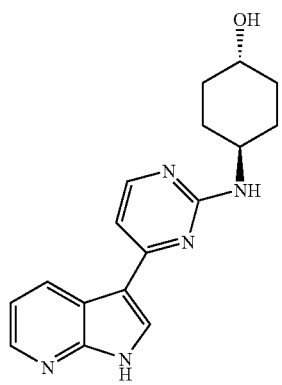

-continued
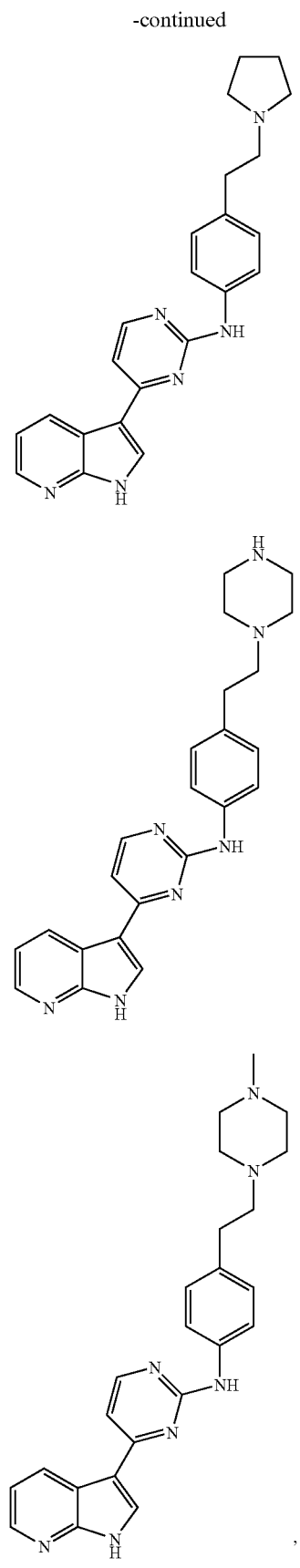
Cpd 19
Cpd 20
Cpd 21
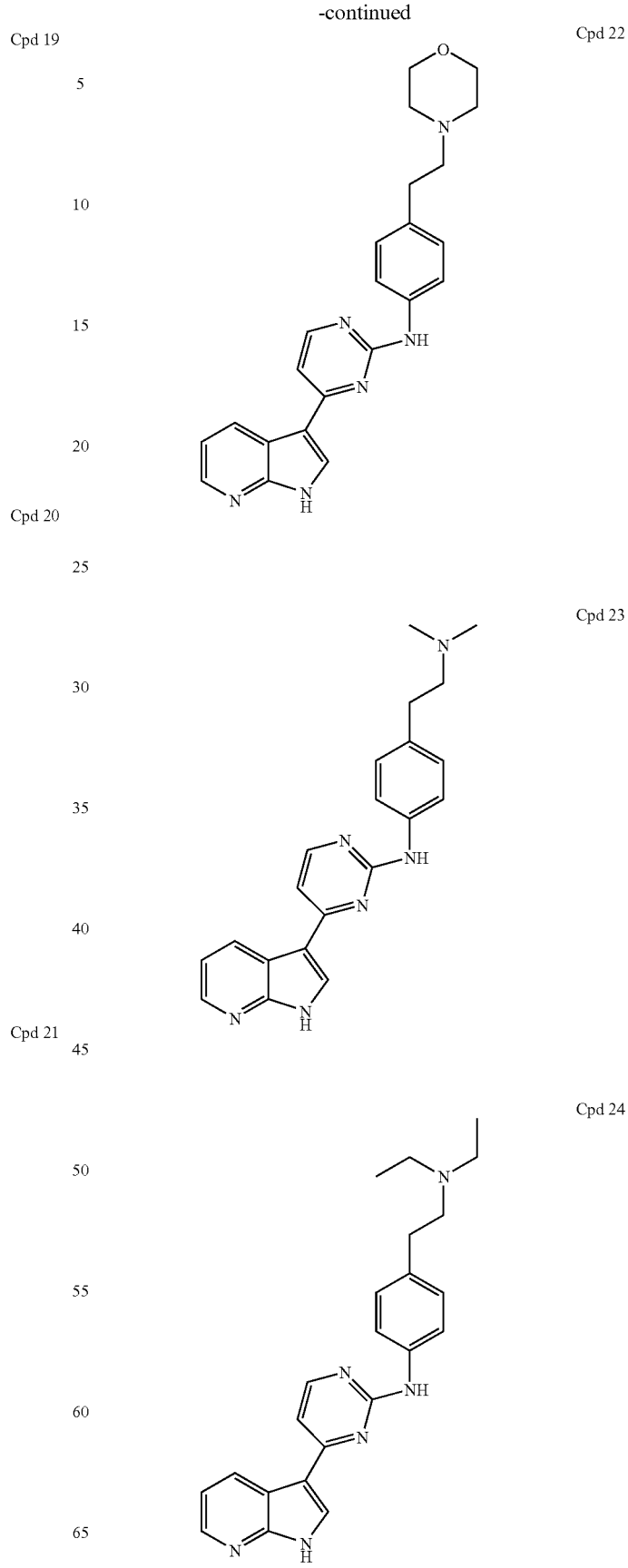
Cpd 22
Cpd 23
Cpd 24

Cpd 25
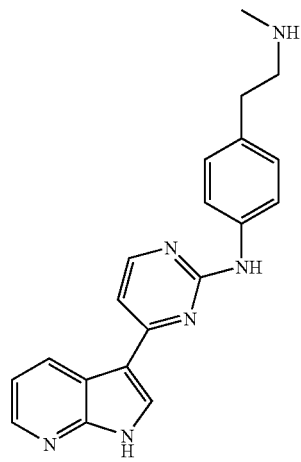
Cpd 26
Cpd 27
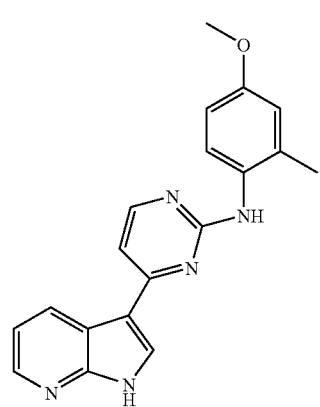
Cpd 28
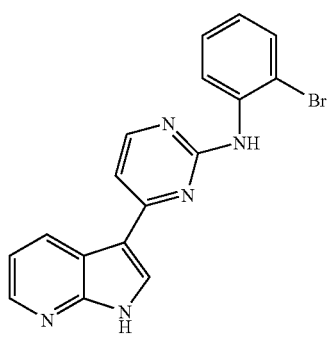
Cpd 29
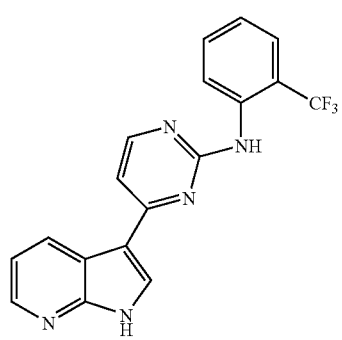
Cpd 30
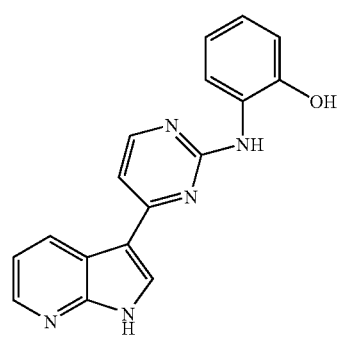
Cpd 31
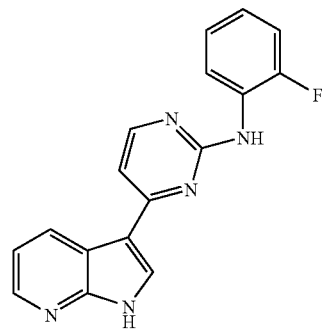

-continued
Cpd 32
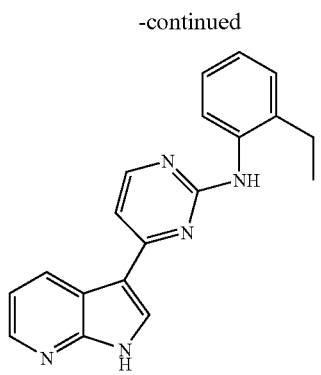
Cpd 33
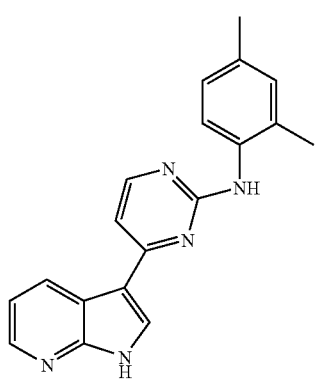
Cpd 34
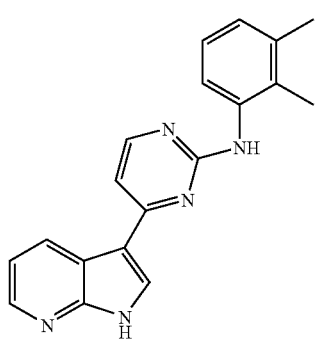
Cpd 35
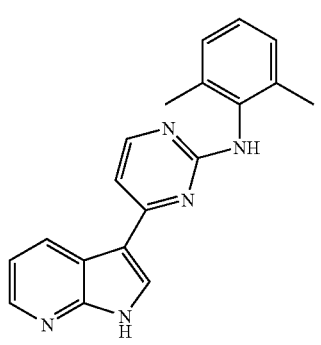
-continued
Cpd 36
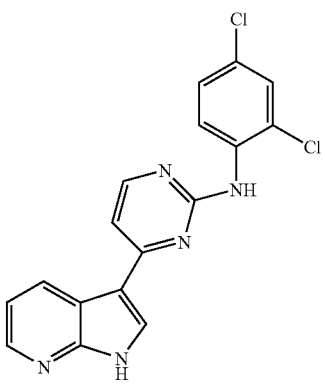
Cpd 37
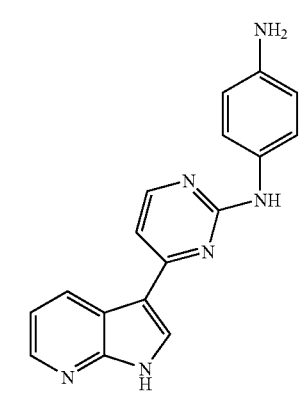
Cpd 38
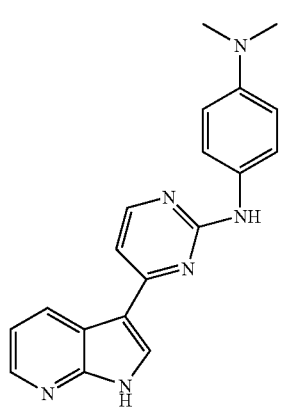
Cpd 39
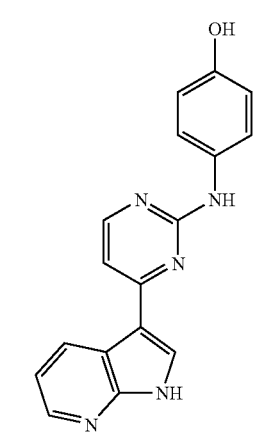

Cpd 40
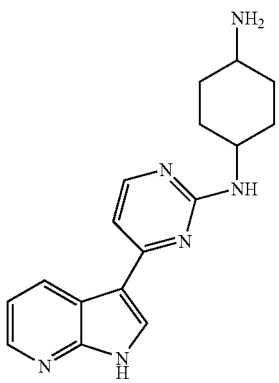
Cpd 41
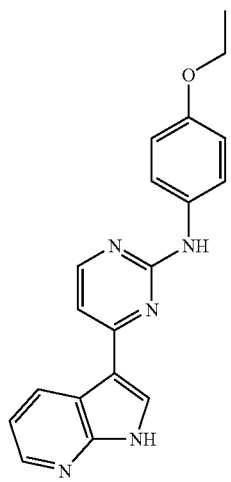
Cpd 42
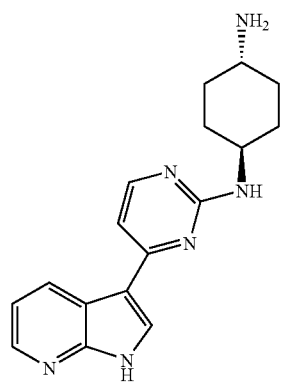
Cpd 43
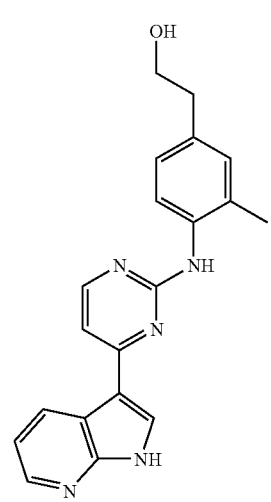
Cpd 44
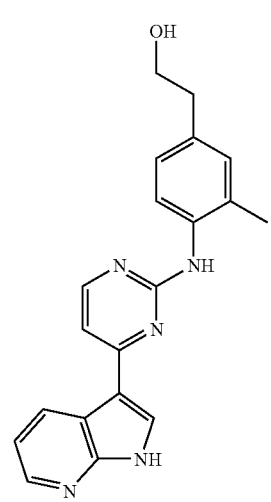
Cpd 45
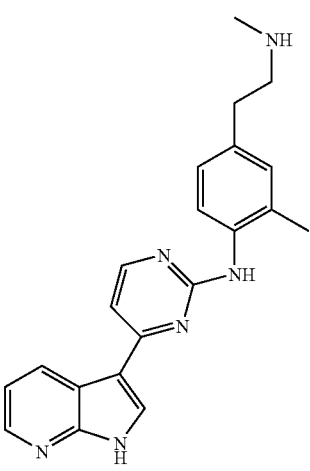

-continued
Cpd 46
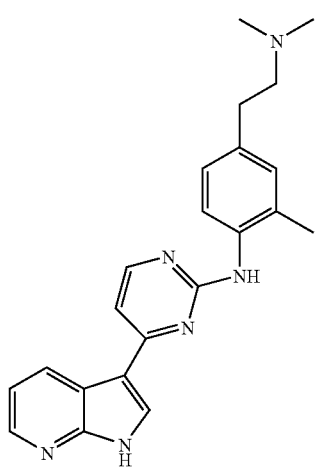
Cpd 47
Cpd 48
-continued
Cpd 49
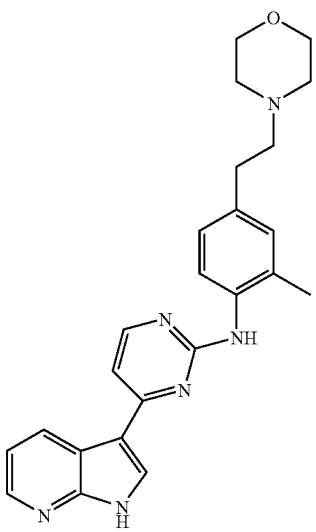
Cpd 50
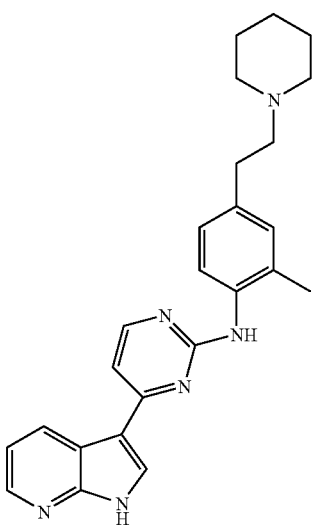
Cpd 51
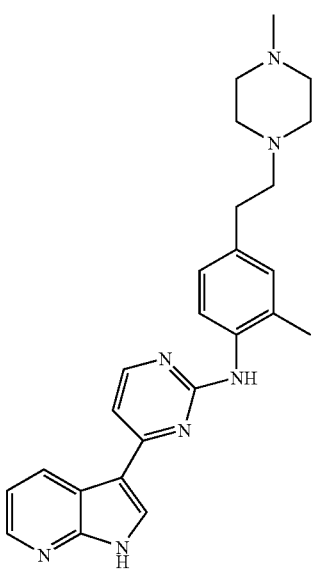

-continued
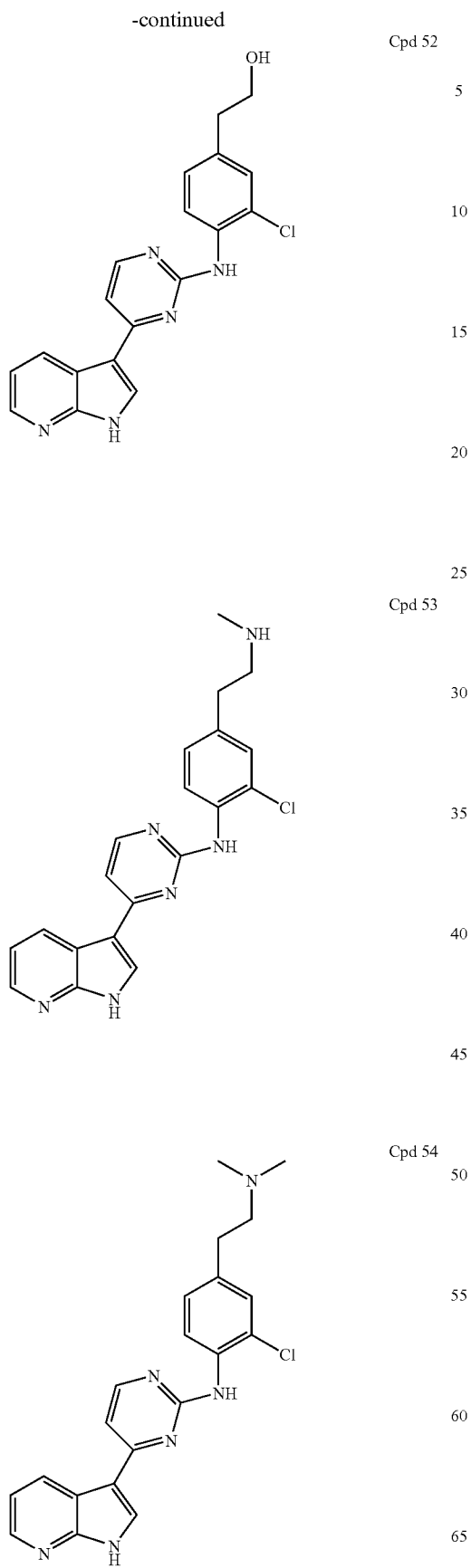
Cpd 52
Cpd 53
Cpd 54
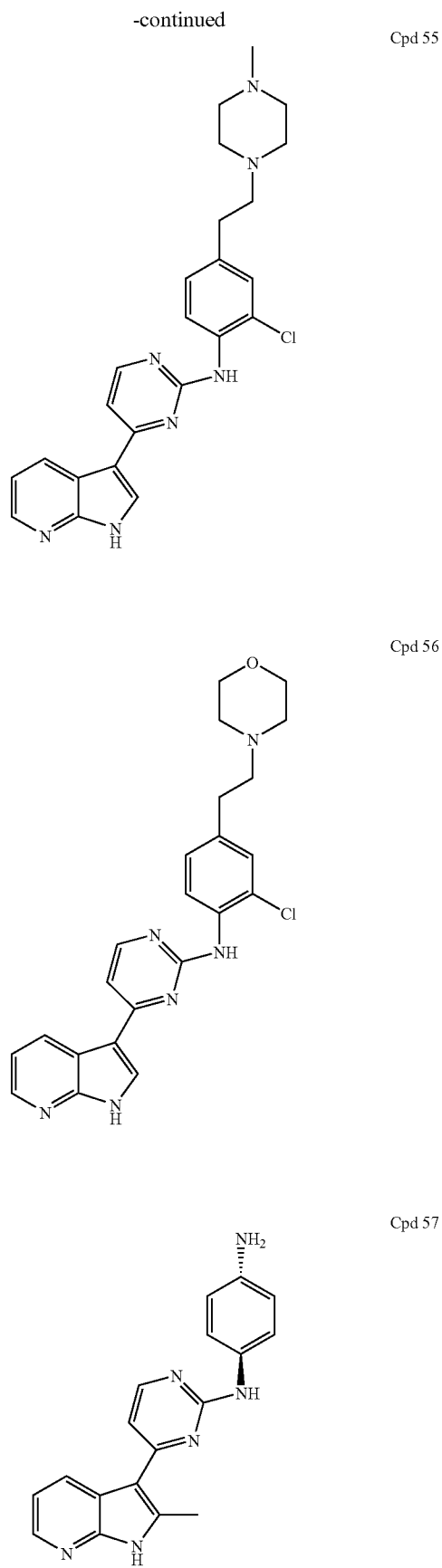
Cpd 55
Cpd 56
Cpd 57

-continued
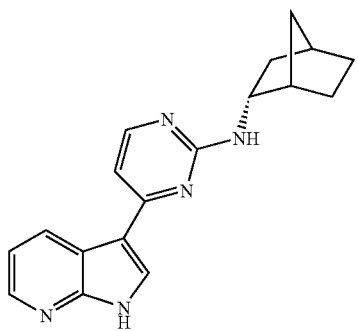
Cpd 58
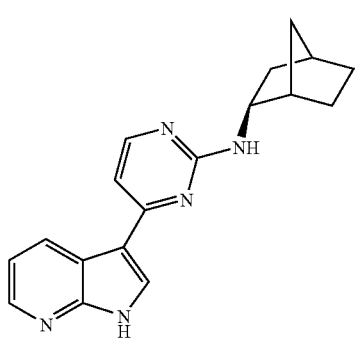
Cpd 59
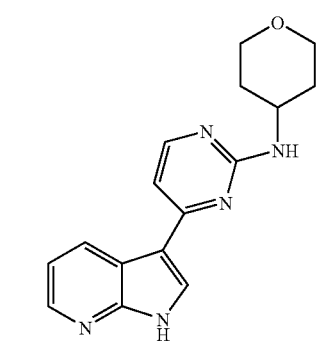
Cpd 60
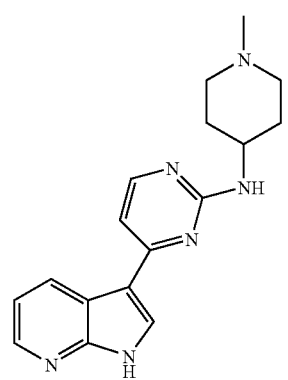
Cpd 61
-continued
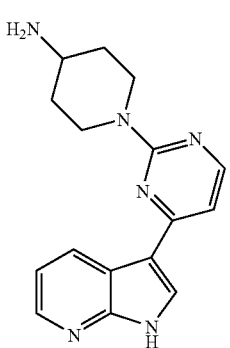
Cpd 62
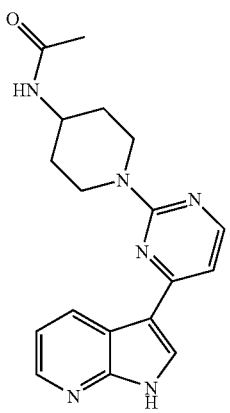
Cpd 63
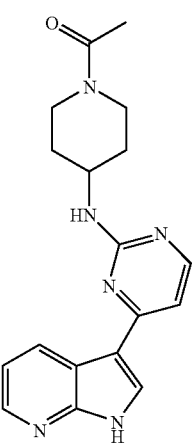
Cpd 64
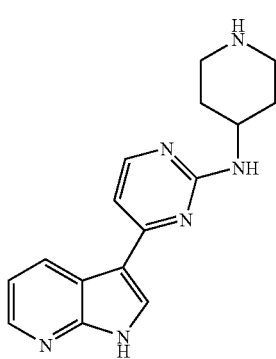
Cpd 65

-continued
Cpd 66
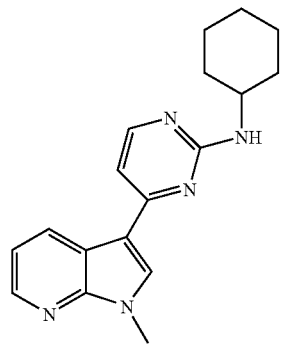
Cpd 67
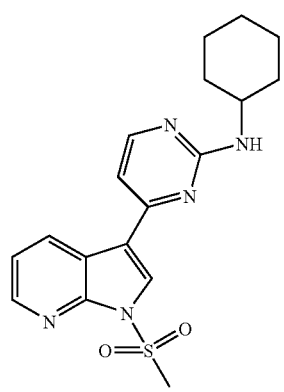
Cpd 68
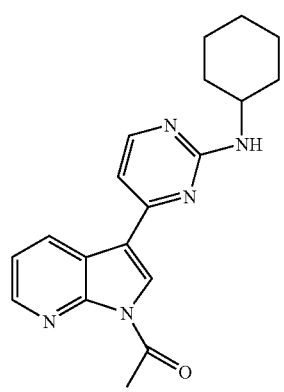
Cpd 69
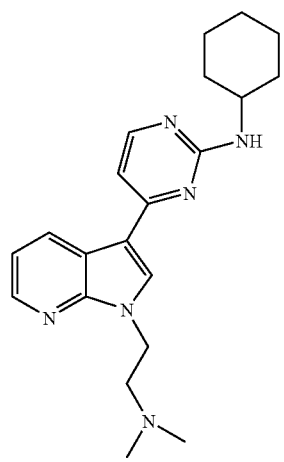
-continued
Cpd 70
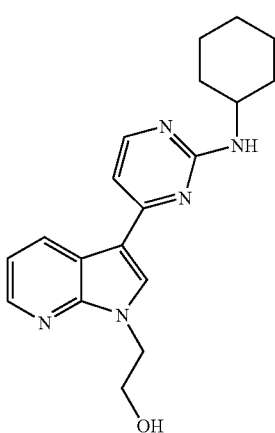
Cpd 71
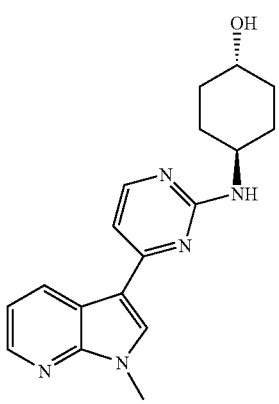
Cpd 72
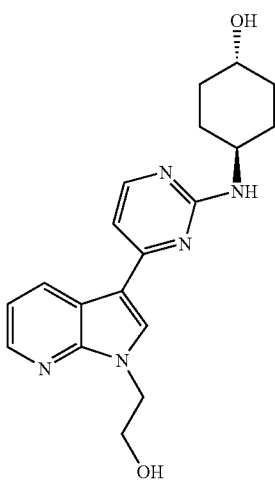

-continued
Cpd 73
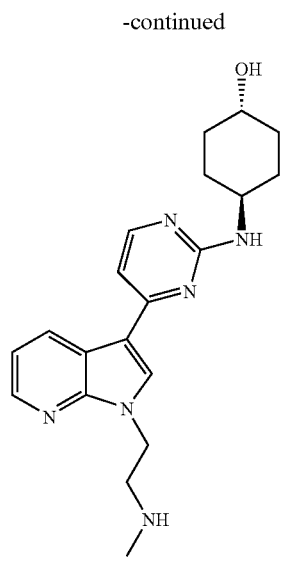
Cpd 74
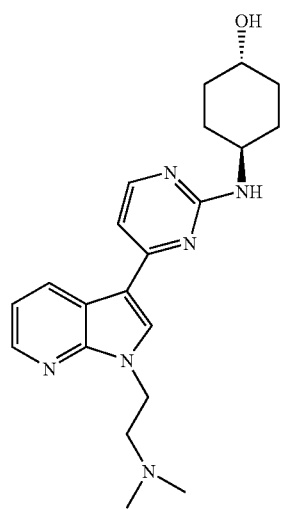
Cpd 75
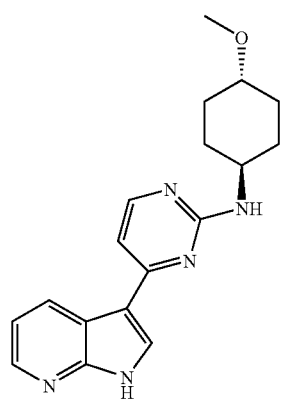
-continued
Cpd 76
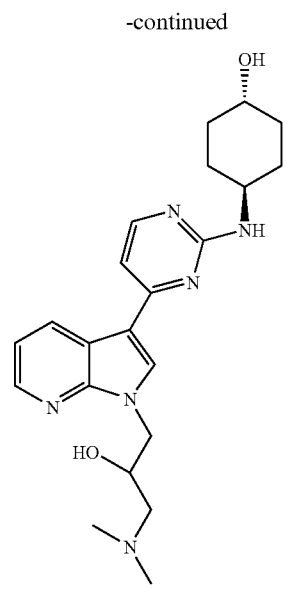
Cpd 77
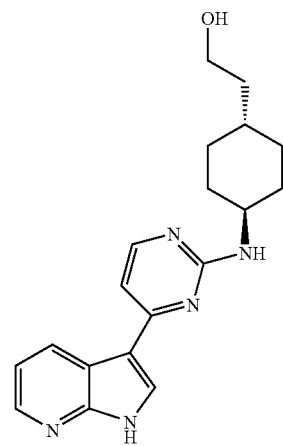
Cpd 78
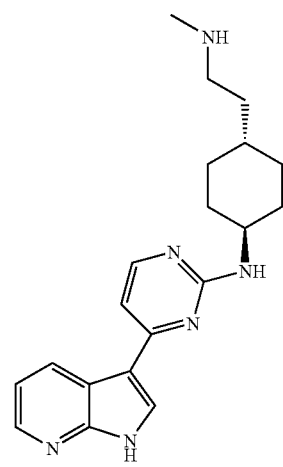

-continued

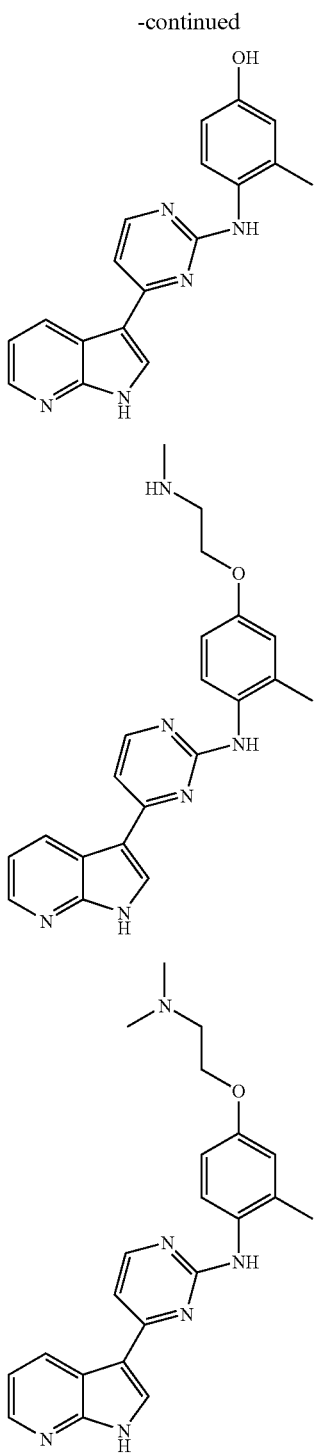

Cpd 79

Cpd 80

Cpd 81

An example of the present invention is a pyrimidinyl substituted fused-pyrrolyl compound of Formula (I), wherein the compound is a CDK, VEGF-R2 kinase, HER2 kinase, Aurora-A kinase, or RET receptor kinase inhibitor.

The present invention provides a method for using compounds of Formula (I) in treating or ameliorating a kinase receptor-mediated disorder.

An example of the method includes inhibiting unregulated kinase activity comprising contacting the kinase domain with one or more compounds of Formula (I).

An example of the method includes inhibiting a kinase by contacting the kinase receptor with a compound of Formula (I)

An example of the method includes inhibiting increased or unregulated kinase expression or signaling leading to unregulated cell proliferation comprising contacting a kinase receptor with one or more compounds of Formula (I).

An embodiment of the invention is a pyrimidinyl substituted 7-azaindolyl compound of Formula (I), wherein the compound is a CDK, VEGF-R2 kinase, HER2 kinase, Aurora-A kinase, or RET receptor kinase inhibitor.

The present invention also provides a method for using the pyrimidinyl substituted fused-pyrrolyl compounds of Formula (I) in treating or ameliorating a CDK, VEGF-R2 kinase, HER2 kinase, Aurora-A kinase, or RET receptor kinase mediated disorder.

An embodiment of the invention is a method for using a pyrimidinyl substituted 7-azaindolyl compound of Formula (1) for treating or ameliorating a CDK, VEGF-R2 kinase, HER2 kinase, Aurora-A kinase, or RET receptor kinase mediated disorder.

An example of the method includes inhibiting a cyclin dependent kinase by contacting the kinase receptor with a compound of Formula (I).

An example of the method includes inhibiting the unregulated expression of a cyclin dependent kinase and the like.

An embodiment of the invention is a method for inhibiting a kinase selected from the group consisting of CDK, VEGF-R2 kinase, HER2 kinase, Aurora-A kinase and RET kinase by contacting the kinase receptor with a compound of Formula (I).

An embodiment of the invention is a method for treating or ameliorating a kinase mediated disorder in a subject in need thereof comprising administering to the subject an effective amount of a compound of Formula (D).

Another embodiment of the invention is a method for treating or ameliorating a CDK, VEGF-R2 kinase, HER2 kinase, Aurora-A kinase, or RET receptor kinase mediated disorder in a subject in need thereof comprising administering to the subject an effective amount of a compound of Formula (I) for treating or ameliorating a CDK, VEGF-R2 kinase, HER2 kinase, Aurora-A kinase, or RET receptor kinase mediated disorder.

Chemical Definitions

As used herein, the following terms have the following meanings:

The term "$C_{1-8}$alkyl," whether used alone or as part of a substituent group, means a saturated branched or straight chain monovalent hydrocarbon radical or alkyldiyl linking group having a specified number of carbon atoms, wherein the radical is derived by the removal of one hydrogen atom from a single carbon atom and the alkyldiyl linking group is derived by the removal of one hydrogen atom from each of two carbon atoms in the chain. The term "$C_{1-8}$alkyl" refers to a radical having from 1-8 carbon atoms in a linear or branched arrangement. Typical alkyl radicals include, but are not limited to, methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Embodiments include, e.g., the alkyl groups $C_{1-8}$alkyl or $C_{1-4}$alkyl. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{2-8}$alkenyl," whether used alone or as part of a substituent group, means an alkyl radical having at least one carbon-carbon double bond, wherein the radical is derived by the removal of one hydrogen atom from a single carbon atom. Typical alkenyl radicals include, but are not limited to, ethenyl, propenyl, allyl (2-propenyl), butenyl, pentenyl, hexenyl and the like. Embodiments include, e.g., the alkenyl groups $C_{2-8}$alkenyl or $C_{2-4}$alkenyl. As described above, an alkenyl radical may be similarly attached to a core molecule and further substituted where indicated.

The term "$C_{2-8}$alkynyl," whether used alone or as part of a substituent group, means an alkyl radical having at least one carbon-carbon triple bond, wherein the radical is derived by the removal of one hydrogen atom from a single carbon atom. Typical alkynyl radicals include, but are not limited to, ethynyl, propynyl, butynyl, pentynyl, hexynyl and the like. Embodiments include, e.g., the alkynyl groups $C_{2-8}$alkynyl or $C_{2-4}$alkynyl. As described above, an alkynyl radical may be similarly attached to a core molecule and further substituted where indicated.

The term "$C_{1-8}$alkoxy," whether used alone or as part of a substituent group, means an alkyl or alkyldiyl alcohol radical derived by the removal of the hydrogen atom from the hydroxide oxygen portion of the alcohol radical. Typical embodiments include, e.g., the alkoxy groups $C_{1-8}$alkoxy or $C_{1-4}$alkoxy. For example, "$C_{1-8}$alkoxy" specifically includes the radicals methoxy, ethoxy, propoxy, butoxy, pentoxy, hexoxy, heptoxy, octoxy and the like. As described above, an alkoxy radical may be similarly attached to a core molecule and further substituted where indicated.

The term "$C_{3-8}$cycloalkyl," whether used alone or as part of a substituent group, means a saturated or partially unsaturated cyclic hydrocarbon ring system. Typical cycloalkyl radicals include, but are not limited to, cyclopropyl, cyclobutyl, cyclopentyl and cyclohexyl.

The term "heterocyclyl," whether used alone or as part of a substituent group, means a saturated or partially unsaturated cyclic ring radical derived by the removal of one hydrogen atom from a single carbon atom of the ring system and in which one or more ring carbon atoms are a heteroatom selected from N, O, S, SO or $SO_2$. Embodiments include monocyclic or bicyclic rings wherein 1, 2, 3 or 4 members of the ring are a nitrogen atom, or 0, 1, 2 or 3 members of the ring are nitrogen atoms and 1 member is an oxygen or sulfur atom. Typical heterocyclyl radicals include, and are not limited to, dihydro-1H-pyrrole (including 2-pyrrolinyl or 3-pyrrolinyl), pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, pyran, tetrahydropyranyl, tetrahydrothiopyranyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furyl, tetrahydro-thienyl, tetrahydropyranyl, tetrahydro-pyridazinyl, 1,3-benzodioxol-5-yl, 2,3-dihydro-1,4-benzodioxin-6-yl and the like.

The term "aryl," whether used alone or as part of a substituent group, means an unsaturated cyclic ring radical derived by the removal of one hydrogen atom from a single carbon atom of the ring system. Typical aryl radicals include, and are not limited to, phenyl, naphthalenyl, fluorenyl, indenyl, azulenyl, anthracenyl, biphenyl and the like.

The term "heteroaryl," whether used alone or as part of a substituent group, means an unsaturated cyclic ring radical derived by the removal of one hydrogen atom from a single carbon atom of the ring system and in which one or more ring carbon atoms are a heteroatom selected from N, O, S, SO or $SO_2$. Typical heteroaryl radicals include, and are not limited to, furyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzoxazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "substituted" means the independent replacement of one or more hydrogen atoms within a radical with that amount of substitutents allowed by available valences.

The term "dependently substituted" means that the substituents are specified in an indicated combination of structure variables.

In general, IUPAC nomenclature rules are used throughout this disclosure.

Pharmaceutical Preparations & Methods of Use

Pharmaceutical compositions according to the invention may, alternatively or in addition to a compound of Formula (I), comprise as an active ingredient a pharmaceutically acceptable salt of a compound of Formula (I), (Ia) or (Ib) or an ester, prodrug or pharmaceutically active metabolite of such a compound or salt.

A compound of Formula (I) as an active ingredient further includes a radio-labeled compound of Formula (I), whereby at least one hydrogen atom of the compound of Formula (D) is replaced with a deuterium or tritium atom. Other labeling techniques known to those skilled in the arts may also be used.

"Composition(s)" refers to a product containing one or more compounds of Formula (I) or a form thereof (such as a product comprising the specified ingredients in the specified amounts, as well as any product which results, directly or indirectly, from such combinations of the specified ingredients in the specified amounts).

"Pharmaceutically acceptable" refers to molecular entities and components used herein which are of sufficient purity and quality such that, when appropriately administered to an animal or a human, the composition does not produce an adverse, allergic or other untoward reaction. Accordingly, a pharmaceutically acceptable composition or medicament for either human use (clinical and over-the-counter) or veterinary use are equally included within the scope of the present invention.

The compounds of the present invention may be present in the form of salts. For use in medicines, a salt form for a compound of this invention refers to acidic/anionic or basic/cationic salt forms.

Suitable salt forms include acid addition salts which may, for example, be formed by mixing a solution of the compound according to the invention with a solution of an acid such as hydrochloric acid, sulphuric acid, fumaric acid, maleic acid, succinic acid, acetic acid, benzoic acid, citric acid, tartaric acid, carbonic acid, phosphoric acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate, trichloroacetate, trifluoroacetate and the like.

Compositions in accordance with the invention inhibit the kinase activity of CDK, VEGF-R2 kinase, HER2 kinase, Aurora-A kinase, or RET receptor kinase or kinase complexes.

Preferred compositions of the invention contain compounds having an inhibition constant against a CDK, VEGF-R2 kinase, HER2 kinase, Aurora-A kinase, or RET receptor kinase of about 25 μM or less, more preferably of about 10 μM or less, even more preferably of about 1 μM or less, and most preferably of about 0.5 μM or less.

Certain compounds of Formula (I), (Ia) or (Ib) may exist in various stereoisomeric or tautomeric forms. The present invention encompasses all such CDK, VEGF-R2 kinase, HER2 kinase, Aurora-A kinase, or RET receptor kinase inhibiting compounds, including active compounds in the form of essentially pure enantiomers, racemic mixtures, pure geometric isomers (such as cis and trans stereoisomers), tautomers, isomers or equilibrated mixtures thereof.

The present invention indeed contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers, or enantiomers).

The term "stereoisomer" refers to isomers of identical constitution that differ in the arrangement of their atoms in space. Enantiomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superimposable. The term "diastereomer" refers to stereoisomers that are not related as mirror images. The symbols "R" and "S" represent the configuration of substituents around a chiral carbon atom(s). The symbols "R*" and "S*" denote the relative configurations of substituents around a chiral carbon atom(s). Where the compounds of the present application have at least one stereocenter, they accordingly exist as enantiomers. Where the compounds according to the present invention posses two or more stereocenters, they may additionally exist as diastereoisomers. It is to be understood that all such isomers and mixtures thereof are encompassed within the scope to the present invention.

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

The invention also relates to the compounds in different crystalline forms, polymorphic or amorphous forms and (an) hydrous forms and as such are intended to be included in the scope of the invention. In addition, some of the compounds may form solvates with water (i.e., hydrates) or common organic solvents, and such are also intended to be encompassed within the scope of this invention. It is well known within the pharmaceutical industry that chemical compounds may be isolated in any of such forms by slightly changing the method of purification and/or isolation from the solvents used in the synthetic preparation of such compounds.

The term "prodrug" refers to a metabolic precursor of a compound of Formula (I) (or a salt thereof), that is pharmaceutically acceptable. A prodrug is a functional derivative of a compound which may be inactive when administered to a subject but is converted in vivo to an active metabolite compound.

The term "active metabolite" refers to a metabolic product of a compound that is pharmaceutically acceptable and effective for preventing, treating or ameliorating a chronic or acute kinase mediated disease. Conventional procedures for the selection and preparation of suitable prodrug derivatives are described, for example, in "Design of Prodrugs", ed. H. Bundgaard, Elsevier, 1985.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art.

Therapeutic Use

The compounds of the present invention are CDK, VEGF-R2 kinase, HER2 kinase, Aurora-A kinase, or RET receptor kinase inhibitors useful in a method for treating or ameliorating a CDK, VEGF-R2 kinase, HER2 kinase, Aurora-A kinase, or RET receptor kinase mediated disorder.

The present invention provides a method for treating or ameliorating a kinase mediated disorder in a subject in need thereof comprising administering to the subject an effective amount of a compound of Formula (I).

The present invention further provides a method for treating or ameliorating a CDK, VEGF-R2 kinase, HER2 kinase, Aurora-A kinase, or RET receptor kinase mediated disorder in a subject in need thereof comprising administering to the subject an effective amount of a compound of Formula (I) for treating or ameliorating a CDK, VEGF-R2 kinase, HER2 kinase, Aurora-A kinase, or RET receptor kinase mediated disorder.

Examples of the method of the present invention include treating or ameliorating a CDK, VEGF-R2 kinase, HER2 kinase, Aurora-A kinase, or RET receptor mediated disorder.

Many conventional cytotoxic cancer therapies destroy the rapidly dividing epithelium of the hair follicle and induce alopecia (hair loss). Inhibition of CDK, VEGF-R2 kinase, HER2 kinase, Aurora-A kinase, or RET receptor kinases during conventional chemotherapy may represent a therapeutic strategy for prevention of chemotherapy-induced alopecia by arresting the cell cycle and reducing the sensitivity of epithelial cells to antitumor agents (Davis S. T., et al., Prevention of chemotherapy-induced alopecia in rats by CDK inhibitors, *Science,* 2001, (Jan 5), 291, 5501, 25-6).

Accordingly, to be useful in a method for the prevention of chemotherapy-induced alopecia, a CDK, VEGF-R2 kinase, HER2 kinase, Aurora-A kinase, or RET receptor inhibitor compound would have to be cytostatic rather than cytotoxic and be able to hold the cell in a stationary growth phase, thus protecting a hair follicle from the cytotoxic activity of a conventional chemotherapeutic agent being administered at the same time. In this way, topical application of non-apoptotic CDK, VEGF-R2 kinase, HER2 kinase, Aurora-A kinase, or RET receptor kinase inhibitors represents a potentially useful approach for the prevention of chemotherapy-induced alopecia in cancer patients.

Although coronary angioplasty is a highly effective procedure used to reduce the severity of coronary occlusion, its long-term success is limited by a high rate of restenosis. Vascular smooth muscle cell activation, migration and proliferation is largely responsible for restenosis following angioplasty (Ross, R., *Nature,* 1993, 362, 801-809). Recent studies have shown that CDK2 is activated very early after endothelial denudation in a rat carotid artery model of restenosis (Wei, G. L., et al., *Circ. Res.,* 1997, 80, 418-426). Therefore, antiproliferative therapies targeted to CDK other kinases such as a VEGF-R2 kinase, HER2 kinase, Aurora-A kinase, or RET receptor kinase or other components of the cell cycle machinery may be a suitable approach to treat these disorders. One aspect for use of the compounds of the present invention is a method for the treatment or amelioration of restenosis wherein a CDK, VEGF-R2 kinase, HER2 kinase, Aurora-A kinase, or RET receptor kinase inhibitor is impregnated on the surface of an angioplasty balloon or stent, thus targeting drug delivery to the local environment where endothelial and smooth muscle cell proliferation are the leading cause of vascular occlusion following an initial angioplasty and restenosis in the area of a stent's implantation (Eric E. Brooks, Nathanael S. Gray, Alison Joly, Suresh S. Kerwar, Robert Lum, Richard L. Mackman, Thea C. Norman, Jose Rosete, Michael Rowe, Steven R. Schow, Peter G. Schultz, Xingbo Wang, Michael M. Wick and Dov Shiffman, CVT-313, a Specific and Potent Inhibitor of CDK2 That Prevents Neointimal Proliferation, *J. Biol. Chem.,* 1997, 272(46):29207-29211).

An embodiment of the present invention includes a prophylactic and therapeutic method for treating or ameliorating a CDK, VEGF-R2 kinase, HER2 kinase, Aurora-A kinase, or RET receptor kinase mediated disorder in a subject in need thereof comprising administering to the subject an effective amount of a compound of Formula (I) or composition thereof. In an embodiment of the invention, the mediated kinase is a CDK, VEGF-R2 kinase, HER2 kinase, Aurora-A kinase, or RET receptor kinase.

The effective amount of the compounds of Formula (I) exemplified in such a method is from about 0.001 mg/kg/day to about 300 mg/kg/day:

"Subject" means an animal, preferably a mammal, most preferably a human, who is a patient or has been the object of treatment, observation or experiment and is at risk of (or susceptible to) developing a disease or disorder or having a disease or disorder related to unregulated kinase activity.

"Effective amount" means that amount of active compound or pharmaceutical agent that will result in improved healing, prevention, improvement treatment, or a decrease in the rate of advancement of a disease or disorder or amelioration of a disease, disorder, or side effect. The term also indicates the amount that could effectively enhance physiological function.

Another aspect of the present invention includes the use of a compound of Formula (I) for the preparation of a medicament for preventing, treating or ameliorating a CDK, VEGF-R2 kinase, HER2 kinase, Aurora-A kinase, or RET receptor kinase mediated disorder in a subject in need thereof.

"Medicament" refers to one or more compounds of Formula (I) or a form thereof used in a product for use in preventing, treating or ameliorating a chronic or acute kinase mediated disease.

"Administering," with respect to the methods of the present invention, refers to a means for treating, ameliorating or preventing a disease as described herein with a compound specifically disclosed or a compound or prodrug thereof, which would obviously be included within the scope of the invention albeit not specifically disclosed for certain of the instant compounds.

In accordance with the method of the present invention, an individual compound of the present invention or a composition or medicament thereof can be administered at different times during the course of therapy or concurrently in divided or single combination forms.

Such methods further include administering an effective amount of one or more compounds of Formula (I) or a form, composition or medicament thereof with one or more agents at different times during the course of a therapy or concurrently in a combination form.

Prophylactic administration can occur prior to the manifestation of symptoms characteristic of a CDK, VEGF-R2 kinase, HER2 kinase, Aurora-A kinase, or RET receptor kinase associated disease or disorder such that the disease or disorder is prevented or, alternatively, delayed in its progression. The instant invention is therefore to be understood as embracing all such regimes of simultaneous or alternating treatment and the term "administering" is to be interpreted accordingly.

The term "kinase mediated disorder" as used herein, includes, and is not limited to disorders and diseases associated with kinase overactivity and conditions that accompany such diseases. Kinase overactivity includes unregulated cellular mitosis, unregulated cell proliferation and upregulated kinase activity. Disorders and diseases associated with unregulated cell proliferation include cancers (including solid tumors and leukemias such as glioma cancers, epidermoid cancers, head and neck cancers, lung cancers, breast cancers, colorectal cancers, prostate cancers, gastric cancers, esophageal cancers, papillocarcinomas, Kaposi's sarcoma, leukemias and lymphomas), and associated pathologies such as abnormal cell proliferation, unregulated cell proliferation, tumor growth, tumor vascularization, as well as metastatic cancer cell invasion and migration, angiopathy, angiogenesis, and chemotherapy-induced alopecia.

Disorders and diseases associated with unregulated cellular mitosis, unregulated cell proliferation and upregulated kinase activity include, without limitation, acute inflammation, chronic inflammation, osteoarthritis, synovial pannus invasion in arthritis, multiple sclerosis, myasthenia gravis, diabetes mellitus, diabetic angiopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, papilloma formation, psoriasis, dermatitis, eczema, seborrhea, central nervous system diseases, Alzheimer's disease, Parkinson's disease, depression, heart disease, hemangioma atheroma, occular diseases, macular degeneration, diseases of the cornea, glaucoma, autoimmune disease, viral infections, cytomegalovirus, atherosclerosis, transplantation-induced vasculopathies, neointima formation, allergic-asthma, lung fibrosis, pulmonary fibrosis, chronic obstructive pulmonary disorder, acute, subacute or chronic forms of glomerulonephritis, glomerulosclerosis, congenital multicystic renal dysplasia, kidney fibrosis, diabetic retinopathy, rheumatoid arthritis and arterial restenosis.

The term "upregulated kinase activity" refers to either 1) increased or unregulated kinase activity or expression, 2) increased kinase expression leading to unwanted cell proliferation, or 3) mutations leading to constitutive activation of the kinase receptor. The existence of an inappropriate or abnormal level or activity of the kinase receptor is determined by procedures well known in the art.

The term "disorders and diseases associated with unregulated cell proliferation" refers to disorders wherein unwanted cell proliferation of one or more subset of cells in a multicellular organism occurs resulting in harm (such as discomfort or decreased life expectancy) to the multicellular organism.

Such cell proliferative disorders can occur in different types of animals and humans and include, but are not limited to, cancers (glioma, lung, breast, colorectal, prostate, gastric and esophageal, leukemias and lymphomas), atherosclerosis, restenosis, psoriasis, papilloma, pulmonary fibrosis, in-stent stenosis, vascular graft restinosis, glomerular nephritis, diabetic retinopathy and rheumatoid arthritis.

Another aspect of the present invention includes a method for inhibiting a cell's unregulated entry into mitosis comprising administering to the cell an effective amount of a compound of Formula (I) or composition thereof for inhibiting CDK, VEGF-R2 kinase, HER2 kinase, Aurora-A kinase, or RET receptor kinase activity in the cell.

Another aspect of the present invention includes a method for inhibiting unregulated cell proliferation in a tumor comprising administering to the tumor an effective amount of a compound of Formula (I) or composition thereof for inhibiting CDK, VEGF-R2 kinase, HER2 kinase, Aurora-A kinase, or RET receptor kinase activity in the tumor.

Another aspect of the present invention includes a method for down-regulating CDK, VEGF-R2 kinase, HER2 kinase, Aurora-A kinase, or RET receptor kinase activity in a cell comprising administering to the cell an effective amount of a compound of Formula (I) or composition thereof for down-regulating CDK, VEGF-R2 kinase, HER2 kinase, Aurora-A kinase, or RET receptor kinase activity in the cell.

Another aspect of the present invention includes a method for treating or ameliorating chemotherapy induced alopecia in a subject in need thereof comprising topically administering to the subject a therapeutically effective amount of a compound of Formula (I) or composition thereof.

In the cancer therapeutic field it is common to use a combination of different treatments to cure cancer patients. Therefore, the antiproliferative activity defined herein could be used as a sole therapy or may involve one or more other substances and/or treatments. Such combinational treatment may be achieved by the simultaneous, sequential or separate administration of the individual components. The other component(s) for these conjoint treatments in addition to the antiproliferation therapy defined above may include surgery, radiotherapy or chemotherapy.

Another aspect of the present invention includes a method for use of a compound of Formula (I) or composition thereof advantageously administered in one or more cell anti-proliferation therapies including chemotherapy, radiation therapy, gene therapy or immunotherapy for preventing, treating or ameliorating a kinase mediated disorder.

The term "radiation therapy" refers to a therapy that comprises exposing the patient in need thereof to radiation. The present invention includes a method for administering one or more compounds of Formula (I) or a form, composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

The combination therapy is selected from, e.g., 1) co-administration of a compound of Formula (I) or composition thereof and a chemotherapeutic agent for preventing, treating or ameliorating a kinase mediated disorder, 2) sequential administration of a compound of Formula (I) or composition thereof and a chemotherapeutic agent for preventing, treating or ameliorating a kinase mediated disorder, 3) administration of a composition containing a compound of Formula (I) and a chemotherapeutic agent for preventing, treating or ameliorating a kinase mediated disorder, or, 4) simultaneous administration of a separate composition containing a compound of Formula (I) and a separate composition containing a chemotherapeutic agent for preventing, treating or ameliorating a kinase mediated disorder.

For example, the compounds of this invention may be useful in combination therapies with a chemotherapeutic agent for the treatment of a number of different cancers and advantageously may facilitate the use of a reduced dose of the chemotherapeutic agent that is recommended for a particular cancer or cell proliferation disorder. Therefore, it is contemplated that the compounds of this invention can be used during or after treatment with a particular chemotherapeutic agent.

The term "chemotherapeutic agent" refers to chemotherapeutic agents used to treat a kinase mediated cancer or antiviral agents used to treat cytomegalovirus and includes, and is not limited to, anti-angiogenic agents, anti-tumor agents, cytotoxic agents, inhibitors of cell proliferation, and the like or mixtures thereof.

The term "treating or ameliorating" includes, and is not limited to, facilitating the eradication of, inhibiting the progression of or promoting stasis of a malignancy.

Such chemotherapy may cover three main categories of therapeutic agent:

1. Cell cycle specific chemotherapeutic agents including, but not limited to, epipodophyllotoxins (e.g. etoposide and teniposide); diterpenoids (e.g. paclitaxel and docetaxel); vinca alkaloids (e.g. vincristine, vindesine, vinblastine, and vinorelbine); antimetabolites (e.g. cladrabine, cytarabine, allopurinol, fludurabine, methotrexate, mercaptopurine, thioguanine, 5-fluorouracin and fluorodeoxyuridine) and camptothecins (e.g. 9-amino camptothecin, topotecan and irinotecan).

2. Cytotoxic chemotherapeutic agents including, but not limited to, alkylating agents (e.g. hexamethylmelamine, busulfan, melphalan, chlorambucil, cyclophosphamide, mechlorethamine, carmustine, lomustine, dacarbazine, carboplatin, displatin and oxaliplatin); antitumor antibiotics (e.g. bleomycin, idarubicin, mitomycin-c, doxorubicin, daunomycin, epirubicin, dactinomycin and mithramycin);

3. Other anticancer agents including, but not limited to, testosterone 5α-dihydroreductase inhibitors (e.g. finasteride); anti-estrogens (e.g. tamoxifen, toremifent, raloxifene, droloxifene and iodoxyfene); progestrogens (e.g. megestrol acetate); aromatase inhibitors (e.g. anastrozole, letrazole, vorazole, and exemestane; antiandrogens (e.g. flutamide, nilutamide, bicalutamide, and cytorterone acetate); LHRH agonists and antagonists (e.g. goserelin acetate and luprolide); metalloproteinase inhibitors (e.g. marimastat); urokinase plasminogen activator receptor function inhibitors; cyclioxygenase type 2 inhibitors (e.g. celecoxib); angiogenesis inhibiting agents such as VEGFR and TIE-2 inhibitors; growth factor function inhibitors such as inhibitors of hepatocyte growth factor; erb-B2, erb-B4, epidermal growth factor receptor (e.g. Iressa and Tarceva), platelet derived growth factor receptor, vascular endothelial growth factor receptor and TIE-2; and other tyrosine kinase inhibitors other than those described in the present invention. Most commonly used drug moiety is selected from taxanes including paclitaxel and docetaxelcamptothecin, doxorubicin, bohemine, methotrexate, platinum-based therapies including cisplatin, oxaliplatin, caiboplatin, topoisomerase inhibitors including etoposide and topotecan and podophyllotoxin.

Another aspect of the present invention includes a method for administering a compound of the present invention in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

Pharmaceutical Compositions

An embodiment of the present invention includes a composition comprising an admixture of one or more compounds of Formula (1) and/or one or more forms thereof and one or more excipients.

The present invention further includes the use of a process for making the composition or medicament comprising mixing one or more of the instant compounds and an optional carrier; and, includes those compositions or medicaments resulting from such a process.

Pharmaceutical formulations may be prepared by any of the conventional and unconventional pharmaceutical methods well known in the pharmacy art and may be adapted for administration by any appropriate route, for example by the oral (including buccal or sublingual), topical (including buccal, sublingual or transdermal), vaginal or parental (including subcutaneous, intramuscular or intradermal) route, rectal, nasal and the like.

Formulations for oral administration may be presented as capsules or tablets; powders or granules; solutions or suspensions in aqueous or non-aqueous liquids; oil-in-water liquid emulsions or water-in-oil liquid emulsion, edible foams or whips. Formulations for topical administration may be presented as ointments, creams, suspensions, lotions, powders, solutions, pastes, gels, sprays, aerosols or oils. Formulations for transdermal administration may be presented as discrete patches intended to remain in intimate contact with the epidermis of the recipient for a prolonged period of time. Formulations for rectal administration may be presented as suppositories or as enemas. Formulations for nasal administration may be presented as a nasal spray or as nasal drops, include aqueous or oil solutions of the active ingredient or a coarse powder having a particle size for in the range 20 to 500 microns. Formulations for inhalation may be presented as fine particle dusts or mists, which may be generated by means of various types of metered, dose pressurized aerosols, nebulizers or insufflators. Formulations for vaginal administration may be presented as pessaries, tampons, creams, gels, pastes, forms or spray formulations. Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compounds of the present invention or their pharmaceutically acceptable salts can also be administered through liposome delivery systems, such as small unilamellar vesicles, large unilamellar vesicles and multilamellar vesicles. Liposomes could be formed from a variety of phospholipids, such as stearylamine, phosphatidylcholine, or cholesterol.

The compounds of the present invention or their pharmaceutically acceptable salts can also be delivered by using monoclonal antibodies as carriers. The compounds may also be coupled with soluble polymers as targetable drug carriers. Such polymers can include polyvinylpyrrolidone, pyran copolymer, polyhydroxypropylmethacryl-amidephenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polyactic acid, polepsilon caprolactone, polyhydroxy butyric acid, polyorthoesters, polyacetals, polydihydropyrans, polycyanoacrylates and cross-linked or amphipathis block copolymers of hydrogels.

The dosage unit (tablet, capsule, powder, injection, suppository, teaspoonful and the like) containing the pharmaceutical compositions herein will contain an amount of the active ingredient necessary to deliver a therapeutically effective amount as described above.

The composition may contain from about 0.001 mg to about 5000 mg (preferably, from about 0.01 to about 500 mg) of the active compound or prodrug thereof and may be constituted into any form suitable for the mode of administration selected for a subject in need. A contemplated therapeutically effective amount may range from about 0.001 mg to about 300 mg/kg of body weight per day. Preferably, the range is from about 0.03 to about 100 mg/kg of body weight per day. Most preferably, the range is from about 0.05 to about 15 mg/kg of body weight per day. The compounds may be administered according to a dosage regimen of from about 1 to about 5 times per day.

Pharmaceutical formulations may be displayed as unit dose forms containing a predetermined amount of active ingredient per unit dose. Such a unit dose may contain 1 mg to 700 mg of a compound of the present invention depending on the condition being treated, the route of administration.

For oral administration, the compositions are preferably provided in the form of tablets containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

General Synthetic Methods

Representative compounds of the present invention can be synthesized in accordance with the general synthetic methods described below, which are illustrated more particularly in the schemes that follow. The invention should not be construed as being limited by the chemical reactions and conditions expressed. The preparation of the various starting materials used in the schemes is well within the skill of persons versed in the art.

The terms used in describing the invention are commonly used and known to those skilled in the art. As used herein, the following abbreviations have the indicated meanings:

| | |
|---|---|
| Cpd | compound |
| DCM | dichloromethane |
| DMF | N,N-dimethylformamide |
| DMSO | dimethyl sulfoxide |
| min | minute |
| h/hr/hrs | hour(s) |
| NBS | N-bromosuccinimide |
| TEA or Et$_3$N | triethylamine |
| THF | tetrahydrofuran |

Scheme I describes the preparation of chloride substituted Compound I.

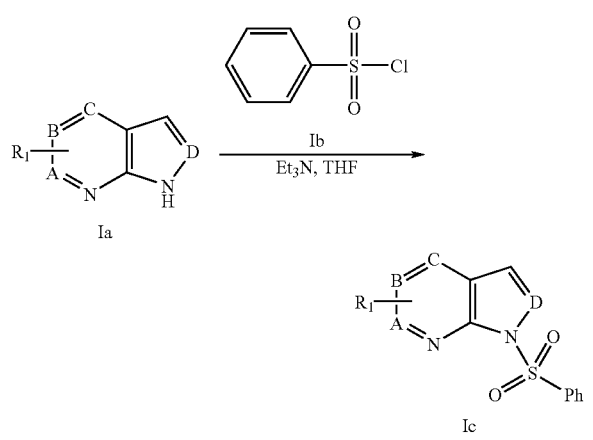

7-Azaindole Compound Ia was protected by reaction with phenylsulfonyl Compound Ib to provide a 1-benzenesulfonyl protected bicyclic pyrrolyl Compound Ic.

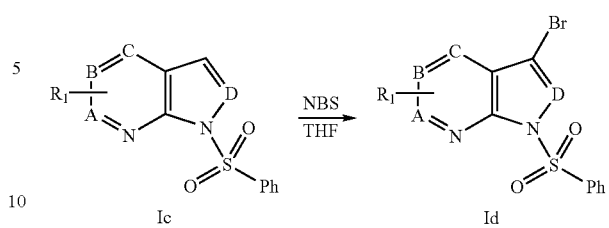

Compound Ic was brominated at C-3 by reaction with NBS in THF to generate a 1-benzenesulfonyl-3-bromo substituted bicyclic pyrrolyl Compound Id.

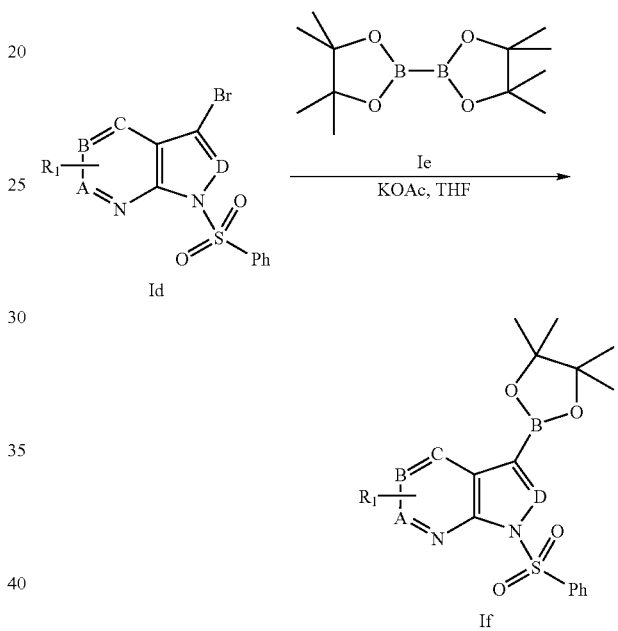

Compound Id was reacted with a 4,4,5,5,4',4',5',5'-octamethyl-[2,2']bi[[1,3,2]-dioxaborolanyl] Compound Ie in the presence of [1,1'-bis(diphenylphosphino)-ferrocene]dichloropalladium(II) and KOAc to provide a 1-benzenesulfonyl-3-(4,4,5,5-tetramethyl-[1,3,2]dioxaborolan-2-yl) substituted bicyclic pyrrolyl Compound If.

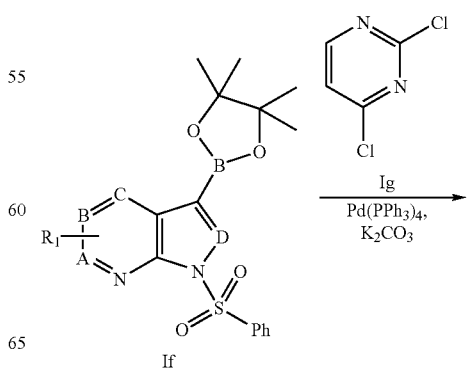

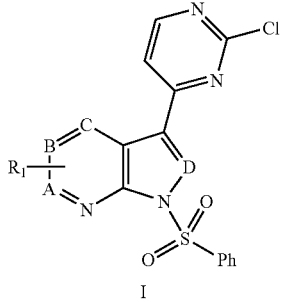

Compound If was reacted with a 2,4-dichloropyrimidine Compound Ig to generate a protected intermediate pyrimidinyl substituted bicyclic pyrrolyl Compound I.

Scheme II

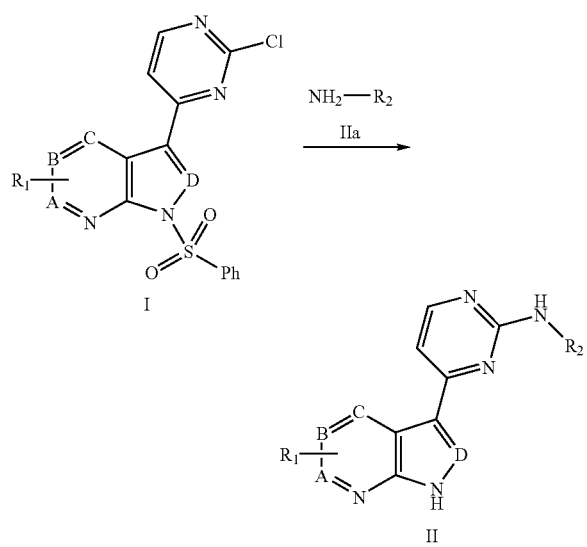

The protected intermediate Compound I was reacted with a solution of an amino substituted Compound IIa at a temperature of 120° C. 2 equivalents of amine Compound IIa were dissolved in a solvent such as DMF, 2-methoxyethanol or mixtures thereof to provide a substituted pyrimidin-4-yl bicyclic pyrrolyl Compound II.

Scheme III

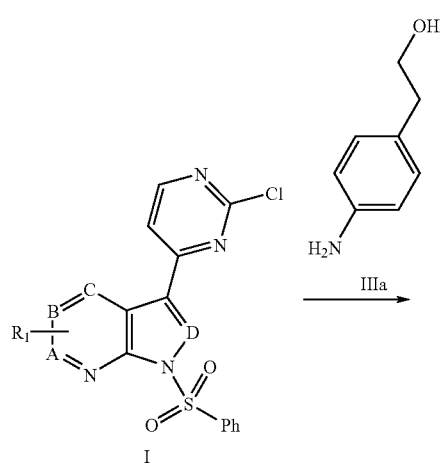

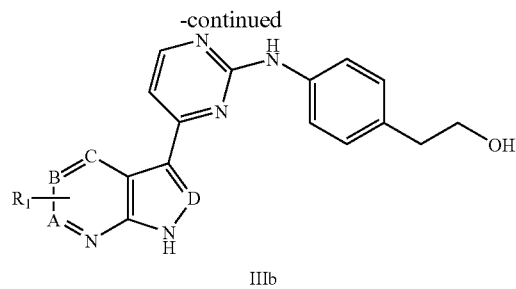

Using the procedure of Scheme II, the protected intermediate Compound I was reacted with a solution of a 2-(4-aminophenyl)ethanol Compound IIIa to provide an amino phenyl ethanol substituted pyrimidin-4-yl bicyclic pyrrolyl Compound IIIb.

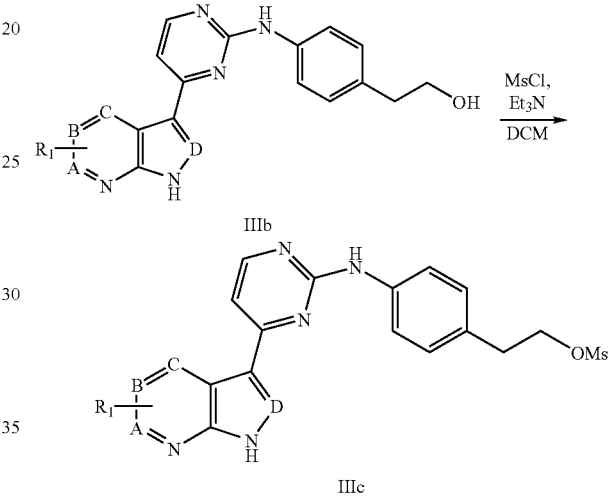

Compound IIIb was carried forward and reacted with an aryl or alkyl sulfonate leaving group such as MsCl (methanesulfonyl chloride) and the like in a solution of Et$_3$N (tri ethyl amine) in DCM to provide Compound IIIc.

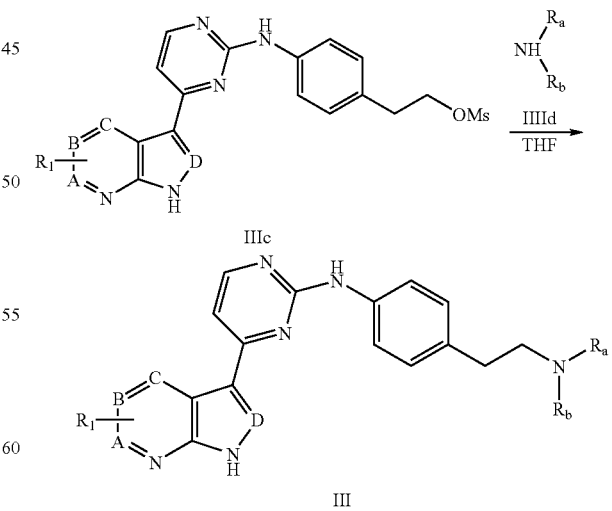

Compound IIIc was reacted with ~2-3 equivalents of amine Compound IIId in TRF at 60-70° C. overnight to provide the Compound III, wherein R$_a$ and R$_b$ is each C$_{1-8}$alkyl or are taken together to form an optionally substituted heterocyclyl.

Scheme IV

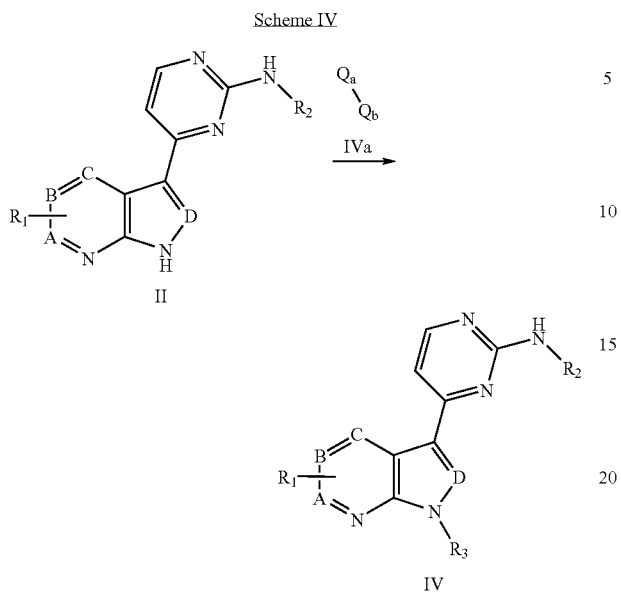

Compound II is reacted with a Compound IVa to provide a Compound IV of formula (I), wherein the $Q_a$ portion of Compound IVa is a leaving group and the $Q_b$ portion of Compound IVa represents $R_3$ or a functional derivative of $R_3$ that may be deprotected to provide additional compounds representative of the present invention.

Specific Synthetic Methods

Specific compounds which are representative of this invention were prepared as per the following examples and reaction sequences. The examples and the diagrams depicting the reaction sequences are offered by way of illustration to aid in the understanding of the invention and should not be construed in any way to limit the invention. The depicted intermediates may also be used in subsequent examples to produce additional compounds of the present invention. No attempt has been made to optimize the yields obtained in any of the reactions.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ES) were recorded on a Hewlett Packard 59987A spectrometer. High resolution mass spectra (HRMS) were obtained on a Micromass Autospec. E spectrometer by fast atom bombardment (FAB) technique.

EXAMPLE 1

2-{4-[4-(1H-Pyrrolo[2,3-b]pyridin-3-yl)-pyrimidin-2-ylamino]-phenyl}-ethanol (1)

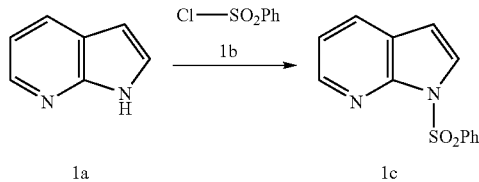

Benzenesulfonyl chloride (1b) (98.7 g) was added dropwise into a solution of 7-azaindole (1a) (60.0 g) and triethylamine (56.6 g) in DCM (500 mL) at 0° C. The mixture was warmed to rt and stirred for 2 days to produce a white crystalline product. The white crystals were filtered off and the solution was washed with a saturated aqueous NaHCO$_3$ solution and brine, then dried over MgSO$_4$ and concentrated. The residue was recrystallized in ethyl acetate (200 mL) to provide N-phenylsulfonyl-7-azaindole (1c) (121.31 g, 94%) as white crystals. $^1$H NMR (400 MHz, CDCl$_3$) δ 8.43 (d, J=4.8 Hz, 1H), 8.18 (d, J=8.0 Hz, 2H), 7.85 (d, J=8.0 Hz, 1H), 7.73 (d, J=4.8 Hz, 1H), 7.57 (t, J=7.6 Hz, 1H), 7.48 (t, J=7.6 HZ, 2H), 7.15 (dd, J=8.0 Hz, 4.8 Hz, 1H), 6.58 (d, J=4.8 Hz, 1H).

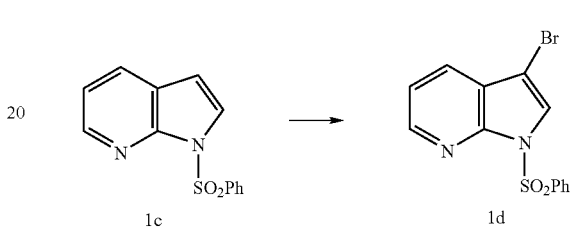

Potassium carbonate (47.1 g) was added to a solution of N-phenylsulfonyl-7-azaindole (1c) (80.0 g) in THF (500 mL) at 0° C. N-Bromosuccinamide (60.6 g) was then added portionwise to the suspension. The reaction mixture was warmed to rt and stirred for 2 days. It was quenched with water and the mixture was extracted with ethyl acetate. The combined organic phase was washed with brine, then dried over Na$_2$SO$_4$ and concentrated. The residue was subjected to silica gel column (eluted with 7:3 dichloromethane/hexane) to give 1-benzenesulfonyl-3-bromo-1H-pyrrolo[2,3-b]pyridine (1d) (50.78 g, 49%). $^1$H NMR (400 MHz, CDCl$_3$) δ 8.43 (d, J=4.8 Hz, 1H), 8.20 (d, J=8.0 Hz, 2H), 7.82 (d, J=8.0 Hz, 1H), 7.78 (s, 1H), 7.62 (t, J=7.6 Hz, 1H), 7.50 (t, J=7.6 HZ, 2H), 7.26 (m, 1H).

MS (ESI) m/z: 337 (M+H)$^+$.

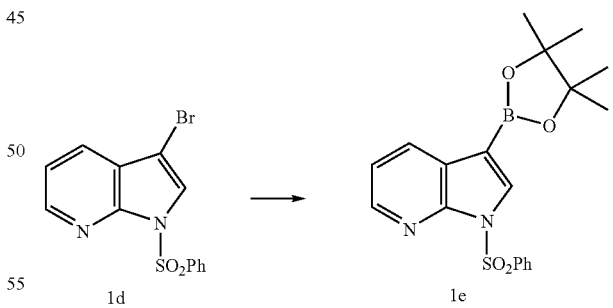

A mixture of compound Ed (50.78 g), bis(pinacolato)diboron (42.22 g), [1,1'-bis(diphenylphosphino)ferrocene]dichloropalladium(II) (1:1 complex with dichloromethane, 12.32 g) and potassium acetate (44.46 g) in THF (300 mL) was refluxed for 24 hrs. The reaction was quenched with water and extracted with ethyl acetate. The combined organic phase was concentrated and the residue was purified on silica gel column (eluted with 100% dichloromethane and 2% methanol in dichloromethane) to provide 1-benzenesulfonyl- 3-(4,4,5,5-tetramethyl-[1,3,2]dioxaborolan-2-yl)-1H-pyrrolo[2,3-b]pyridine (1e) (22.10 g, 38%) as a white solid. $^1$H NMR (400 MHz, CDCl$_3$) δ 8.42 (d, J=4.8 Hz, 1H), 8.21 (m, 3H), 8.15 (s, 1H), 7.57 (t, J=7.6 Hz, 1H), 7.48 (t, J=7.6 HZ, 2H), 7.35 (dd, J=8.0 Hz, 4.8 Hz, 1H). MS (ESI) m/z: 385 (M+H)$^+$.

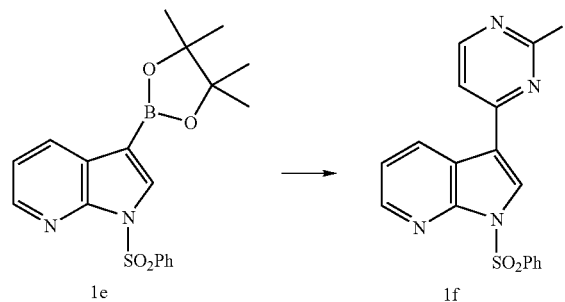

A mixture of compound 1e (15.00 g), 2,4-dichloropyrimidine (7.56 g) and tetrakis(triphenylphosphine)palladium(0) (4.51 g) in a solution of ethylene glycol dimethyl ether (200 mL) and aqueous Na$_2$CO$_3$ (2M, 60 mL) was refluxed overnight. The reaction was quenched with water and extracted with ethyl acetate. The combined organic phase was concentrated and the residue was purified on silica gel column (eluted with 100% dichloromethane and 3% acetone in dichloromethane) to provide 1-benzenesulfonyl-3-(2-chloropyrimidin-4-yl)-1H-pyrrolo[2,3-b]pyridine (1f) (7.83 g, 54%) as a white solid. $^1$H NMR (400 MHz, CDCl$_3$) δ 8.78 (d, J=8.0 Hz, 1H), 8.62 (d, J=5.6 Hz, 1H), 8.52 (d, J=4.8 Hz, 1H), 8.47 (s, 1H), 8.28 (d, J=7.6 Hz, 2H), 7.63 (t, J=7.6 HZ, 1H), 7.57 (d, J=5.2 Hz, 1H), 7.53 (t, J=8.0 Hz, 2H), 7.35 (dd, J=8.0 Hz, 4.8 Hz, 1H). MS (ESI) m/z: 371 (M+H)$^+$.

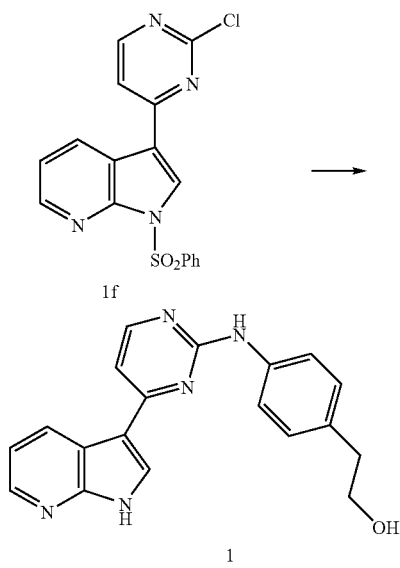

A mixture of compound 1f (4.00 g) and 2-(4-aminophenyl)-ethanol (2.96 g) in 1-methoxyethanol (30 mL) was heated at 160° C. for 17 hrs in a pressure tube. The mixture was then cooled, quenched with water and extracted with mixed THF and ethyl acetate. The combined organic phase was washed with brine and concentrated. The residue was subjected to silica column and eluted with 2-6% methanol in dichloromethane to give compound 1 (3.01 g, yield 84%) as a white solid. $^1$H NMR (400 MHz, CD$_3$OD) δ 8.89 (d, J=8.0 Hz, 1H), 8.26 (dd, J=5.2 Hz, 2.0 Hz, 2H), 8.22 (s, 1H), 7.59 (m, 2H), 7.20 (m, 4H), 3.78 (t, J=7.2 Hz, 2H), 2.83 (t, J=7.2 Hz, 2H). MS (ESI) m/z: 332 (M+H)$^+$.

EXAMPLE 2

[4-(1H-Pyrrolo[2,3-b]pyridin-3-yl)-pyrimidin-2-yl]-(3,4,5-trimethoxy-phenyl)-amine (2)

Using the procedure of example 1, 3,4,5-trimethoxyaniline (158 mg) was reacted with compound 1f (100 mg) to provide compound 2 (35 mg, 34%). $^1$H NMR (400 MHz, CD$_3$OD) δ 8.82 (d, J=8.0 Hz, 1H), 8.33 (d, J=5.2 Hz, 1H), 8.31 (d, J=4.8 Hz, 1H), 8.11 (s, 1H), 7.48 (s, 2H), 7.22 (dd, J=8.0 Hz, 4.8 Hz, 1H), 7.12 (d, J=4.8 Hz, 1H), 3.86 (s, 9H). MS (ESI) m/z: 378 (M+H)$^+$.

EXAMPLE 3

Phenyl-[4-(1H-pyrrolo[2,3-b]pyridin-3-yl)-pyrimidin-2-yl]-amine (3)

Using the procedure of example 1, aniline (83 mg) was reacted with compound 1f (100 mg) to provide compound 3 (36 mg, 47%). $^1$H NMR (400 MHz, CD$_3$OD) δ 8.88 (d, J=7.8 Hz, 1H), 8.29 (t, J=6.0 Hz, 2H), 8.19 (s, 1H), 7.69 (d, J=7.8 Hz, 2H), 7.36 (t, J=7.6 Hz, 2H), 7.21 (m, 1H), 7.08 (t, J=7.8 Hz, 2H). MS (ESI) m/z: 288 (M+H)$^+$.

EXAMPLE 4

2-{4-[4-(1H-Pyrrolo[2,3-b]pyridin-3-yl)-pyrimidin-2-ylamino]-phenoxy}-ethanol (4)

Using the procedure of example 1, 2-(4-aminophenoxy)-ethanol (265 mg) was reacted with compound 1f (200 mg) to provide compound 4 (132 mg, 71%). $^1$H NMR (400 MHz, CD$_3$OD) δ 8.85 (d, J=8.0 Hz, 1H), 8.25 (d, J=4.8 Hz, 1H), 8.23 (d, J=5.2 Hz, 1H), 8.22 (s, 1H), 7.54 (d, J=9.0 Hz, 2H), 7.18 (dd, J=8.0 Hz, 4.8 Hz, 1H), 7.16 (d, J=5.2 Hz, 1H), 6.98 (d, J=9.0 Hz, 2H). MS (ESI) m/z: 348 (M+H)$^+$.

EXAMPLE 5

(4-Methoxy-phenyl)-[4-(1H-pyrrolo[2,3-b]pyridin-3-yl)-pyrimidin-2-yl]-amine (5)

Using the procedure of example 1, p-anisidine (100 mg) was reacted with compound 1f (100 mg) to provide compound 5 (35 mg, 41%). $^1$H NMR (400 MHz, CD$_3$OD) δ 8.73 (d, J=8.0 Hz, 1H), 8.27 (m, 2H), 8.07 (s, 1H), 7.55 (d, J=9.0 Hz, 2H), 7.18 (dd, J=8.0 Hz, 4.8 Hz, 1H), 7.06 (d, J=5.6 Hz, 1H), 6.96 (d, J=9.0 Hz, 2H), 3.86 (s, 3H). MS (ESI) m/z: 318 (M+H)$^+$.

EXAMPLE 6

(3-Methoxy-phenyl)-[4-(1H-pyrrolo[2,3-b]pyridin-3-yl)-pyrimidin-2-yl]-amine (6)

Using the procedure of example 1, m-anisidine (100 mg) was reacted with compound 1f (100 mg) to provide compound 6 (25 mg, 29%). $^1$H NMR (400 MHz, CD$_3$OD) δ 8.84 (d, J=8.0 Hz, 1H), 8.33 (d, J=5.2 Hz, 1H), 8.31 (d, J=4.8 Hz, 1H), 8.12 (s, 1H), 7.48 (m, 1H), 7.30 (t, J=8.0 Hz, 1H), 7.23 (m, 2H), 7.13 (d, J=5.2 Hz, 1H), 6.68 (d, J=8.0 Hz, 1H), 3.86 (s, 3H). MS (ESI) m/z: 318 (M+H)+.

EXAMPLE 7

(2-Methoxy-phenyl)-[4-(1H-pyrrolo[2,3-b]pyridin-3-yl)-pyrimidin-2-yl]-amine (7)

Using the procedure of example 1, o-anisidine (100 mg) was reacted with compound 1f (100 mg) to provide compound 7 (20 mg, 24%). $^1$H NMR (400 MHz, CD$_3$OD) δ 8.81 (d, J=8.0 Hz, 1H), 8.40 (m, 1H), 8.33 (d, J=4.8 Hz, 1H), 8.30 (d, J=4.8 Hz, 1H), 8.20 (s, 1H), 7.23 (dd, J=8.0 Hz, 4.8 Hz, 1H), 7.20 (d, J=5.2 Hz, 1H), 7.08-7.01 (m, 3H), 3.97 (s, 3H). MS (ESI) m/z: 318 (M+H)+.

EXAMPLE 8

[4-(1H-Pyrrolo[2,3-b]pyridin-3-yl)-pyrimidin-2-yl]-o-tolyl-amine (8)

Using the procedure of example 1, o-toluidine (87 mg) was reacted with compound 1f (100 mg) to provide compound 8 (27 mg, 33%). $^1$H NMR (400 MHz, CD$_3$OD) δ 8.55 (d, J=8.0 Hz, 1H), 8.24 (d, J=5.2 Hz, 1H), 8.12 (s, 1H), 7.69 (d, J=7.6 Hz, 1H), 7.29 (q, J=7.6 Hz, 1H), 7.18 (d, J=7.2 Hz, 1H), 7.11 (d, J=5.6 Hz, 1H), 7.11 (dd, J=7.6 Hz, 4.8 Hz, 1H), 2.35 (s, 3H). MS (ESI) m/z: 302 (M+H)+.

EXAMPLE 9

[4-(1H-Pyrrolo[2,3-b]pyridin-3-yl)-pyrimidin-2-yl]-m-tolyl-amine (9)

Using the procedure of example 1, m-toluidine (87 mg) was reacted with compound 1f (100 mg) to provide compound 9 (37 mg, 46%). $^1$H NMR (400 MHz, CD$_3$OD) δ 8.90 (d, J=8;0 Hz, 1H), 8.30 (m, 2H), 8.18 (s, 1H), 7.63 (s, 1H), 7.43(d, J=8.0 Hz, 1H), 7.27 (d, J=7.6 Hz, 1H), 7.22 (m, 1H), 7.17 (d, J=5.2 Hz, 1H), 6.93 (d, J=8.0 Hz, 1H), 2.42 (s, 3H). MS (ESI) m/z: 302 (M+H)+.

EXAMPLE 10

[4-(1H-Pyrrolo[2,3-b]pyridin-3-yl)-pyrimidin-2-yl]-p-tolyl-amine (10)

Using the procedure of example 1, p-toluidine (87 mg) was reacted with compound 1f (100 mg) to provide compound 10 (35 mg, 43%). $^1$H NMR (400 MHz, CD$_3$OD) δ 8.82 (d, J=8.0 Hz, 1H), 8.28 (m, 2H), 8.13 (s, 1H), 7.62 (s, 1H), 7.56 (d, J=8.0 Hz, 2H), 7.21 (m, 2H), 7.12 (d, J=5.2 Hz, 1H), 2.38 (s, 3H). MS (ESI) m/z: 302 (M+H)+.

EXAMPLE 11

(4-Chloro-phenyl)-[4-(1-H-pyrrolo[2,3-b]pyridin-3-yl)-pyrimidin-2-yl]-amine (11)

Using the procedure of example 1, 4-chloro-aniline (103 mg) was reacted with compound 1f (100 mg) to provide compound 11 (24 mg, 28%). $^1$H NMR (400 MHz, CD$_3$OD) δ 8.82 (d, J=8.0 Hz, 1H), 8.32 (d, J=5.6 Hz, 1H), 8.30 (d, J=4.8 Hz, 1H), 8.14 (s, 1H), 7.69 (d, J=8.8 Hz, 2H), 7.33 (d, J=8.8 Hz, 2H), 7.24 (dd, J=8.0 Hz, 4.8 Hz, 1H), 7.16 (d, J=4.8 Hz, 1H). MS (ESI) m/z: 322 (M+H)+.

EXAMPLE 12

(2-Chloro-phenyl)-[4-(1H-pyrrolo[2,3-b]pyridin-3-yl)-pyrimidin-2-yl]-amine (12)

Using the procedure of example 1, 2-chloro-aniline (103 mg) was reacted with compound 1f (100 mg) to provide compound 12 (17 mg, 20%). $^1$H NMR (400 MHz, CD$_3$OD) δ 8.75 (d, J=7.6 Hz, 1H), 8.39 (d, J=8.4 Hz, 1H), 8.36 (d, J=5.2 Hz, 1H), 8.30 (d, J=4.8 Hz, 1H), 8.20 (s, 1H), 7.49 (d, J=7.6 Hz, 1H), 7.38 (t, J=8.0 Hz, 1H), 7.25 (d, J=5.2 Hz, 1H), 7.22 (dd, J=7.6 Hz, 4.8 Hz, 1H), 7.12 (t, J=7.6 Hz, 1H). MS (ESI) m/z 322: (M+H)+.

EXAMPLE 13

Cyclohexyl-[4-(1H-pyrrolo[2,3-b]pyridin-3-yl)-pyrimidin-2-yl]-amine (13)

Using the procedure of example 1, cyclohexylamine (88 mg) was reacted with compound 1f (100 mg) to provide compound 13 (33 mg, 42%). $^1$H NMR (400 MHz, CD$_3$OD) δ 8.91 (d, J=8.4 Hz, 1H), 8.26 (d, J=4.8 Hz, 1H), 8.16 (s, 1H), 8.10 (d, J=5.6 Hz, 1H), 7.22 (dd, J=8.0 Hz, 4.8 Hz, 1H), 6.97 (d, J=5.6 Hz, 1H), 3.86 (m, 1H), 2.13-1.27 (m, 10H).
MS (ESI) m/z 294: (M+H)+.

EXAMPLE 14

Cyclopentyl-[4-(1H-pyrrolo[2,3-b]pyridin-3-yl)-pyrimidin-2-yl]-amine (14)

Using the procedure of example 1, cyclopentylaamine (69 mg) was reacted with compound 1f (100 mg) to provide compound 14 (32 mg, 43%). $^1$H NMR (400 MHz, CD$_3$OD) δ 8.94 (d, J=7.8 Hz, 1H), 8.26 (d, J=4.8 Hz, 1H), 8.18 (s, 1H), 8.11 (d, J=5.6 Hz, 1H), 7.23 (dd, J=7.8 Hz, 5.6 Hz, 1H), 7.00 (d, J=5.6 Hz, 1H), 4.35 (m, 1H), 2.10 (m, 2H), 1.86-1.58 (m, 6H). MS (ESI) m/z: 280 (M+H)+.

EXAMPLE 15

Cycloheptyl-[4-(1H-pyrrolo[2,3-b]pyridin-3-yl)-pyrimidin-2-yl]-amine (15)

Using the procedure of example 1, cycloheptylamine (92 mg) was reacted with compound 1f (100 mg) to provide compound 15 (34 mg, 41%). $^1$H NMR (400 MHz, CD$_3$OD) δ 8.95 (d, J=8.0 Hz, 1H), 8.28 (d, J=4.8 Hz, 1H), 8.19 (s, 1H), 8.12 (d, J=5.6 Hz, 1H), 7.25 (dd, J=8.0 Hz, 4.8 Hz, 1H), 7.01 (d, J=5.6 Hz, 1H), 4.12 (m, 1H), 2.13 (m, 2H), 1.79-1.63 (m, 10H). MS (ESI) m/z: 308 (M+H)+.

EXAMPLE 16

Cyclohexylmethyl-[4-(1H-pyrrolo[2,3-b]pyridin-3-yl)-pyrimidin-2-yl]-amine (16)

Using the procedure of example 1, C-cyclohexyl-methylamine (92 mg) was reacted with compound 1f (100 mg) to provide compound 16 (42 mg, 51%). $^1$H NMR (400 MHz, CD$_3$OD) δ 8.96 (d, J=7.8 Hz, 1H), 8.28 (d, J=4.8 Hz, 1H), 8.20 (s, 1H), 8.12 (d, J=5.6 Hz, 1H), 7.25 (dd, J=7.8 Hz, 4.8 Hz, 1H), 7.02 (d, J=5.6 Hz, 1H), 3.37 (d, J=4.8 Hz, 2H), 1.94-1.90 (m, 5H), 1.34-1.04 (m, 6H). MS (ESI) m/z: 308 (M+H)+.

EXAMPLE 17

(4-Methyl-cyclohexyl)-[4-(1H-pyrrolo[2,3-b]pyridin-3-yl)-pyrimidin-2-yl]-amine (17)

Using the procedure of example 1, 4-methylcyclohexylamine (92 mg) was reacted with compound 1f (100 mg) to provide compound 17 (25 mg, 30%) as a mixture of cis- and trans-isomers. $^1$H NMR (400 MHz, CDCl$_3$) δ 8.94 (d, J=8.0 Hz, 1H), 8.92 (d, J=8.0 Hz, 1H), 8.28 (m, 2H), 8.20 (s, 1H), 8.19 (s, 1H), 8.14 (d, J=5.2 Hz, 1H), 8.11 (d, J=5.2 Hz, 1H), 7.25 (m, 2H), 7.03 (d, J=5.6 Hz, 1H), 7.00 (d, J=5.6 Hz, 1H), 4.15 (m, 1H), 3.83 (m, 1H), 2.15 (m, 2H), 1.89-1.14 (m, 16H), 1.01 (d, J=6.4 Hz, 3H), 0.98 (d, J=6.4 Hz, 3H). MS (ESI) m/z: 308 (M+H)$^+$.

EXAMPLE 18 trans-4-[4-(1H-Pyrrolo[2,3-b]pyridin-3-yl)-pyrimidin-2-ylamino]-cyclohexanol (18)

Using the procedure of example 1, trans-4-amino-cyclohexanol (200 mg) was reacted with compound 1f (100 mg) to provide compound 18 (18 mg, 22%). $^1$H NMR (400 MHz, CD$_3$OD) δ 8.95 (d, J=8.0 Hz, 1H), 8.28 (d, J=4.8 Hz, 1H), 8.20 (s, 1H), 8.13 (d, J=5.6 Hz, 1H), 7.26 (dd, J=8.0 Hz, 4.8. Hz, 1H), 7.02 (d, J=5.2 Hz, 1H), 3.91 (m, 1H), 3.65 (m, 1H), 2.17 (m, 2H), 2.05 (m, 2H), 1.45 (m, 4H). MS (ESI) m/z: 310 (M+H)$^+$.

EXAMPLE 19

[4-(2-Pyrrolidin-1-yl-ethyl)-phenyl]-[4-(1H-pyrrolo[2,3-b]pyridin-3-yl)-pyrimidin-2-yl]-amine (19)

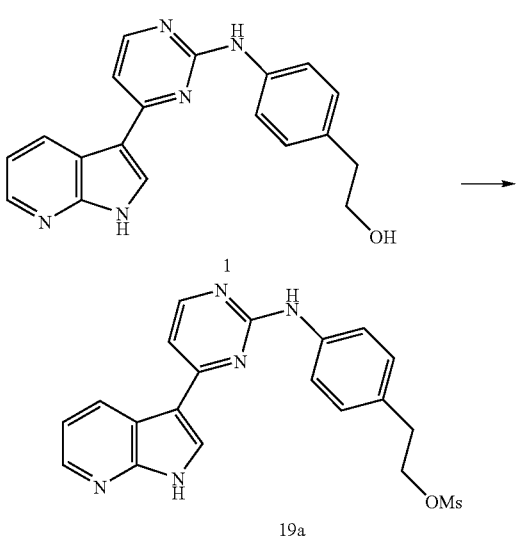

Methanesulfonyl chloride (0.214 g) was added dropwise to a suspension of compound 1 (0.310 g) and triethylamine (0.189 g) in THF (18 mL) at 0° C. The mixture was warmed to rt and stirred for 10 min. The reaction was quenched with water and extracted with ethyl acetate. The organic phase was washed with brine, then dried over Na$_2$SO$_4$ and concentrated to give compound 19a without further purification (0.420 g, 100%). $^1$H NMR (400 MHz, CD$_3$OD) δ 8.91 (d, J=8.4 Hz, 1H), 8.28 (d, J=5.6 Hz, 1H), 8.26 (d, J=5.2 Hz, 1H), 8.23 (s, 1H), 7.67 (d, J=8.4 Hz, 2H), 7.27 (d, J=8.4 Hz, 2H), 7.23 (dd, J=8.0 Hz, 4.8 Hz, 1H), 7.20 (d, J=5.6 Hz, 1 Hz). MS (ESI) m/z: 410 (M+H)$^+$.

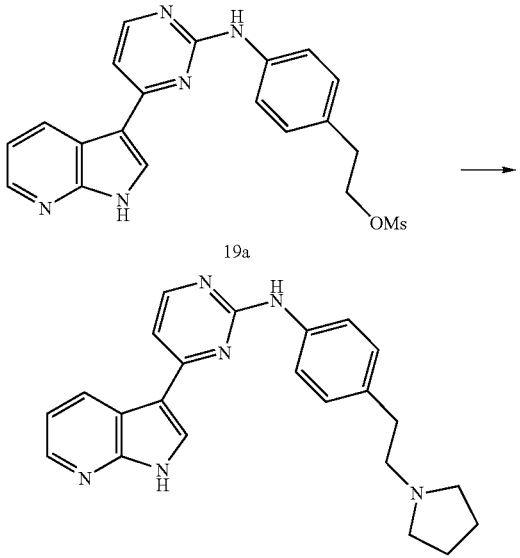

A mixture of compound 19a (200 mg) and pyrrolidine (200 mg) was heated at 60° C. for 4 hrs. The reaction was quenched with water and extracted with ethyl acetate, then the organic phase was washed with brine and concentrated. The residue was purified on silica gel column and eluted with ~3-5% methanol (with NH$_3$) in DCM to afford compound 19 (112 mg, 60%). $^1$H NMR (400 MHz, CD$_3$OD) δ 8.92 (d, J=8.0 Hz, 1H), 8.29 (m, 2H), 8.25 (s, 1H), 7.63 (d, J=9.2 Hz, 2H), 7.22 (m, 4H), 2.83 (m, 4H), 2.70 (m, 4H), 1.88 (m, 4H). MS (ESI) m/z: 385 (M+H)$^+$.

EXAMPLE 20

[4-(2-piperazin-1-yl-ethyl)-phenyl]-[4-(1H-pyrrolo[2,3-b]pyridin-3-yl)-pyrimidin-2-yl]-amine (20)

Using the procedure of example 19, piperazine (200 mg) was reacted with compound 19a (200 mg) to provide compound 20 (112 mg, 15%). $^1$H NMR (400 MHz, CD$_3$OD) δ 8.87 (d, J=8.0 Hz, 1H), 8.26 (d, J=4.8 Hz, 2H), 8.21 (s, 1H), 7.60 (d, J=6.4 Hz, 2H), 7.18 (m, 4H), 2.92 (t, J=4.8 Hz, 4H), 2.81 (m, 2H), 2.64-2.58 (m, 6H). MS (ESI) m/z: 400 (M+H)$^+$.

EXAMPLE 21

{4-[2-(4-Methyl-piperazin-1-yl)-ethyl]-phenyl}-[4-(1H-pyrrolo[2,3-b]pyridin-3-yl)-pyrimidin-2-yl]-amine (21)

Using the procedure of example 19, 1-methyl-piperazine (200 mg) was reacted with compound 19a (200 mg) to provide compound 21. (74 mg, 37%). $^1$H NMR (400 MHz, CD$_3$OD) δ 8.87 (d, J=7.8 Hz, 1H), 8.27 (d, J=5.6 Hz, 2H), 8.22 (s, 1H), 7.61 (d, J=8.8 Hz, 2H), 7.18 (m, 4H), 2.80 (m, 2H), 2.67-2.61 (m, 10H), 2.31 (s, 3H). MS (ESI) m/z: 414 (M+H)⁺.

EXAMPLE 22

[4-(2-Morpholin-4-yl-ethyl)-phenyl]-[4-(1H-pyrrolo[2,3-b]pyridin-3-yl)-pyrimidin-2-yl]-amine (22)

Using the procedure of example 19, morpholine (200 mg) was reacted with compound 19a (200 mg) to provide compound 22 (61 mg, 31%). ¹H NMR (400 MHz, CD₃OD) δ 8.92 (d, J=7.8 Hz, 1H), 8.29 (d, J=5.6 Hz, 2H), 8.25 (s, 1H), 7.63 (d, J=8.4 Hz, 2H), 7.22 (m, 4H), 3.77 (t, J=4.8 Hz, 4H), 2.85 (m, 2H), 2.69-2.60 (m, 6H). MS (ESI) m/z: 401 (M+H)⁺.

EXAMPLE 23

[4-(2-Dimethylamino-ethyl)-phenyl]-[4-(1H-pyrrolo[2,3-b]pyridin-3-yl)-pyrimidin-2-yl]-amine (23)

Using the procedure of example 19, dimethylamine (2.4 mL, 2M solution in THF) was reacted with compound 19a (200 mg) to provide compound 23 (100 mg, 57%). ¹H NMR (400 MHz, CD₃OD) δ 8.92 (d, J=7.8 Hz, 1H), 8.29 (d, J=5.6 Hz, 2H), 8.25 (s, 1H), 7.63 (d, J=8.4 Hz, 2H), 7.22 (m, 4H), 2.83 (m, 2H), 2.62 (m, 2H), 2.36 (s, 6H). MS (ESI) m/z: 359 (M+H)⁺.

EXAMPLE 24

[4-(2-Diethylamino-ethyl)-phenyl]-[4-(1H-pyrrolo[2,3-b]pyridin-3-yl)-pyrimidin-2-yl]-amine (24)

Using the procedure of example 19, diethylamine (200 mg) was reacted with compound 19a (200 mg) to provide compound 24 (100 mg, 53%). ¹H NMR (400 MHz, CD₃OD) δ 8.90 (d, J=7.8 Hz, 1H), 8.27 (m, 2H), 8.23 (s, 1H), 7.62 (d, J=8.8 Hz, 2H), 7.19 (m, 4H), 2.77 (s, 4H), 2.70 (q, J=7.2 Hz, 4H), 1.13 (t, J=7.2 Hz, 6H). MS (ESI) m/z: 387 (M+H)⁺.

EXAMPLE 25

[4-(2-Methylamino-ethyl)-phenyl]-[4-(1H-pyrrolo[2,3-b]pyridin-3-yl)-pyrimidin-2-yl]-amine (25)

Using the procedure of example 19, methylamine (2 mL, 2.0M solution in THF) was reacted with compound 19a (200 mg) to provide compound 25 (14 mg, 8%). ¹H NMR (400 MHz, CD₃OD) δ 8.87 (d, J=8.4 Hz, 1H), 8.29 (d, J=5.6 Hz, 2H), 8.23 (s, 1H), 7.69 (d, J=8.4 Hz, 2H), 7.31 (d, J=8.8 Hz, 2H), 7.26 (m, 2H), 3.28 (t, J=8.0 Hz, 2H), 3.06 (t, J=8.0 Hz, 2H), 2.75 (s, 3H). MS (ESI) m/z: 345 (M+H)⁺.

EXAMPLE 26

[4-(2-Ethylamino-ethyl)-phenyl]-[4-(1H-pyrrolo[2,3-b]pyridin-3-yl)-pyrimidin-2-yl]-amine (26)

Using the procedure of example 19, ethylamine (2 mL, 2.0M solution in THF) was reacted with compound 19a (200 mg) to provide compound 26 (32 mg, 22%). ¹H NMR (400 MHz, CD₃OD) δ 8.93 (d, J=7.8 Hz, 1H), 8.29 (m, 2H), 8.26 (s, 1H), 7.65 (d, J=8.8 Hz, 2H), 7.23 (m, 4H), 2.87 (m, 4H), 2.72 (q, J=7.2 Hz, 2H), 1.16 (t, J=7.2 Hz, 3H). MS (ESI) m/z: 359 (M+H)⁺.

EXAMPLE 27

(4-Methoxy-2-methylphenyl)-[4-(1H-pyrrolo[2,3-b]pyridin-3-yl)-pyrimidin-2-yl]-amine (27)

Using the procedure of example 1, 4-methoxy-2-methylaniline, (111 mg) was reacted with compound 1f (100 mg) to provide compound 27 (18 mg, 20%). ¹H NMR (400 MHz, CD₃OD) δ 8.48 (d, J=7.2 Hz, 1H), 8.20 (d, J=4.8 Hz, 1H), 8.17 (s, 1H), 8.15 (d, J=5.2 Hz, 1H), 7.31 (d, J=8.4 Hz, 1H), 7.10 (d, J=5.6 Hz, 1H), 7.03 (m, 1H), 6.90 (s, 1H), 6.84 (d, J=8.4 Hz, 1H), 3.84 (s, 3H), 2.26 (s, 3H). MS (ESI) m/z: 332 (M+H)⁺.

EXAMPLE 28

(2-Bromophenyl)-[4-(1H-pyrrolo[2,3-b]pyridin-3-yl)-pyrimidin-2-yl]-amine (28)

Using the procedure of example 1, 2-bromoaniline (139 mg) was reacted with compound 1f (100 mg) to provide compound 28 (23 mg, 23%). ¹H NMR (400 MHz, CD₃OD) δ 8.67 (d, J=8.0 Hz, 1H), 8.30 (t, J=5.2 Hz, 1H), 8.25 (d, J=1.2 Hz, 1H), 8.24 (s, 1H), 8.15 (d, J=8.0 Hz, 1H), 7.67 (d, J=8.0 Hz, 1H), 7.41 (t, J=8.0 Hz, 1H), 7.26 (d, J=6.0 HZ, 1H), 7.15 (dd, J=7.8 Hz, 4.8 Hz, 1H), 7.08 (t, J=7.8 Hz, 1H). MS (ESI) m/z: 366 (M+H)⁺.

EXAMPLE 29

(2-trifluoromethylphenyl)-[4-(1H-pyrrolo[2,3-b]pyridin-3-yl)-pyrimidin-2-yl]-amine (29)

Using the procedure of example 1, 2-trifluoromethylaniline (131 mg) was reacted with compound 1f (100 mg) to provide compound 29 (6 mg, 6%). ¹H NMR (400 MHz, CD₃OD) δ 8.56 (d, J=8.0 Hz, 1H), 8.27 (t, J=5.6 Hz, 1H), 8.24 (s, 1H), 8.22 (d, J=1.6 Hz, 1H), 8.03 (d, J=8.0 Hz, 1H), 7.75 (d, J=7.8 Hz, 1H), 7.69 (t, J=8.0 Hz, 1H), 7.40 (t, J=8.0 Hz, 1H), 7.27 (d, J=5.6 Hz, 4.8 Hz, 1H), 7.10 (dd, J=8.0 Hz, 4.8 Hz, 1H). MS (ESI) m/z: 356 (M+H)⁺.

EXAMPLE 30

(2-Hydroxyphenyl)-[4-(1H-pyrrolo[2,3-b]pyridin-3-yl)-pyrimidin-2-yl]-amine (30)

Using the procedure of example 1, 2-aminophenol (88 mg) was reacted with compound 1f (100 mg) to provide compound 30 (35 mg, 43%). ¹H NMR (400 MHz, CD₃OD) δ 8.83 (d, J=8.0 Hz, 1H), 8.28 (m, 2H), 8.25 (s, 1H), 7.91 (d, J=7.6 Hz, 1H), 7.22 (m, 2H), 6.97 (m, 1H), 6.91 (m, 2H). MS (ESI) m/z: 304 (M+H)⁺.

EXAMPLE 31

(2-Fluorophenyl)-[4-(1H-pyrrolo[2,3-b]pyridin-3-yl)-pyrimidin-2-yl]-amine (31)

Using the procedure of example 1, 2-fluoroaniline (90 mg) was reacted with compound 1f (100 mg) to provide compound 31 (45 mg, 55%). ¹H NMR (400 MHz, CD₃OD) δ 8.73 (d, J=8.0 Hz, 1H), 8.29 (d, J=5.2 Hz, 1H), 8.26 (m, 1H), 8.24

(s, 1H), 8.04 (t, J=8.0 Hz, 1H), 7.25 (d, J=5.6 Hz, 1H), 7.22-7.14 (m, 4H). MS (ESI) m/z: 306 (M+H)⁺.

EXAMPLE 32

(2-Ethylphenyl)-[4-(1H-pyrrolo[2,3-b]pyridin-3-yl)-pyrimidin-2-yl]-amine (32)

Using the procedure of example 1, 2-ethylaniline (98 mg) was reacted with compound 1f (100 mg) to provide compound 32 (44 mg, 52%). $^1$H NMR (400 MHz, CD$_3$OD) δ 8.48 (d, J=8.0 Hz, 1H), 8.21-8.18 (m, 3H), 7.51 (d, J=7.2 Hz, 1H), 7.35 (d, J=7.2 Hz, 1H), 7.27 (m, 2H), 7.14 (d, J=5.2 Hz, 1H), 7.03 (dd, J=8.0 Hz, 4.8 Hz, 1H), 2.71 (q, J=7.6 Hz, 2H), 1.20 (t, J=7.6 Hz, 3H). MS (ESI) m/z: 316 (M+H)⁺.

EXAMPLE 33

(2,4-Dimethylphenyl)-[4-(1H-pyrrolo[2,3-b]pyridin-3-yl)-pyrimidin-2-yl]-amine (33)

Using the procedure of example 1, 2,4-dimethylaniline (98 mg) was reacted with compound 1f (100 mg) to provide compound 33 (37 mg, 44%). $^1$H NMR (400 MHz, CD$_3$OD) δ 8.50 (d, J=8.0 Hz, 1H), 8.21 (d, J=4.8 Hz, 1H), 8.18 (s, 1H), 8.17 (d, J=5.6 Hz, 1H), 7.36 (d, J=8.0 Hz, 1H), 7.14 (s, 1H), 7.12 (d, J=5.6 Hz, 1H), 7.07 (d, J=8.0 Hz, 1H), 7.03 (dd, J=8.0 Hz, 4.8 Hz, 1H), 2.38 (s, 3H), 2.26 (s, 3H). MS (ESI) m/z: 316 (M+H)⁺.

EXAMPLE 34

(2,3-Dimethylphenyl)-[4-(1H-pyrrolo[2,3-b]pyridin-3-yl)-pyrimidin-2-yl]-amine (34)

Using the procedure of example 1, 2,3-dimethylaniline (98 mg) was reacted with compound 1f (100 mg) to provide compound 34 (50 mg, 59%). $^1$H NMR (400 MHz, CD$_3$OD) δ 8.42 (d, J=8.0 Hz, 1H), 8.21 (d, J=4.8 Hz, 1H), 8.19 (s, 1H), 8.17 (d, J=5.2 Hz, 1H), 7.27 (d, J=7.2 Hz, 1H), 7.18-7.13 (m, 3H), 7.02 (dd, J=8.0 Hz, 4.8 Hz, 1H), 2.37 (s, 3H), 2.20 (s, 3H). MS (ESI) m/z: 316 (M+H)⁺.

EXAMPLE 35

(2,6-Dimethylphenyl)-[4-(1H-pyrrolo[2,3-b]pyridin-3-yl)-pyrimidin-2-yl]-amine (35).

Using the procedure of example 1, 2,6-dimethylaniline (98 mg) was reacted with compound 1f (100 mg) to provide compound 35 (34 mg, 40%). $^1$H NMR (400 MHz, CD$_3$OD) δ 8.40 (d, J=8.0 Hz, 1H), 8.21 (d, J=4.8 Hz, 1H), 8.19 (s, 1H), 8.17 (d, J=5.2 Hz, 1H), 7.50 (d, J=7.2 Hz, 1H), 7.35 (d, J=7.2 Hz, 1H), 7.14 (d, J=5.2 Hz, 2H), 7.03 (t, J=5.2 Hz, 1H), 2.36 (s, 6H). MS (ESI) m/z: 316 (M+H)⁺.

EXAMPLE 36

(2,4-Dichlorophenyl)-[4-(1H-pyrrolo[2,3-b]pyridin-3-yl)-pyrimidin-2-yl]-amine (36)

Using the procedure of example 1, 2,4-dichloroaniline (131 mg) was reacted with compound 1f (100 mg) to provide compound 36 (47 mg, 49%). $^1$H NMR (400 MHz, CD$_3$OD) δ 8.69 (d, J=8.0 Hz, 1H), 8.33 (d, J=4.8 Hz, 1H), 8.26 (d, J=5.6 Hz, 1H), 8.23 (s, 1H), 8.20 (d, J=8.0 Hz, 1H), 7.57 (s, 1H), 7.36 (d, J=5.6 Hz, 1H), 7.30 (d, J=8.0 Hz, 1H), 7.18 (dd, J=8.0 Hz, 4.8 Hz, 1H). MS (ESI) m/z: 356 (M+H)⁺.

EXAMPLE 37

(4-Aminophenyl)-[4-(1H-pyrrolo[2,3-b]pyridin-3-yl)-pyrimidin-2-yl]-amine (37)

Using the procedure of example 1, 1,4-phenylenediamine (175 mg) was reacted with compound 1f (100 mg) to provide compound 37 (40 mg, 25%). $^1$H NMR (400 MHz, CD$_3$OD) δ 8.43 (d, J=8.0 Hz, 1H), 8.23 (d, J=8.0 Hz, 1H), 8.20 (s, 1H), 8.18 (d, J=4.8 Hz, 1H), 7.36 (m, 1H), 7.33 (d, J=8.0 Hz, 1H), 7.18 (dd, J=8.0 Hz, 5.6 Hz, 1H), 7.11 (d, J=5.2 Hz, 1H), 6.84 (d, J=8.0 Hz, 1H), 6.80 (d, J=8.0 Hz, 1H). MS (ESI) m/z: 301 (M+H)⁺.

EXAMPLE 38

(4-Dimethylaminophenyl)-[4-(1H-pyrrolo[2,3-b]pyridin-3-yl)-pyrimidin-2-yl]-amine (38)

Using the procedure of example 1, N,N-dimethyl-p-phenylenediamine (221 mg) was reacted with compound 1f (100 mg) to provide compound 38 (52 mg, 29%). $^1$H NMR (400 MHz, CD$_3$OD) δ 8.85 (d, J=8.0 Hz, 1H), 8.25 (d, J=8.0 Hz, 1H), 8.20 (s, 1H), 8.18 (d, J=4.8 Hz, 1H), 7.45 (d, J=8.0 Hz, 1H), 7.43 (m, 1H), 7.18 (dd, J=8;0 Hz, 5.6 Hz, 1H), 7.12 (d, J=5.6 Hz, 1H), 6.88 (d, J=8.0 Hz, 1H), 6.85 (d, J=8.0 Hz, 1H), 2.90 (s, 6H).
MS (ESI) m/z: 331 (M+H)⁺.

EXAMPLE 39

(4-Hydroxyphenyl)-[4-(1H-pyrrolo[2,3-b]pyridin-3-yl)-pyrimidin-2-yl]-amine (39)

Using the procedure of example 1, 4-aminophenol (177 mg) was reacted with compound 1f (200 mg) to provide compound 39 (48 mg, 29%). $^1$H NMR (400 MHz, CD$_3$OD) δ 8.48 (d, J=8.0 Hz, 1H), 8.24 (s, 1H), 8.23 (d, J=8.0 Hz, 1H), 8.12 (d, J=4.8 Hz, 1H), 7.45 (d, J=8.0 Hz, 1H), 7.05 (dd, J=8.0 Hz, 5.6 Hz, 1H), 7.00 (d, J=5.2 Hz, 1H), 6.98 (m, 1H), 6.85 (d, J=8.0 Hz, 1H), 6.83 (d, J=8.0 Hz, 1H). MS (ESI) m/z: 304 (M+H)⁺.

EXAMPLE 40

(4-Ethoxyphenyl)-[4-(1H-pyrrolo[2,3-b]pyridin-3-yl)-pyrimidin-2-yl]-amine (40)

Using the procedure of example 1, 4-ethoxyaniline (222 mg) was reacted with compound 1f (200 mg) to provide compound 40 (55 mg, 31%). $^1$H NMR (400 MHz, DMSO) δ 8.90 (d, J=8.0 Hz, 1H), 8.45 (s, 1H), 8.30 (d, J=5.6 Hz, 2H), 7.66 (d, J=8.0 Hz, 2H), 7.25 (d, J=5.6 Hz, 1H), 7.20 (m, 1H), 6.90 (d, J=8.0 Hz, 2H), 4.05 (q, J=8.0 Hz, 2H), 1.36 (t, J=8.0 Hz, 3H). MS (ESI) m/z: 332 (M+H)⁺.

EXAMPLE 41

(4-Bromo-2-methylphenyl)-[4-(1H-pyrrolo[2,3-b]pyridin-3-yl)-pyrimidin-2-yl]-amine (41)

Using the procedure of example 1, 4-bromo-2-methylaniline (300 mg) was reacted with compound 1f (200 mg) to provide compound 41 (85 mg, 41%). $^1$H NMR (400 MHz, DMSO) δ 12.28 (br s, 1H), 8.75 (br s, 1H), 8.55 (d, J=7.8 Hz, 1H), 8.43 (s, 1H), 8.28 (d, J=7.2 Hz, 1H), 8.26 (m, 1H), 7.52 (m, 2H), 7.40 (d, J=10.8 Hz, 1H), 7.27 (d, J=7.2 Hz, 1H), 7.06 (dd, J=10.8 Hz, 6.0 Hz, 1H), 2.25 (s, 3H).
MS (ESI) m/z: 382 (M+H)+.

EXAMPLE 42 trans-N-[4-(1H-Pyrrolo[2,3-b]pyridin-3-yl)-pyrimidin-2-yl]-cyclohexane-1,4-diamine (42)

Using the procedure of example 1, trans-1,4-cyclohexyldiamine (277 mg) was reacted with compound 1f (300 mg) to provide compound 42 (86 mg, 34%). $^1$H NMR (400 MHz, CD$_3$OD) δ 8.90 (d, J=8.0 Hz, 1H), 8.25 (d, J=5.6 Hz, 1H), 8.17 (s, 1H), 8.12 (d, J=8.0 Hz, 1H), 7.22 (m, 1H), 6.95 (d, J=5.6 Hz, 1H), 3.85 (m, 1H), 2.78 (m, 1H), 2.18 (m, 2H), 2.20 (m, 2H), 1.40 (m, 4H). MS (ESI) m/z: 309 (M+H)+.

EXAMPLE 43

(4-Aminocyclohexyl)-[4-(1H-pyrrolo[2,3-b]pyridin-3-yl)-pyrimidin-2-yl]-amine (43)

Using the procedure of example 1, a mixture of cis- and trans-1,4-cyclohexyldiamine (277 mg) was reacted with compound 1f (300 mg) to provide compound 43 (132 mg, 53%). $^1$H NMR (400 MHz, CD$_3$OD) δ 8.88 (m, 2H), 8.27 (d, 1H), 8.26 (d, 1H), 8.16 (s, 1H), 8.15 (s, 1H), 8.11 (d, J=8.0 Hz, 1H), 8.09 (d, 1H), 7.22 (dd, 1H), 7.21 (dd, 1H), 6.98 (d, 1H), 6.96 (d, 1H), 4.07 (m, 1H), 3.84 (m, 1H), 2.91 (m, 1H), 2.74 (m, 1H), 2.17-1.86 (m, 4H), 1.80 (m, 4H), 1.59 (m, 4H), 1.41 (m, 4H). MS (ESI) m/z: 309 (M+H)+.

EXAMPLE 44

[4-(2-hydroxyethyl)-2-methylphenyl)]-[4-(1H-pyrrolo[2,3-b]pyridin-3-yl)-pyrimidin-2-yl]-amine (44)

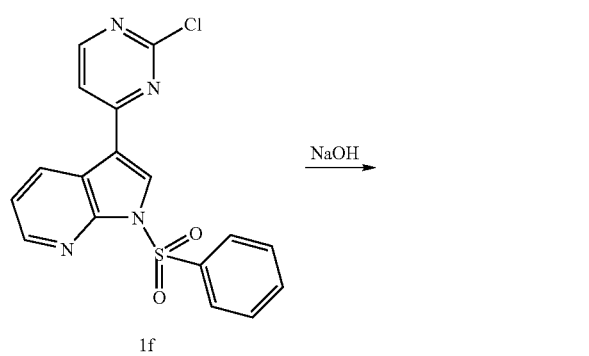

Compound 1f (1.0 g) was dissolved in 1,4-dioxane (50 mL), followed by addition of 1 M aqueous NaOH (20 mL). The mixture was heated to 90° C. for a few hours, then poured into water. Acetic acid was added until the aqueous phase became acidic, then the mixture was extracted with EtOAc. The organic layer was separated, dried with MgSO$_4$, then concentrated to afford 0.60 g (96%) of the desired compound 1g. MS (ESI) m/z: 231 (M+H)+.

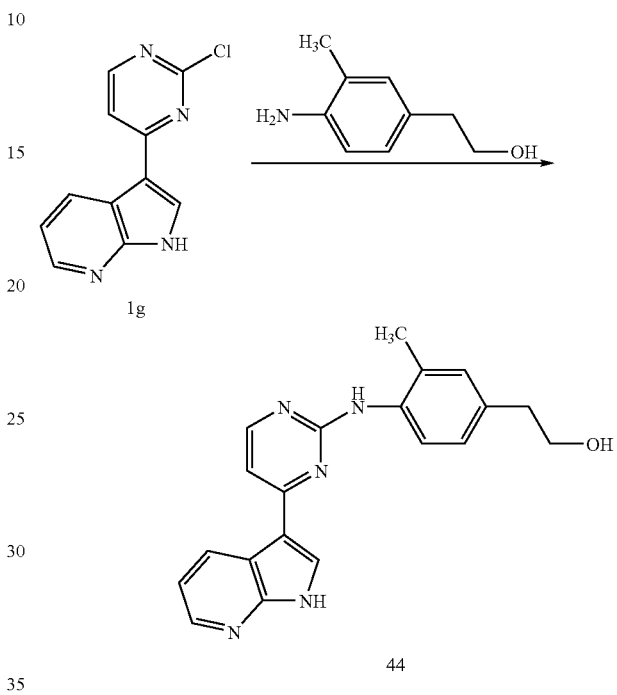

Using the procedure of example 1,4-(2-hydroxyethyl)-2-methylaniline (82 mg) was reacted with compound 1g (62 mg) to provide compound 44 (32 mg, 34%). $^1$H NMR (300 MHz, CD$_3$OD) δ 8.52 (d, J=8.0 Hz, 1H), 8.20 (m, 1H), 8.18 (s, 1H), 8.15 (d, J=5.6 Hz, 1H), 7.42 (d, J=8.0 Hz, 1H), 7.18 (s, 1H), 7.14 (d, J=5.2 Hz, 1H), 7.12 (d, J=5.6 Hz, 1H), 7.05 (dd, J=8.0 Hz, 5.2 Hz, 1H). 3.72 (t, J=8.0 Hz, 2H), 2.85 (t, J=8.0 Hz, 2H), 2.27 (s, 3H). MS (ESI) m/z: 346 (M+H)+.

EXAMPLE 45

[4-(2-Methylaminoethyl)-2-methylphenyl)]-[4-(1H-pyrrolo[2,3-b]pyridin-3-yl)-pyrimidin-2-yl]-amine (45)

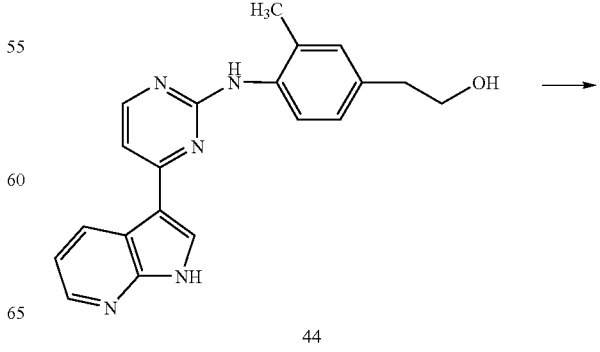

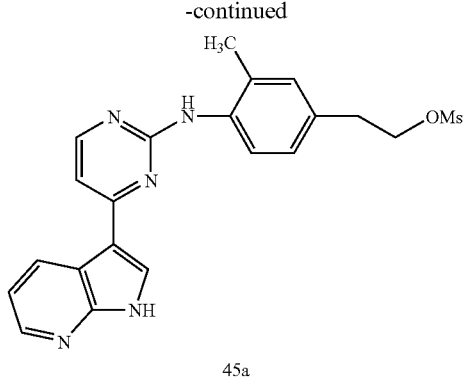

45a

Using the procedure of example 19, compound 44 (1.0 g) was reacted with methanesulfonyl chloride (0.663 g) to provide compound 45a (0.81 g, 66%). $^1$H NMR (400 MHz, DMSO) δ 11.89 (br s, 1H), 8.60 (d, J=8.0 Hz, 1H), 8.29 (s, 1H), 8.27 (d, J=5.6 Hz, 1H), 8.06 (br s, 1H), 7.72 (d, J=8.0 Hz, 1H), 7.22 (s, 1H), 7.20-7.00 (m, 4H), 4.42 (t, J=6.0 Hz, 2H), 3.05 (t, J=6.0 Hz, 2H), 2.96 (s, 3H), 2.32 (s, 3H). MS (ESI) m/z: 424 (M+H)$^+$.

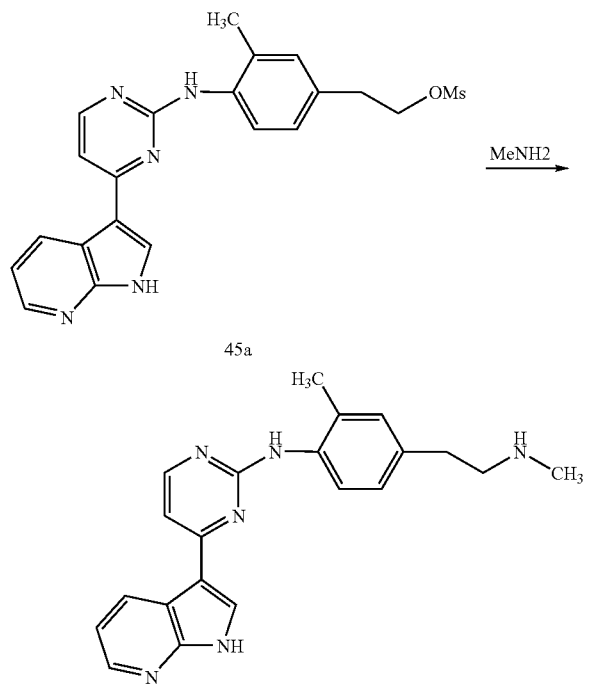

Using the procedure of example 19, compound 45a (30 mg) was reacted with methylamine (11 mg) to provide compound 45 (12 mg, 47%). $^1$H NMR (400 MHz, DMSO) δ 12.30 (br s, 1H), 8.63 (s, 1H), 8.50 (d, J=7.6 Hz, 1H), 8.39 (s, 1H), 8.25 (m, 2H), 7.37 (d, J=8.4 Hz, 1H), 7.20 (d, J=4.8 Hz, 1H), 7.12 (s, 1H), 7.06 (d, J=8.4 Hz, 1H), 7.01 (dd, J=7.6 Hz, 4.8 Hz, 1H), 3.43 (br s, 1H), 2.80-2.74 (m, 4H), 2.35 (s, 3H), 2.21 (s, 3H). MS (ESI) m/z: 359 (M+H)$^+$.

EXAMPLE 46

[4-(2-Dimethylaminoethyl)-2-methylphenyl)]-[4-(1H-pyrrolo[2,3-b]pyridin-3-yl)-pyrimidin-2-yl]-amine (46)

Using the procedure of example 19, compound 45a (30 mg) was reacted with dimethylamine (16 mg) to provide compound 46 (22 mg, 82%). $^1$H NMR (400 MHz, CD$_3$OD) δ 12.21 (br s, 1H), 8.62 (s, 1H), 8.50 (d, 1H), 8.39 (d, 1H), 8.24 (m, 2H), 7.36 (d, 1H), 7.20 (d, 1H), 7.12 (s, 1H), 7.08 (d, 1H), 7.01 (dd, 1H), 2.71 (t, 2H), 2.51 (t, 2H), 2.22 (s, 6H), 2.21 (s, 3H). MS (ESI) m/z: 373 (M+H)$^+$.

EXAMPLE 47

[4-(2-Diethylaminoethyl)-2-methylphenyl)]-[4-(1H-pyrrolo[2,3-b]pyridin-3-yl)-pyrimidin-2-yl]-amine (47)

Using the procedure of example 19, compound 45a (80 mg) was reacted with diethylamine (69 mg) to provide compound 47 (55 mg, 73%). $^1$H NMR (400 MHz, CD$_3$OD) δ 8.53 (d, 1H), 8.19 (m, 2H), 8.17 (s, 1H), 7.45 (d, 1H), 7.19 (s, 1H), 7.15 (d, 1H), 7.12 (d, 1H), 7.04 (dd, 1H), 2.85 (m, 4H), 2.78 (m, 4H), 2.29 (s, 3H), 1.15 (t, 6H). MS (ESI) m/z: 401 (M+H)$^+$.

EXAMPLE 48

[4-(2-Pyrrolidin-1-ylethyl)-2-methylphenyl)]-[4-(1H-pyrrolo[2,3-b]pyridin-3-yl)-pyrimidin-2-yl]-amine (48)

Using the procedure of example 19, compound 45a (80 mg) was reacted with pyrrolidine (67 mg) to provide compound 48 (60 mg, 80%). $^1$H NMR (400 MHz, CD$_3$OD) δ 8.50 (d, 1H), 8.20 (m, 3H), 7.45 (d, 1H), 7.18 (s, 1H), 7.14 (d, 1H), 7.10 (d, 1H), 7.03 (dd, 1H), 2.90 (m, 4H), 2.75 (m, 4H), 2.36 (s, 3H), 1.88 (m, 4H). MS (ESI) m/z: 399 (M+H)$^+$.

EXAMPLE 49

{4-[2-(Morpholin-4-yl)ethyl]-2-methylphenyl}-[4-(1H-pyrrolo[2,3-b]pyridin-3-yl)-pyrimidin-2-yl]-amine (49)

Using the procedure of example 19, compound 45a (80 mg) was reacted with morpholine (82 mg) to provide compound 49 (70 mg, 89%). $^1$H NMR (400 MHz, CD$_3$OD) δ 8.50 (d, 1H), 8.20 (m, 3H), 7.43 (d, 1H), 7.18 (s, 1H), 7.14 (d, 1H), 7.10 (d, 1H), 7.03 (dd, 1H), 3.75 (m, 4H), 2.88 (m, 2H), 2.70 (m, 2H), 2.60 (m, 4H), 2.25 (s, 3H). MS (ESI) m/z: 415 (M+H)$^+$.

EXAMPLE 50

{4-[2-(Piperidin-1-yl)ethyl]-2-methylphenyl}-[4-(1H-pyrrolo[2,3-b]pyridin-3-yl)-pyrimidin-2-yl]-amine (50)

Using the procedure of example 19, compound 45a (80 mg) was reacted with piperidine (80 mg) to provide compound 50 (65 mg, 83%). $^1$H NMR (400 MHz, CD$_3$OD) δ 8.54 (d, 1H), 8.18 (m, 3H), 7.42 (d, 1H), 7.20 (s, 1H), 7.15 (d, 1H), 7.11 (d, 1H), 7.05 (dd, 2H), 2.85 (m, 2H), 2.70 (m, 6H), 2.25 (s, 3H), 1.70 (m, 4H), 1.55 (m, 2H). MS (ESI) m/z: 413 (M+H)$^+$.

EXAMPLE 51

{4-[2-(4-Methylpiperizin-1-yl)ethyl]-2-methylphenyl}-[4(1H-pyrrolo[2,3-b]pyridin-3-yl)-pyrimidin-2-yl]-amine (51)

Using the procedure of example 19, compound 45a (80 mg) was reacted with 1-methyl-piperazine (94 mg) to provide compound 51 (79 mg, 98%). $^1$H NMR (400 MHz, CD$_3$OD) δ 8.55 (d, 1H), 8.22 (m, 3H), 7.45 (d, 1H), 7.20 (s, 1H), 7.15 (d, 1H), 7.12 (m, 1H), 7.05 (m, 1H), 4.60 (m, 2H), 2.85 (m, 4H), 2.70 (m, 4H), 2.60 (m, 2H), 2.35 (s, 3H), 2.30 (s, 3H).
MS (ESI) m/z: 428 (M+H)$^+$.

EXAMPLE 52

[4-(2-Hydroxyethyl)-2-chlorophenyl)]-[4-(1H-pyrrolo[2,3-b]pyridin-3-yl)-pyrimidin-2-yl]-amine (52)

Using the procedure of example 44, compound 1g (141 mg) was reacted with 2-chloro-4-(2-hydroxyethyl)aniline (210 mg) to generate compound 52 (83 mg, 37%). $^1$H NMR (400 MHz, DMSO) δ 12.30 (br s, 1H), 8.67 (s, 1H), 8.60 (d, 1H), 8.46 (s, 1H), 8.35 (d, 1H), 8.30 (m, 1H), 7.80 (s, 1H), 7.45 (d, 1H), 7.35 (d, 1H), 7.13 (dd, 1H), 7.08 (d, 1H), 4.68 (s, 1H), 3.68 (t, 2H), 2.80 (t, 2H). MS (ESI) m/z: 366 (M+H)$^+$.

EXAMPLE 53

[2-Chloro-4-(2-methylaminoethyl)phenyl)]-[4-(1H-pyrrolo[2,3-b]pyridin-3-yl)-pyrimidin-2-yl]-amine (53)

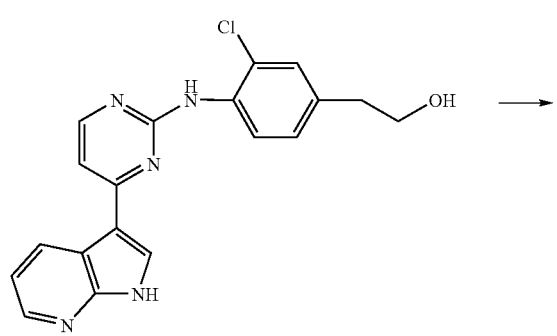

52

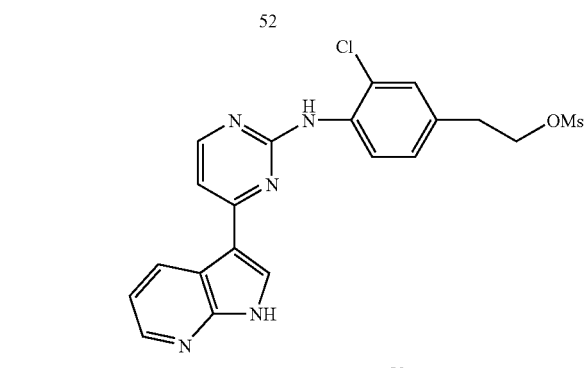

53a

Using the procedure of example 19, compound 52 (345 mg) was reacted with methanesulfonyl chloride (216 mg) to provide compound 53a (420 mg, 100%). $^1$H NMR (400 MHz, CDCl$_3$/CD$_3$OD) δ 8.73 (d, 1H), 8.52 (s, 1H), 8.41 (d, 1H), 8.32 (d, 1H), 8.13 (s, 1H), 7.41 (d, 1H), 7.25 (dd, 1H), 7.18 (d, 1H), 6.92 (d, 1H), 4.47 (t, 2H), 3.11 (t, 2H), 2.92 (3, 3H). MS (ESI) m/z: 444 (M+H)$^+$.

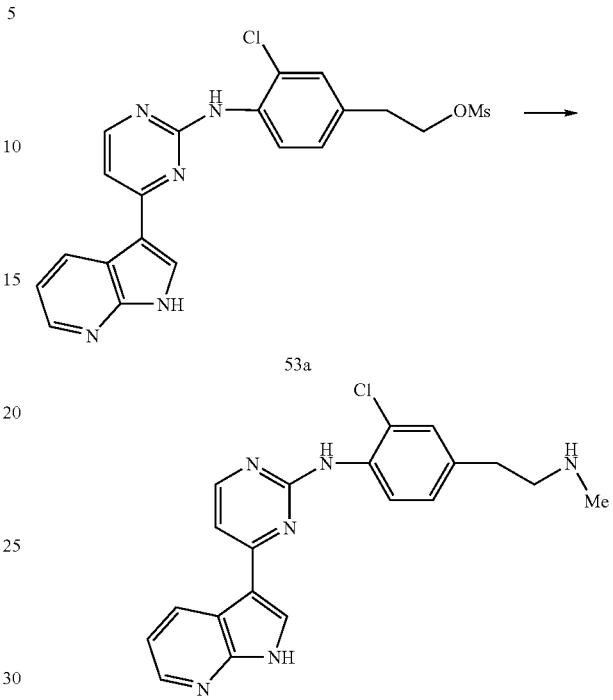

53a

53

Using the procedure of example 19, compound 53a (50 mg) was reacted with methylamine (17 mg) to provide compound 53 (40 mg, 94%). $^1$H NMR (400 MHz, CD$_3$OD/CDCl$_3$) δ 8.70 (d, 1H), 8.33 (d, 1H), 8.30 (s, 1H), 8.24 (d, 1H), 8.20 (s, 1H), 7.40 (d, 1H), 7.28 (d, 1H), 7.18 (dd, 1H), 6.95 (d, 1H), 4;35 (t, 2H), 2.78 (t, 2H), 2.60 (s, 3H). MS (ESI) m/z: 379 (M+H)$^+$.

EXAMPLE 54

[2-Chloro-4-(2-dimethylaminoethyl)phenyl)]-[4-(1H-pyrrolo[2,3-b]pyridin-3-yl)-pyrimidin-2-yl]-amine (53)

Using the procedure of example 19, compound 53a (50 mg) was reacted with dimethylamine (26 mg) to provide compound 54 (32 mg, 72%). $^1$H NMR (400 MHz, CD$_3$OD) δ 8.68 (d, 1H), 8.32 (d, 1H), 8.28 (d, 1H), 8.25 (s, 1H), 8.13 (s, 1H), 7.42 (d, 1H), 7.30 (d, 1H) 7.20 (dd, 1H), 7.02 (d, 1H), 2.85 (t, 2H), 2.65 (t, 2H), 2.30 (s, 6H). MS (ESI) m/z: 393 (M+H)$^+$.

EXAMPLE 55

{2-Chloro-4-[2-(4-methylpiperizin-1-yl)ethyl]phenyl}-[4-(1H-pyrrolo[2,3-b]pyridin-3-yl)-pyrimidin-2-yl]-amine (55)

Using the procedure of example 19, compound 53a (50 mg) was reacted with 1-methyl-piperazine (57 mg) to provide compound 55 (46 mg, 91%). $^1$H NMR (400 MHz, CD$_3$OD) δ 8.65 (d, 1H), 8.33 (d, 1H), 8.28 (d, 1H), 8.26 (s, 1H), 8.14 (s, 1H), 7.40 (d, 1H), 7.25 (d, 1H), 7.18 (dd, 1H), 7.02 (d, 1H), 2.85 (m, 4H), 2.65 (m, 4H), 2.50 (m, 4H), 2.26 (s, 3H).
MS (ESI) m/z: 448 (M+H)$^+$.

EXAMPLE 56

{2-Chloro-4-[2-(morpholin-4-yl)ethyl]phenyl}-[4-(1H-pyrrolo[2,3-b]pyridin-3-yl)-pyrimidin-2-yl]-amine (56)

Using the procedure of example 19, compound 53a (50 mg) was reacted with morpholine (50 mg) to provide compound 56 (47 mg, 96%). $^1$H NMR (400 MHz, CD$_3$OD) δ 8.70 (d, 1H), 8.35 (d, 1H), 8.30 (d, 1H), 8.29 (s, 1H), 8.15 (s, 1H), 7.42 (d, 1H), 7.30 (d, 1H), 7.20 (dd, 1H), 7.05 (d, 1H), 3.68 (m, 4H), 3.60 (t, 4H), 2.50 (m, 4H). MS (ESI) m/z: 435 (M+H)$^+$.

EXAMPLE 57 trans-N-[4-(2-Methyl-1H-pyrrolo[2,3-b]pyridin-3-yl)-pyrimidin-2-yl]-cyclohexane-1,4-diamine (57)

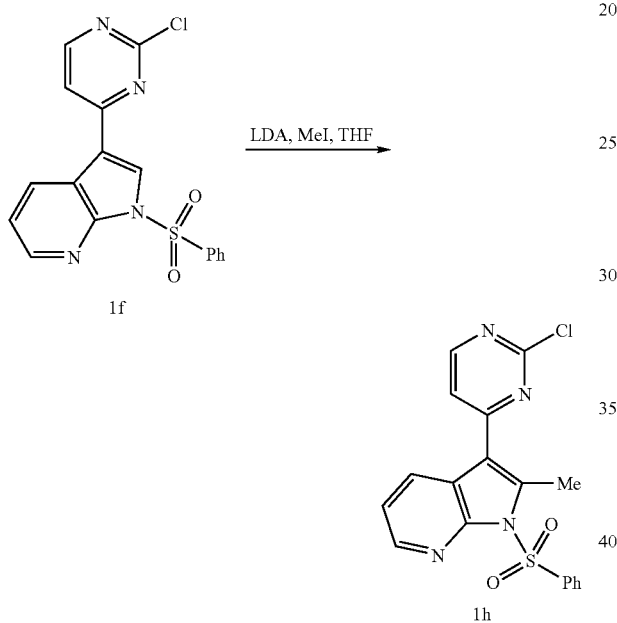

To the solution of compound 1f (1.0 g) in THF (20 mL) was added LDA (1 M solu in THF, 3.2 mL) at −78° C., followed by addition of iodomethane. (0.76 g) one hour later. After being stirred at −78° C. for 3 hr, the mixture was warmed to rt, then poured into water and extracted with EtOAc. The organic layer was separated, dried with MgSO$_4$, then concentrated and the residue was pyrified by flash chromatography [silica gel, 1% NH$_3$ (1 M in MeOH) in DCM to afford 0.26 g (25%) of the desired compound 1h. MS (ESI) m/z: 385 (M+H)$^+$.

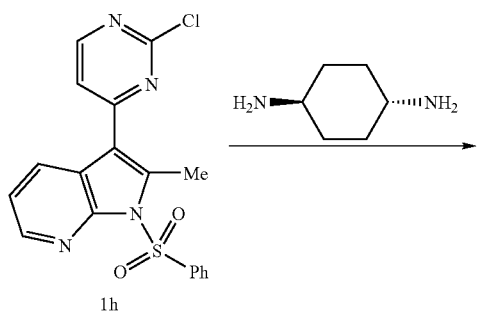

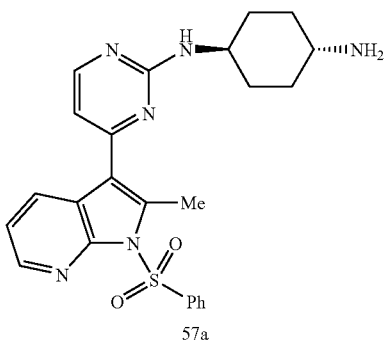

Using the procedure of example 1, compound 1h (430 mg) was reacted with trans-1,4-cyclohexyldiamine (382 mg) to provide compound 57a (258 mg, 50%). MS (ESI) m/z: 463 (M+H)$^+$.

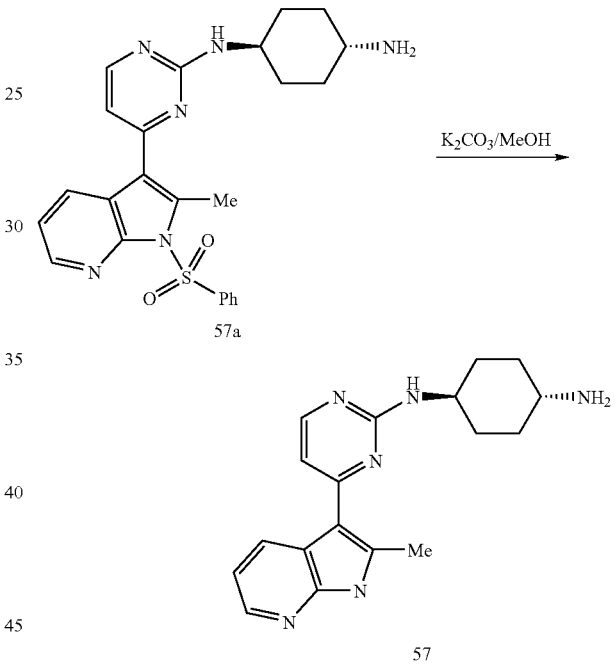

Compound 57a (140 mg) was heated to 100° C. in the presence potassium carbonate (84 mg) in methanol for 3 hrs to generate compound 57 (37 mg, 38%). $^1$H NMR (400 MHz, CD$_3$OD) δ 8.56 (d, 1H), 8.20 (d, 1H), 8.15 (m, 1H), 7.17 (dd, 1H), 6.90 (d, 1H), 3.87 (m, 2H), 2.21 (m, 2H), 2.08 (m, 2H), 1.48 (m, 4H). MS (ESI) m/z: 323 (M+H)$^+$.

EXAMPLE 58

(2R)-Bicyclo[2.2.1]hept-2-yl-[4-(1H-pyrrolo[2,3-b]pyridin-3-yl)-pyrimidin-2-yl]-amine (58)

Using the procedure of example 1, endo-2-norbornylamine (228 mg) was reacted with compound 1f (253 mg) to provide compound 58 (18 mg, 8.7%). $^1$H NMR (300 MHz, CD$_3$OD) δ 8.95 (d, 1H), 8.23 (d, 1H), 8.15 (s, 1H), 8.08 (d, 1H), 7.20 (m, 1H), 6.95 (d, 1H), 3.85 (m, 1H), 2.40 (m, 1H), 2.35 (m, 1H), 1.85 (m, 1H), 1.6 (m, 3H), 1.45 (m, 2H), 1.20 (m, 2H). MS (ESI) m/z: 304 (M+H)$^+$.

EXAMPLE 59

(2S)-Bicyclo[2.2.1]hept-2-yl-[4-(1H-pyrrolo[2,3-b]pyridin-3-yl)-pyrimidin-2-yl]-amine (59)

Using the procedure of example 1, exo-2-norbornylamine (189 mg) was reacted with compound 1f (210 mg) to provide compound 59 (140 mg, 82%). $^1$H NMR (300 MHz, CD$_3$OD) δ 8.95 (d, 1H), 8.23 (d, 1H), 8.15 (s, 1H), 8.08 (d, 1H), 7.20 (m, 1H), 6.95 (d, 1H), 2.61 (m, 1H), 2.20 (m, 2H), 1.75 (m, 1H), 1.55 (m, 1H), 1.40 (m, 3H), 1.20 (m, 2H), 1.05 (m, 1H). MS (ES) m/z: 304 (M+H)$^+$.

EXAMPLE 60

(Tetrahydropyran-4-yl)-[4-(1H-pyrrolo[2,3-b]pyridin-3-yl)-pyrimidin-2-yl]-amine (60)

Using the procedure of example 1, tetrahydropyran-4-ylamine (0.8 g) was reacted with compound 1f (1.8 g) to provide compound 60 (1.2 g, 42%). $^1$H NMR (400 MHz, DMSO) δ 12.20 (s, 1H), 8.95 (s, 1H), 8.39 (s, 1H), 8.30 (d, 1H), 8.15 (d, 1H), 7.20 (m, 1 H), 7.06 (d, 1H), 7.04 (d, 1H), 4.00 (m, 1H), 3.90 (m, 2H), 3.45 (m, 2H), 1.90 (m, 2 H), 1.55 (m, 2H).
MS (ESI) m/z: 296 (M+H)$^+$.

EXAMPLE 61

(1-Methylpiperidin-4-yl)-[4-(1H-pyrrolo[2,3-b]pyridin-3-yl)-pyrimidin-2-yl]-amine (61)

Using the procedure of example 1, 1-methylpiperidin-4-ylamine (30 mg) was reacted with compound 1f (30 mg) to provide compound 61 (10.2 mg, 41%). $^1$H NMR (300 MHz, CD$_3$OD) δ 8.92 (d, 1 H), 8.23 (d, 1 H), 8.15 (s, 1 H), 8.10 (d, 1 H), 7.25 (m, 1 H), 7.00 (d, 1 H), 3.96 (m, 1 H), 3.05 (m, 2 H), 2.45 (m, 2 H), 2.15 (m, 2 H), 1.95 (s, 3 H), 1.75 (m, 2H). MS (ESI) m/z: 309 (M+H)$^+$.

EXAMPLE 62

1-[4-(1H-pyrrolo[2,3-b]pyridin-3-yl)-pyrimidin-2-yl]-piperidin-4-ylamine (62)

Using the procedure of example 1, piperidin-4-ylamine (540 mg) was reacted with compound 1f (500 mg) to provide compound 62 (285 mg, 72%). $^1$H NMR (400MHz, DMSO) δ 8.70 (d, 1 H), 8.40 (s, 1 H), 8.25 (m, 1 H), 8.20 (d, 1 H), 7.20 (m, 1 H), 7.05 (d, 1 H), 4.60 (d, 2 H), 3.05 (m, 2 H), 2.85 (m, 1 H), 1.85 (m, 2 H), 1.25 (m, 2 H). MS (ESI) m/z: 295 (M+H)$^+$.

EXAMPLE 63

N-{1-[4-(1H-pyrrolo[2,3-b]pyridin-3-yl)-pyrimidin-2-yl]-piperidin-4-yl}acetamide (63)

To a flask was added compound 62 (10.2 mg), acetic anhydride (0.5 mg), pyridine (0.1 mL) and THF (1 mL) at 0° C. The mixture was warmed to rt slowly and stirred for 1 hr, then poured into water and extracted with EtOAc. The organic layer was separated, dried with MgSO$_4$, then concentrated to provide 10.9 mg (94%) of the desired product as a white solid. $^1$H NMR (400 MHz, DMSO) δ 12.30 (s, 1 H), 8.70 (d, 1 H), 8.40 (s, 1 H), 8.25 (m, 1 H), 8.20 (d, 1 H), 7.80 (d, 1 H), 7.25 (m, 1 H), 7.10 (d, 1 H), 4.60 (d, 2 H), 3.90 (m, 1 H), 3.15 (m, 2 H), 1.85 (m, 2 H), 1:80 (s, 3 H), 1.40 (m, 2 H). MS (ESI) m/z: 337 (M+H)$^+$.

EXAMPLE 64

1-{4-[4-(1H-pyrrolo[2,3-b]pyridin-3-yl)pyrimidin-2-ylamino]piperidin-1-yl}ethanone (64)

Using the procedure of example 1, 1-(4-aminopiperidin-1-yl)ethanone (350 mg) was reacted with compound 1f (300 mg) to provide compound 64 (33 mg, 12%). $^1$H NMR (300 MHz, CDCl$_3$) δ 11.45 (s, 1 H), 8.75 (d, 1 H), 8.40 (d, 1 H), 8.20 (d, 1 H), 8.12 (s, 1 H), 8.00 (s, 1 H), 7.20 (m, 1H), 6.90 (d, 1 H), 5.40 (m, 1 H) (rotamer), 4.55 (m, 1 H), 4.20-3.70 (m, 2 H), 3.40-2.70 (m, 2 H), 2.20 (m, 2 H), 2.15 (s, 3 H), 1.50 (m, 2H). MS (ESI) m/z: 337 (M+H)$^+$.

EXAMPLE 65

Piperidin-4-yl-[4-(1H-pyrrolo[2,3-b]pyridin-3-yl)pyrimidin-2-yl]-amine (65)

To a flask was added compound 64 (20 mg) and 1 M aqueous NaOH (1 mL). The mixture was heated to 100° C. for 3 hrs. After being neutralized with acetic acid, the solution was concentrated and the residule was purified by reverse phase HPLC to afford 33 mg (71%) of the desired product. $^1$H NMR (300 MHz, CD$_3$OD) δ 8.85 (m, 1 H), 8.60 (s, 1 H), 8.35 (d, 1 H), 8.10 (d, 1 H), 7.35 (m, 2 H), 4.40 (m, 1 H), 3.50 (m, 2 H), 3.30 (m, 2 H), 2.40 (m, 2 H), 1.95 (m, 2 H). MS (ESI) m/z: 295 (M+H)$^+$.

EXAMPLE 66

Cyclohexyl-[4-(1-methyl-1H-pyrrolo[2,3-b]pyridin-3-yl)pyrimidin-2-yl]-amine (66)

Compound 13 (24 mg) was dissolved in THF (1 mL) and KO$_t$Bu (1 M in THF, 82 μL) was added. The mixture was stirred for 1 hr, followed by addition of methyl iodide (5.1 μL). The stirring was continued for additional 1 hr, then the solution was concentrated and the residue was purified by flash chromatography [silica gel, EtOAc] to afford 16 mg (82%) of the desired product. $^1$H NMR (400 MHz, CDCl$_3$) δ 8.65 (d, 1 H), 8.32 (d, 1 H), 8.13 (d, 1 H), 7.75 (s, 1 H), 7.15 (dd, 1 H), 6.71 (d, 1 H), 5.0 (m, 1 H), 3.90 (s, 3 H), 3.88 (m, 1 H), 2.10 (m, 2 H), 1.70 (m, 2 H), 1.60 (m, 2 H), 1.40 (m, 2 H), 1.20 (m, 2 H). MS (ESI) m/z: 308 (M+H)$^+$.

EXAMPLE 67

Cyclohexyl-[4-(1-methanesulfonyl-1H-pyrrolo[2,3-b]pyridin-3-yl)pyrimidin-2-yl]-amine (67)

Using the procedure of example 66, compound 13 (24 mg) and methanesulfonyl chloride (9.4 mg) were used to provide compound 67 (28 mg, 91%). $^1$H NMR (400 MHz, CDCl$_3$) δ 8.85 (d, 1 H), 8.52 (d, 1 H), 8.32 (d, 1 H), 8.28 (s, 1 H), 7.40 (dd, 1 H); 6.85 (d, 1H), 5.12 (m, 1 H), 3.90 (m, 1 H), 3.65 (s, 3 H), 2.15 (m, 2 H), 1.85 (m, 2 H), 1.65 (m, 2 H), 1.50 (m, 2 H), 1.35 (m, 2 H). MS (ESI) m/z: 372 (M+H)+.

EXAMPLE 68

Cyclohexyl-[4-(1-acetyl-1H-pyrrolo[2,3-b]pyridin-3-yl)pyrimidin-2-yl]-amine (68)

Using the procedure of example 66, compound 13 (24 mg) and acetic anhydride (7.7 µL) were used to provide compound 68 (24 mg, 86%). $^1$H NMR (300 MHz, CDCl$_3$) δ 8.85 (d, 1 H), 8.52 (d, 1 H), 8.40 (d, 1 H), 8.28 (d, 1 H), 7.35 (dd, 1 H), 6.90 (d, 1 H), 5.15 (m, 1 H), 3.92 (m, 1 H), 2.15 (m, 2 H), 1.85 (m, 2 H), 1.70 (m, 2 H), 1.50 (m, 2 H), 1.30 (m, 2 H). MS (ESI) m/z: 336 (M+H)+.

EXAMPLE 69

Cyclohexyl-{4-[1-(2-dimethylaminoethyl)-1H-pyrrolo[2,3-b]pyridin-3-yl]-pyrimidin-2-yl}-amine (69)

Compound 13 (25 mg) was dissolved in DMF (1 mL) and NaH (5 mg) was added. The mixture was stirred for 1 hr, followed by addition of 2-(dimethylamino)ethyl chloride hydrochloride (10 mg). After being warmed to 45° C. for 2 hrs, the solution was concentrated and the residue was purified by flash chromatography [silica gel, DCM:MeOH/9.5:0.5] to afford 13 mg (42%) of the desired product. $^1$H NMR (400 MHz, CDCl$_3$) δ 8.72 (d, 1 H), 8.35 (d, 1 H), 8.18 (d, 1 H), 7.92 (s, 1 H), 7.15 (dd, 1 H), 6.80 (d, 1 H), 5.01 (d, 1 H), 4.45 (t, 2 H), 3.95 (m, 1 H), 2.80 (t, 2 H), 2.32 (s, 6 H), 2.15 (m, 2 H), 1.80 (m, 2 H), 1.70 (m, 2 H), 1.45 (m, 2 H), 1.30 (m, 2 H). MS (ESI) m/z: 365 (M+H)+.

EXAMPLE 70

Cyclohexyl-{4-[1-(2-hydroxyethyl)-1H-pyrrolo[2,3-b]pyridin-3-yl]-pyrimidin-2-yl}-amine (70)

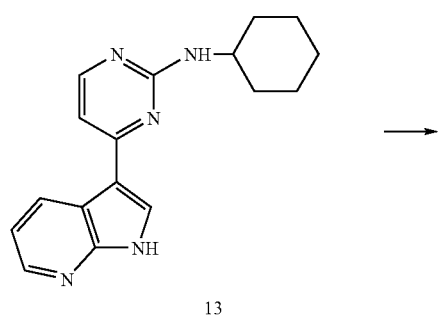

13

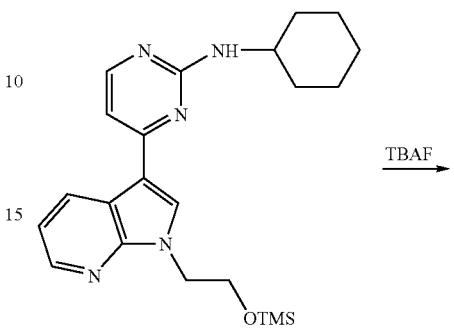

70a

Using the procedure of example 66, compound 13 (40 mg) and 2-chloroethoxytrimethylsilane (21 mg) were used to provide 19 mg (35%) of compound 70a.

MS (ESI) m/z: 410 (M+H)+.

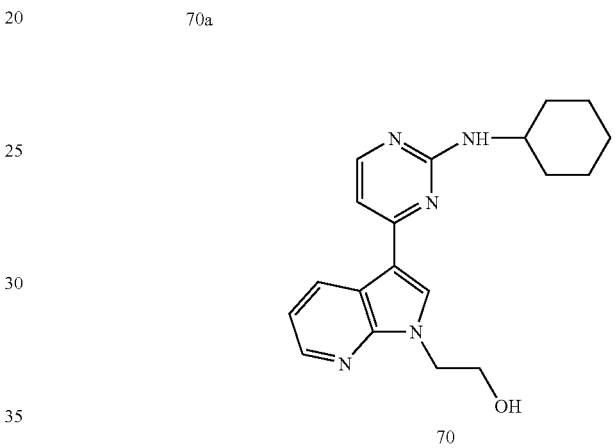

70

Compound 70a (10.3 mg) was treated with TBAF to provide 8.5 mg (100%) of compound 70. $^1$H NMR (300 MHz, CDCl$_3$) δ 8.80 (d, 1 H), 8.32 (d, 1 H), 8.20 (d, 1 H), 7.85 (s, 1 H), 7.20 (dd, 1 H), 6.80 (d, 1 H), 5.05 (m, 1 H), 4.50 (t, 2 H), 4.05 (t, 2 H), 3.95 (m, 1 H), 2.15 (m, 2 H), 1.80 (m, 2 H), 1.60 (m, 2 H), 1.50 (m, 2 H), 1.30 (m, 2 H). MS (ESI) m/z: 338 (M+H)+.

EXAMPLE 71 trans-4-[4-(1-Methyl-1H-pyrrolo[2,3-b]pyridin-3-yl)-pyrimidin-2-ylamino]-cyclohexanol (71)

To a flask was added compound 18 (17 mg), methyl iodide (7.8 mg), K$_2$CO$_3$ (10 mg), and DMF (1 mL). The mixture was heated to 50° C. for 2 hrs, then poured into water and extracted with EtOAc. The organic layer was separated, dried with MgSO$_4$, then concentrated and the residue was purified by flash chromatography [DCM:MeOH/9.5:0.5] to afford 14 mg (82%) of the desired product. $^1$H NMR (300 MHz, CDCl$_3$) δ 8.70 (d, 1 H), 8.40 (d, 1 H), 8.20 (d, 1 H), 7.85 (s, 1 H), 7.20 (dd, 1 H), 6.80 (d, 1 H), 5.00 (m, 1 H), 4.30 (m, 1 H), 3.96 (s, 3 H), 3.70 (m, 1 H), 2.30 (m, 2 H), 2.10 (m, 2 H), 1.70 (br s, 1 H), 1.50 (m, 2 H), 1.35 (m, 2 H). MS (ESI) m/I: 324 (M+H)+.

EXAMPLE 72 trans-4-{4-[1-(2-Hydroxyethyl)-1H-pyrrolo[2,3-b]pyridin-3-yl]-pyrimidin-2-ylamino}-cyclohexanol (72)

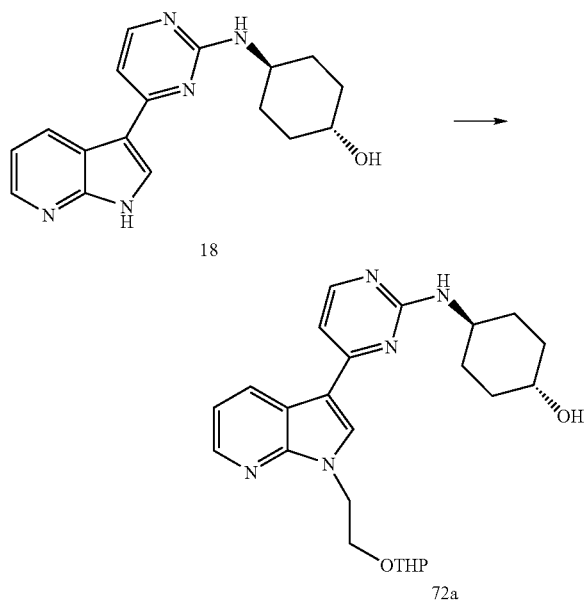

To a flask was added compound 18 (110 mg), 2-(2-bromoethoxy)tetrahydropyran (74 mg), K$_2$CO$_3$ (20 mg) and DMF (5 mL). The mixture was heated to 90° C. overnight, then poured into water and extracted with EtOAc. The organic layer was separated, dried with MgSO$_4$, then concentrated and the residue was purified by flash chromatography [silica gel, DCM:MeOH/9.5:0.5] to provide 65 mg (52%) of compound 72a. MS (ESI) m/z: 438 (M+H)$^+$.

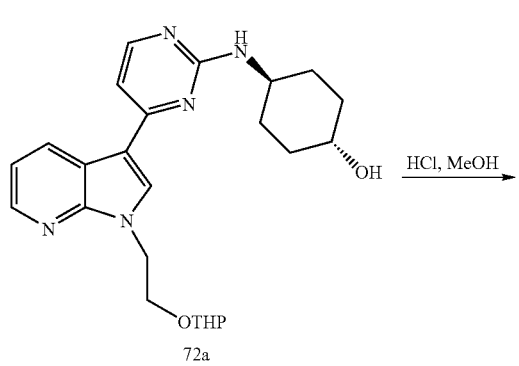

Compound 72a (40 mg) was treated with conc. HCl in MeOH to provide 30 mg (93%) of compound 72. $^1$H NMR (300 MHz, CDCl$_3$) δ 8.75 (d, 1 H), 8.35 (d, 1 H), 8.15 (d, 1 H), 7.82 (s, 1 H), 7.20 (dd, 1 H), 6.80 (d, 1 H), 5.00 (m, 1 H), 4.50 (t, 2 H), 4.10 (t, 2 H), 3.95 (m, 1 H), 3.70 (m, 1 H), 2.25 (m, 2 H), 2.05 (m, 2H), 1.70 (br s, 1 H), 1.50 (m, 2 H), 1.35 (m, 2 H). MS (ESI) m/z: 354 (M+H)$^+$.

EXAMPLE 73 trans-4-{4-[1-(2-Methylaminoethyl)-1H-pyrrolo[2,3-b]pyridin-3-yl]-pyrimidin-2-ylamino}-cyclohexanol (73)

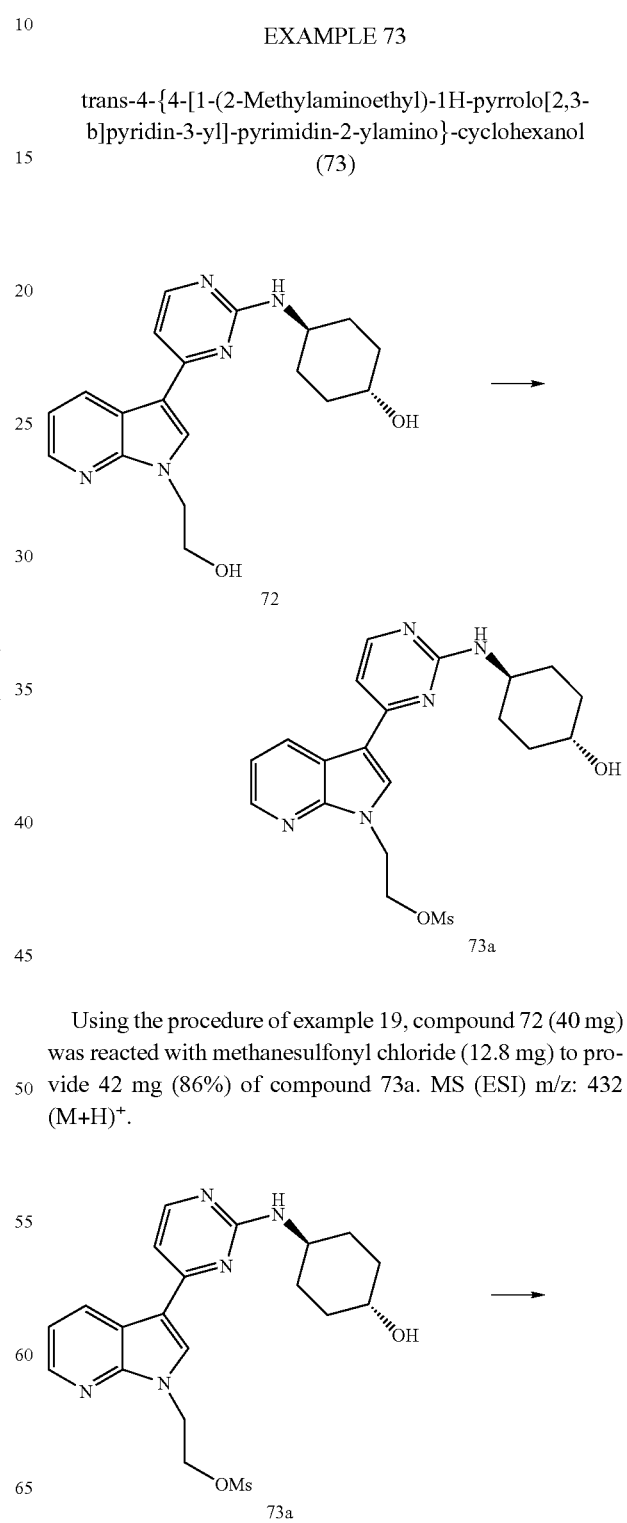

Using the procedure of example 19, compound 72 (40 mg) was reacted with methanesulfonyl chloride (12.8 mg) to provide 42 mg (86%) of compound 73a. MS (ESI) m/z: 432 (M+H)$^+$.

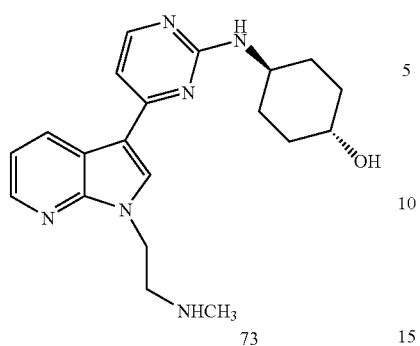

73

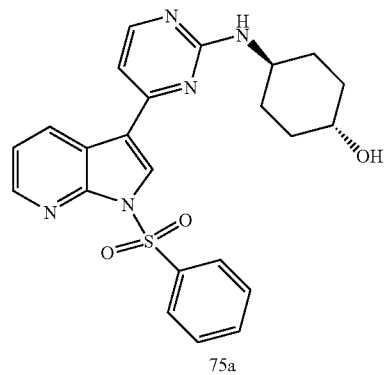

75a

Using the procedure of example 19, compound 73a (10 mg) was reacted with methylamine (1 M in THF, 0.1 mL) to afford 7.0 mg (82%) of compound 73. $^1$H NMR (300 MHz, CDCl$_3$) δ 8.65 (d, 1 H), 8.30 (d, 1 H), 8.15 (d, 1 H), 7.85 (s, 1 H), 7.15 (dd, 1 H), 6.80 (d, 1 H), 4.92 (m, 1 H), 4.65 (m, 1 H), 4.45 (t, 2 H), 3.92 (m, 1 H), 3.10 (t, 2 H), 2.45 (s, 3 H), 2.20 (m, 4 H), 1.80 (m, 2 H), 1.40 (m, 2 H). MS (ESI) m/z: 367 (M+H)$^+$.

EXAMPLE 74 trans-4-{4-[1-(2-Dimethylaminoethyl)-1H-pyrrolo[2,3-b]pyridin-3-yl]-pyrimidin-2-ylamino}-cyclohexanol (74)

Using the procedure of example 19, compound 73a (10 mg) was reacted with dimethylamine (1 M in THF, 0.1 mL) to afford 7.0 mg (81%) of compound 74. $^1$H NMR (400 MHz, CDCl$_3$) δ 8.70 (d, 1 H), 8.37 (d, 1 H), 8.18 (d, 1 H), 7.98 (s, 1 H), 7.19 (dd, 1 H), 6.85 (d, 1 H), 5.05 (m, 1 H), 4.75 (m, 1 H), 4.45 (t, 2 H), 4.00 (m, 2 H), 2.80 (t, 2 H), 2.35 (s, 6 H), 2.30 (m, 4 H), 1.80 (m, 2 H), 1.45 (m 2 H). MS (ESI) m/z: 381 (M+H)$^+$.

EXAMPLE 75 trans-4-[4-(1-Benzenesulfonyl-1H-pyrrolo[2,3-b]pyridin-3-yl)-pyrimidin-2-ylamino]-cyclohexanol (75)

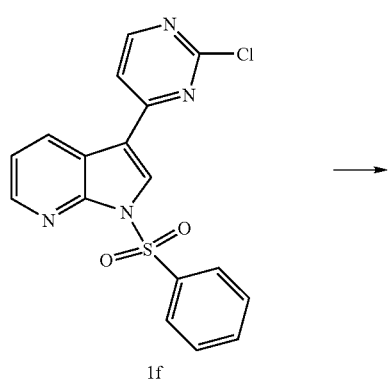

1f

Using the procedure of example 1, compound 1f (1.0 g) was reacted with trans-4-aminocyclohexanol (2.2 g) to provide 0.75 g (62%) of compound 75a. $^1$H NMR (400 MHz, CDCl$_3$) δ 8.70 (d, 1 H), 8.50 (d, 1 H), 8.30 (d, 2 H), 8.27 (d, 1 H), 7.60 (d, 1 H), 7.50 (t, 2 H), 7.25 (dd, 1 H), 6.87 (d, 1 H), 5.01 (m, 1 H), 3.92 (m, 1 H), 3.70 (m, 1 H), 2.25 (m, 2 H), 2.05 (m, 2 H), 1.50 (m, 2 H), 1.35 (m, 2 H). MS (ESI) m/z 450 (M+H)$^+$.

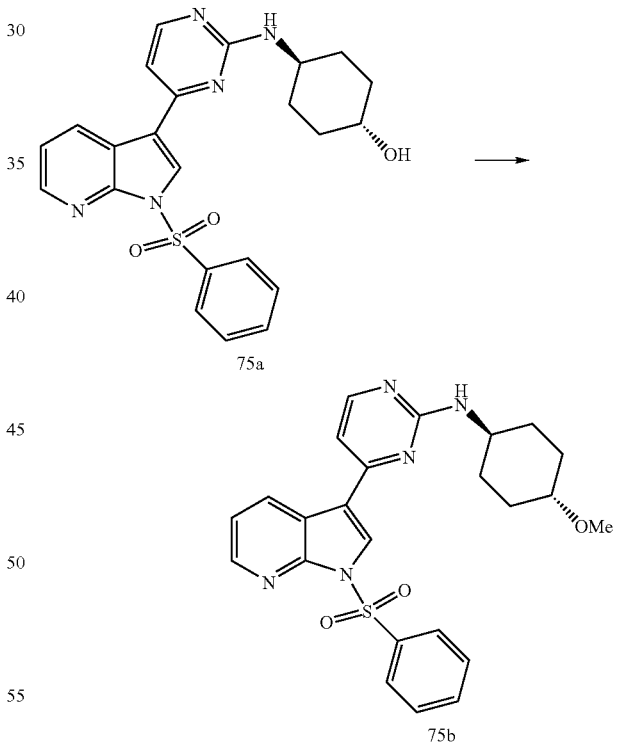

Compound 75a (60 mg) was dissolved in THF (2 mL) and KO$_t$Bu (1 M in THF, 1.33 mL) was added. After 30 minutes, methyl iodide (9.1 μL) was added. The mixture was stirred for another 30 minutes, then poured into water and extracted with EtOAc. The organic layer was separated, dried with MgSO$_4$, then concentrated and the residue was purified by flash chromatography [silica gel, DCM:MeOH/9.5:0.5] to afford 48 mg (78%) of compound 75b. MS (ESI) m/z: 464 (M+H)$^+$.

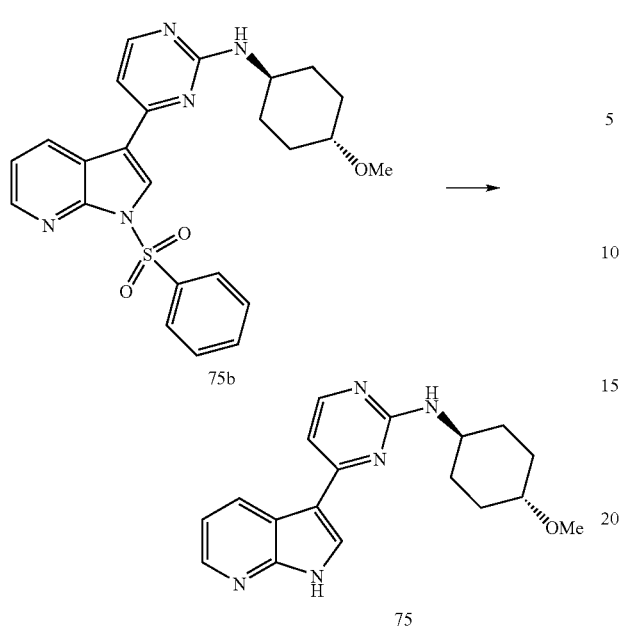

Using the procedure of example 57, compound 75b (50 mg) was treated with K₂CO₃ (20 mg) in MeOH to afford 30 mg (86%) of compound 75. ¹H NMR (400 MHz, CDCl₃) δ 8.70 (d, 1 H), 8.40 (d, 1 H), 8.20 (d, 1 H), 7.80 (s, 1 H), 7.15 (dd, 1 H), 6.80 (d, 1 H), 5.70 (m, 2 H), 5.15 (m, 1 H), 4.25 (m, 1 H), 3.95 (s, 3 H), 2.55 (m, 1 H), 2.25 (m, 2 H), 2.10 (m, 2 H), 1.90 (m, 1 H), 1.75 (m, 1 H). MS (ESI) m/z: 306 (M+H)⁺.

EXAMPLE 76 trans-4-{4-[1-(3-Dimethylamino-2-hydroxy-propyl)-1H-pyrrolo[2,3-b]pyridin-3-yl]-pyrimidin-2-ylamino}-cyclohexanol (76)

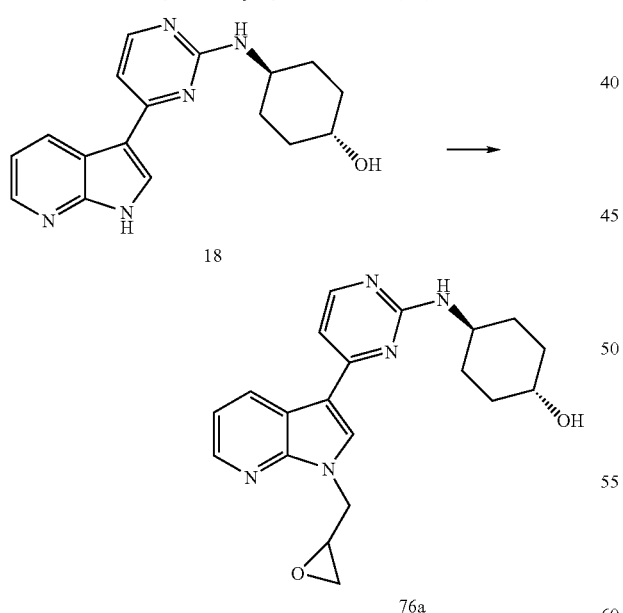

To a flask was added compound 18 (60 mg), epibromohydrin (26.6 mg), K₂CO₃ (200 mg) and DMF (3 mL). After being heated to 70° C. for 2 hrs, the solution was poured into water, then extracted with EtOAc. The organic layer was separated, dried with MgSO₄, then concentrated. The residue was purified by flash chromatography [silica gel, DCM:MeOH/9.5:0.5] to afford 48 mg (68%) of compound 76a. ¹H NMR (300 MHz, CDCl₃) δ 8.80 (d, 1 H), 8.35 (d, 1 H), 8.20 (d, 1 H), 7.90 (s, 1 H), 7.20 (dd, 1 H), 6.85 (d, 1 H), 5.00 (m, 1 H), 4.80 (d, 1 H), 4.30 (dd, 1 H), 3.95 (m, 1 H), 3.75 (m, 1 H), 3.35 (m, 1 H), 2.85 (m, 1 H), 2.50 (m, 1 H), 2.30 (m, 2 H), 2.10 (m, 2 H), 1.70 (br s, 1 H), 1.50 (m, 2 H), 1.35 (m, 2 H). MS (ESI) m/z: 366 (M+H)⁺.

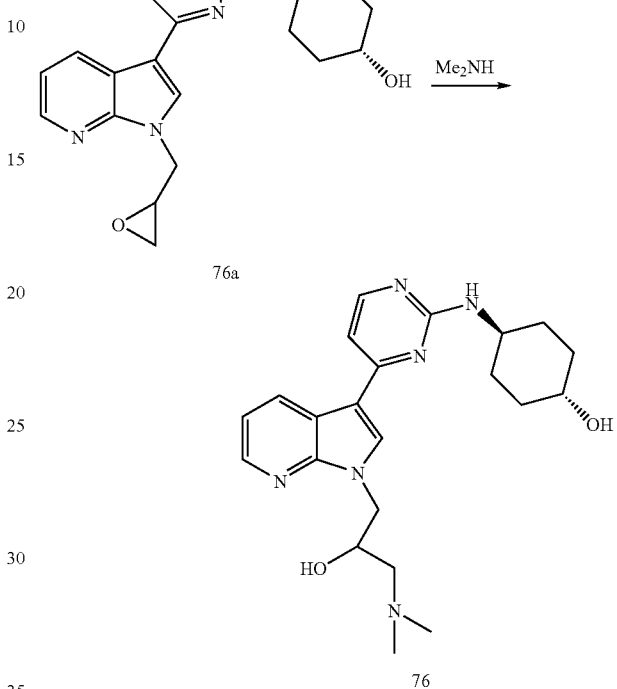

To a screw cap tube was added compound 76a (10 mg), dimethylamine (2 M in THF, 14 μL) and 1,4-dioxane (1 mL). The mixture was heated to 90° C. for 4 hrs, then concentrated and the residue was purified by flash chromatography [silica gel, DCM:2 M ammonium in MeOH/9:1] to afford 8 mg (72%) of compound 76. ¹H NMR (300 MHz, CDCl₃) δ 8.65 (d, 1 H), 8.22 (d, 1 H), 8.10 (d, 1 H), 7.93 (s, 1 H), 7.15 (dd, 1 H), 6.75 (d, 1 H), 4.90 (m, 1 H), 4.50 (dd, 1 H), 4.30 (dd, 1 H), 4.10 (m, 1 H), 3.91 (m, 1 H), 3.65 (m, 1 H), 2.35 (dd, 1 H), 2.30 (s, 6 H), 2.20 (m, 2 H), 2.05 (m, 2 H), 1.70 (br s, 1 H), 1.50 (m, 2 H), 1.30 (m, 2 H).
MS (ESI) m/z: 411 (M+H)⁺.

EXAMPLE 77 trans-2-{4-[4-(1H-pyrrolo[2,3-b]pyridin-3-yl)-pyrimidin-2-ylamino]-cyclohexyl}-ethanol (77)

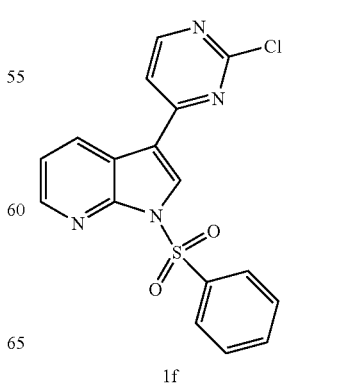

-continued

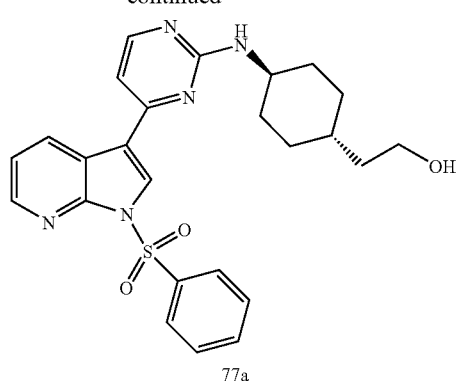

77a

Using the procedure of example 1, compound 1f (1.86 g) was reacted with 2-(4-aminocyclohexyl)ethanol (0.72 g) to provide 1.1 g (48%) of compound 77a. $^1$H NMR (400 MHz, CDCl$_3$) δ 8.70 (d, 1 H), 8.40 (d, 1 H), 8.30 (s, 1 H), 8.26 (d, 1 H), 8.20 (d, 2 H), 7.55 (d, 1 H), 7.50 (t, 2 H), 7.25 (t, 2 H), 6.85 (d, 1 H), 5.15 (m, 1 H), 3.85 (m, 1 H), 3.70 (t, 2 H), 2.20 (m, 2 H), 1.85 (m, 2 H), 1.50 (m, 2 H), 1.49 (m, 1 H), 1.25 (m, 2 H), 1.15 (m, 2 H). MS (ESI) m/z: 478 (M+H)$^+$.

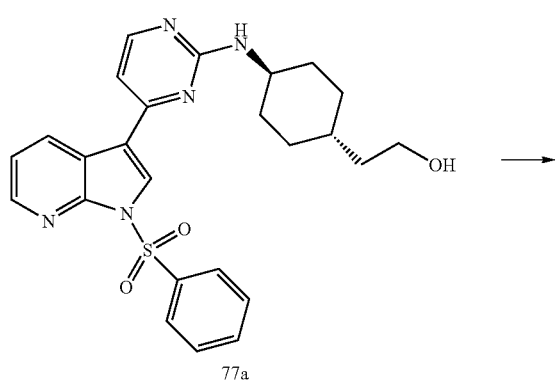

Using the procedure of example 56, compound 77a (1.0 g) was treated with K$_2$CO$_3$ (0.5 g) in MeOH to afford 0.58 (82%) of compound 77. $^1$H NMR (300 MHz, DMSO) δ 12.20 (s, 1H), 8.90 (br s, 1 H), 8.35 (d, 1 H), 8.29 (m, 1 H), 8.10 (d, 1 H), 7.15 (m, 1 H), 7.00 (d, 1 H), 6.80 (d, 1 H), 4.35 (t, 1 H), 3.70 (m, 1 H), 3.45 (m, 2 H), 2.00 (m, 2 H), 1.80 (m, 2 H), 1.40-1.10 (m, 7 H). MS (ESI) m/z: 338 (M+H)$^+$.

EXAMPLE 78 trans-[4-(2-Methylaminoethyl)-cyclohexyl]-[4-(1H-pyrrolo[2,3-b]pyridin-3-yl)-pyrimidin-2-yl]-amine (78)

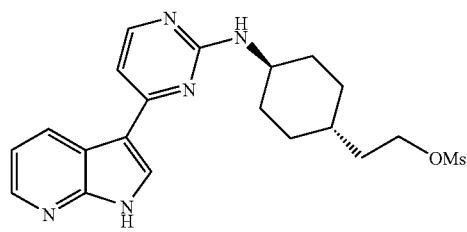

77

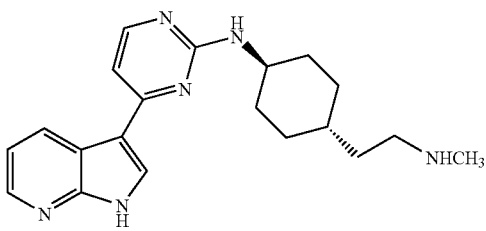

78a

Using the procedure of example 19, compound 77 (0.46 g) was reacted with methanesulfonyl chloride (0.13 mL) to provide 0.50 g (88%) of compound 78a. MS (ESI) m/z: 416 (M+H)$^+$.

78a →CH$_3$NH$_2$

78

Using the procedure of example 19, compound 78a (10 mg) was reacted with methylamine (1M in THF, 0.1 mL) to provide 7.1 mg (84%) of compound 78. $^1$H NMR (400 MHz, CD$_3$OD) δ 8.90 (d, 1 H), 8.20 (d, 1 H), 8.15 (s, 1 H), 8.05 (d, 1 H), 7.20 (dd, 1 H), 6.95 (d, 1 H), 3.80 (m, 1 H), 2.70 (t, 2 H), 2.20 (m, 2 H), 1.90 (m, 2 H), 1.50 (m, 2 H), 1.40-1.10 (m, 5 H). MS (ESI) m/z 352 (M+H)$^+$.

EXAMPLE 79

3-Methyl-4-[4-(1H-pyrrolo[2,3-b]pyridin-3-yl)-pyrimidin-2-ylamino]-phenol (79)

Using procedure of example 1, compound 1f (4.0 g) was reacted with 4-amino-3-methylphenol (2.66 g) to provide 1.7 g (50%) of compound 79. $^1$H NMR (400 MHz, DMSO) δ 12.20 (s, 1 H), 9.18 (s, 1 H), 8.45 (s, 1 H), 8.35 (d, 1 H), 8.22 (d, 1 H), 8.18 (d, 1 H), 7.15 (m, 1 H), 7.00 (m, 1 H), 6.65 (d, 1 H), 6.60 (dd, 1 H), 2.15 (s, 3 H). MS (ESI) m/z: 316 (M+H)$^+$.

EXAMPLE 80

[4-(2-Methylamino-ethoxy)-2-methyl-phenyl]-[4-(1H-pyrrolo[2,3-b]pyridin-3-yl)-pyrimidin-2-yl]-amine (80)

Using procedure of example 1, compound 1f (4.0 g) and 4-amino-3-methylphenol (2.66 g) were used to provide 2.2 g (45%) of compound 80a. $^1$H NMR (400 MHz, DMSO) δ 9.23 (s, 1 H), 8.82 (s, 1 H), 8.68 (s, 1 H), 8.35 (dd, 1 H), 8.15 (d, 1 H), 7.75 (t, 1 H), 7.55 (t, 1 H), 7.40 (d, 1 H), 7.15 (br s, 1 H), 7.10 (d, 1 H), 6.65 (d, 1 H), 6.60 (dd, 1 H), 2.05 (s, 3 H).

MS (ESI) m/z: 458 (M+H)$^+$.

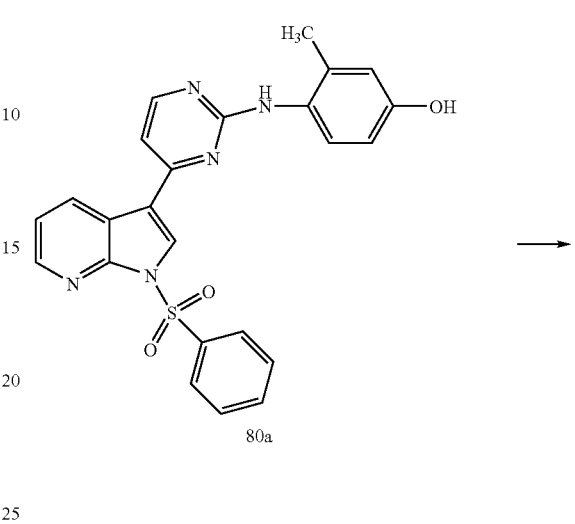

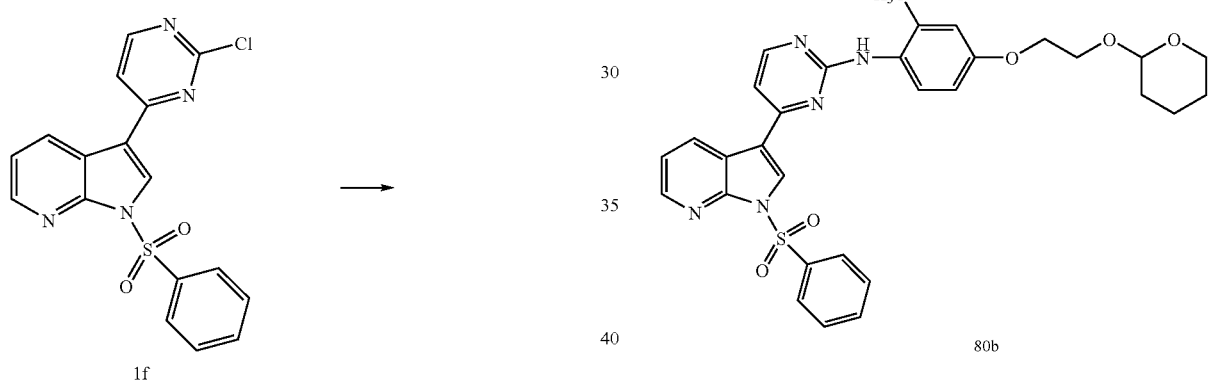

To a flask was added compound 80a (1.0 g), 2-(2-bromoethoxy)tetrahydropyran (0.55 g), K$_2$CO$_3$ (0.6 g) and DMF (10 mL). The mixture was heated to 70° C. for 3 hrs, then poured into water and extracted with EtOAc. The organic layer was separated, dried with MgSO$_4$, then concentrated and the residue was purified by flash chromatography [silica gel, EtOAc] to afford 1.1 g (88%) of compound 80b. MS (ESI) m/z: 585 (M+H)$^+$.

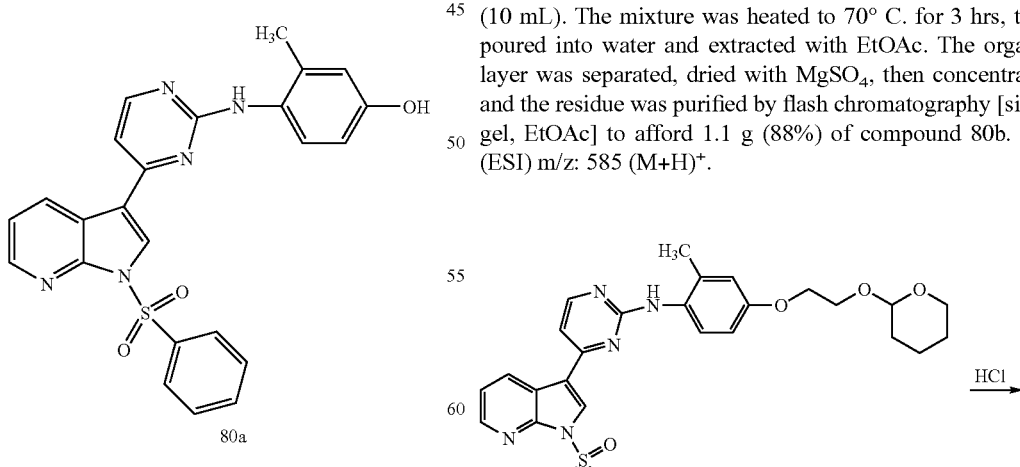

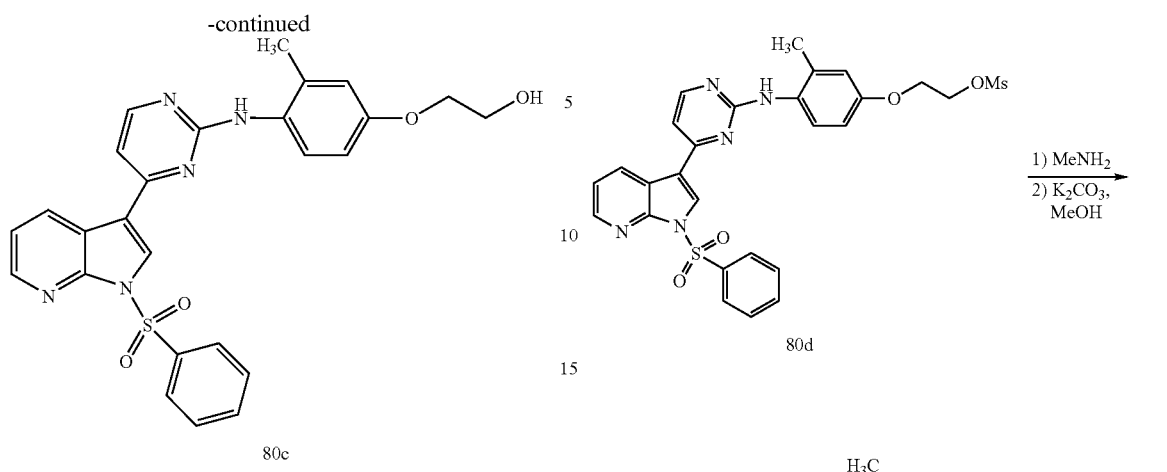

Compound 80b (200 mg) was treated with HCl in MeOH to provide compound 80c. MS (ESI) m/z: 502 (M+H)$^+$.

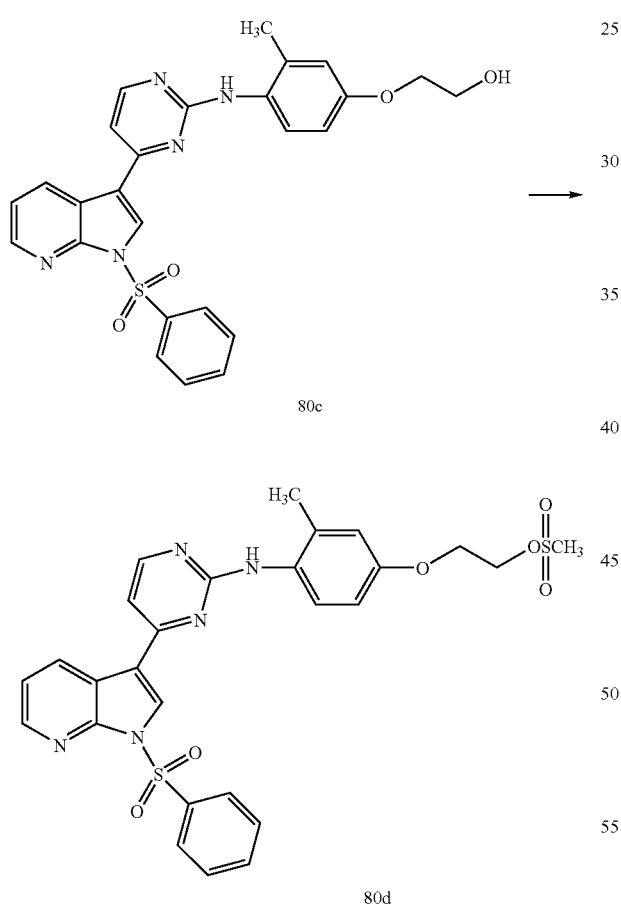

Using the procedure of example 19, compound 80c (0.9 g) was reacted with methanesulfonyl chloride (0.14 mL) to provide 0.96 g (92%) of compound 80d. $^1$H NMR (300 MHz, CDCl$_3$) δ 8.55 (d, 1 H), 8.35 (t, 2 H), 8.02 (m, 2 H), 7.90 (d, 2 H), 7.65 (t, 1 H), 7.50 (t, 2 H), 7.28 (s, 1 H), 7.20 (dd, 1 H), 7.05 (d, 1 H), 6.95 (s, 1 H), 6.85 (dd, 1 H), 6.80 (s, 1 H), 2.85 (s, 3 H), 2.30 (s, 3 H). MS (ESI) m/z: 580 (M+H)$^+$.

Using the procedure of example 19, compound 80d was reacted with methylamine to displace the mesyl group by methylamino group. The phenylsulfonyl protecting group was removed by heating with K$_2$CO$_3$ in MeOH to provide compound 80. $^1$H NMR (300 MHz, CD$_3$OD) δ 8.45 (d, 1 H), 8.25 (m, 1 H), 8.20 (s, 1 H), 8.12 (d, 1 H), 7.20 (d, 1 H), 7.05 (m, 1 H), 6.75 (d, 1 H), 6.70 (dd, 1 H), 4.50 (t, 2 H), 3.05 (t, 2 H), 2.45 (s, 3 H), 2.20 (s, 3 H).

MS (ESI) m/I: 375 (M+H)$^+$.

EXAMPLE 81

[4-(2-Dimethylamino-ethoxy)-2-methyl-phenyl]-[4-(1H-pyrrolo[2,3-b]pyridin-3-yl)-pyrimidin-2-yl]-amine (81)

Using the procedure of example 19, compound 80d was reacted with dimethylamine to displace the mesyl group by dimethylamino group. The phenylsulfonyl protecting group was removed by heating with K$_2$CO$_3$ in MeOH to provide compound 81. $^1$H NMR (400 MHz, CDCl$_3$) δ 8.40 (d, 1 H), 8.20 (d, 1 H), 8.15 (d, 1 H), 7.85 (s, 1 H), 7.35 (d, 1 H), 7.15 (s, 1 H), 7.00 (m, 1 H), 7.85 (d, 1 H), 6.55 (m, 2 H), 4.35 (t, 2 H), 2.75 (t, 2 H), 2.25 (s, 6H), 2.18 (s, 3 H). MS (ESI) m/z: 389 (M+H)$^+$.

BIOLOGICAL EXAMPLES

The utility of the compounds to treat or ameliorate a CDK, VEGF-R2 kinase, HER2 kinase, Aurora-A kinase, or RET receptor kinase mediated disorder was determined using the following procedures.

Selected compounds from the above example were investigated for their kinase activity. A panel of protein kinases, including CDK1, VEGF-R2, Aurora-A, RET and HER2 were used. The individual assays are described as follows:

EXAMPLE 1

CDK1 Screening Assay

A kinase reaction mixture was prepared containing 50 mM Tris-HCl pH=8, 10 mM $MgCl_2$, 0.1 mM $Na_3PO_4$, 1 mM DTT, 10 µM ATP, 0.025 µM biotinylated histone-HI peptide substrate and 0.2, Curies per well $^{33}$P-γ-ATP (2000-3000 Ci/mmol). 70 µL of the kinase reaction mixture was dispensed into the well of a streptavidin coated FlashPlate™ (Cat. # SMP103, NEN, Boston, Mass.). Then 1 µL of test compound stock in 100% DMSO was added to the wells resulting in a final concentration of 1% DMSO in the reaction with a 100 µL final reaction volume.

The CDK1:Cyclin-B protein was then diluted in 50 mM Tris-HCl pH=8.0, 0.1% BSA at a concentration of 1 ng per µL and 30 µL (30 ng enzyme per test well) was added to each well to initiate the reaction. The reaction was incubated for one hour at 30° C. At the end of the 1 h incubation, the reaction was terminated by aspirating the mixture from the plate and washing the wells twice with PBS containing 100 mM EDTA. The histone-H1 biotinylated peptide substrate became immobilized on the Flashplate™ and the incorporation of $^{33}$P-γ-ATP was measured by reading the plate on a scintillation counter. Inhibition of the enzymatic activity of CDK1 was measured by observing a reduced amount of $^{33}$P-γ-ATP incorporated into the immobilized peptide.

The CDK1 used was isolated from insect cells expressing both the human CDK1 catalytic subunit and its positive regulatory subunit cyclin B (New England Biolabs, Beverly, Mass., Cat. #6020).

EXAMPLE 2

VEGF-R2 Screening Assay

The VEGF-R kinase assay was carried out using the CDK kinase assay procedure except that the enzyme was replaced with the VEGF-R2 fusion protein containing a polyhistidine tag at the N-terminus followed by amino acids 786-1343 of the rat VEGF-R2 kinase domain (GenBank Accession #U93306).

EXAMPLE 3

Aurora-A Screening Assay

The Aurora-A kinase assay was carried out using the CDK kinase assay procedure except that the enzyme was replaced with the full length protein encoding the murine Aurora-A (Accession# GB BC014711) expressed and purified from sf9 insect cells.

EXAMPLE 4

HER2 kinase Screening Assay

The HER2 kinase assay was carried out using the CDK kinase assay procedure except that the enzyme was replaced with a HER2 construct containing a polyhistidine tag at the N-terminus followed by 24 additional amino acids and the HER2 cytoplasmic domain beginning at amino acid 676 (Accession #M11730) to the end.

EXAMPLE 5

RET Kinase Screening Assay

The RET kinase assay was carried out using the CDK kinase assay procedure except that the enzyme was replaced with a construct encoding the RET cytoplasmic domain consisting of the last 492 amino acids of the intracellular domain of the RET tyrosine kinase (accession #X12949) containing an N-terminal histidine tag was expressed and purified from Hi5 insect cells.

Peptide Substrates

VEGF-R2, HER2 and (Biotin)KHKKLAEGSAYEEV-Amide

RET kinases

CDK1 (Biotin)KTPKKAKKPKTPKKAKKL-Amide

Aurora-A kinase Biotin-GRTGRRNSI-Amide

Results of assays performed on compounds described above are provided below in Table 1. An $IC_{50}$ listed as >0.1, >1, or >10 means no observed 50% inhibition at the highest test concentration. An $IC_{50}$ listed as ~1 or ~10 means approximately 50% inhibition was observed at the highest test concentration. ND means the compound was not tested in the assay specified.

TABLE 1

| Cpd | $IC_{50}$(µM) CDK1 | $IC_{50}$(µM) VEGF-R2 | $IC_{50}$(µM) HER2 | $IC_{50}$(µM) Aurora-A | $IC_{50}$(µM) Ret |
|---|---|---|---|---|---|
| 1 | 0.019 | 0.087 | 0.008 | 0.159 | 0.337 |
| 2 | 0.169 | 0.046 | 0.206 | 0.063 | 0.128 |
| 3 | 0.054 | 0.213 | 0.032 | 0.159 | 1 |
| 4 | 0.021 | 0.01 | 0.01 | 0.173 | 1.415 |
| 5 | 0.011 | 0.238 | ND | 0.134 | 1.142 |
| 6 | 0.119 | 0.14 | ND | 0.1 | ~1 |
| 7 | 0.044 | 0.820 | ND | 0.497 | >10 |
| 8 | 0.0037 | 0.5699 | ND | 0.3011 | ~10 |
| 9 | 0.057 | 0.0967 | ND | 0.136 | ~1 |
| 10 | 0.04 | 0.2001 | ND | 0.2895 | ~10 |
| 11 | 0.0696 | ~1 | ND | ~1 | >10 |
| 12 | 0.0092 | 0.8783 | ND | 0.287 | >10 |
| 13 | 0.014 | 2.078 | 0.003 | 0.263 | >10 |
| 14 | 0.088 | 2.231 | 100 | 0.885 | 10 |
| 15 | 0.012 | 2.112 | 100 | 0.166 | 100 |
| 16 | 0.151 | 10 | 100 | 0.6357 | 100 |
| 17 | 0.012 | 3.811 | 100 | 0.312 | 100 |
| 18 | 0.0076 | 1.787 | 100 | 0.335 | 11.21 |
| 19 | 0.032 | 0.065 | 0.011 | 0.162 | 0.692 |
| 20 | 0.134 | 0.186 | 0.025 | 0.253 | 0.892 |
| 21 | 0.068 | 0.075 | 0.009 | 0.197 | 0.753 |
| 22 | 0.074 | 0.084 | 0.011 | 0.173 | 0.587 |
| 23 | 0.039 | 0.066 | 0.012 | 0.257 | 0.537 |
| 24 | 0.028 | 0.089 | 0.009 | 0.244 | 0.504 |
| 25 | 0.051 | 0.093 | 0.012 | 0.182 | 1.262 |
| 26 | 0.014 | 0.094 | 0.006 | 0.157 | 0.484 |
| 27 | 0.002 | 1 | ND | 0.357 | 100 |
| 28 | 0.0127 | 1 | ND | 0.175 | 100 |
| 29 | 0.056 | 1.966 | ND | 1 | 10 |
| 30 | 0.139 | 0.049 | ND | 0.289 | 1 |
| 31 | 0.046 | 1 | ND | 0.1 | 100 |
| 32 | 0.068 | 1.475 | ND | 0.396 | 10 |
| 33 | 0.001 | 1.141 | ND | 0.408 | 10 |
| 34 | 0.004 | 0.618 | ND | 0.238 | 100 |
| 35 | 0.017 | 0.975 | ND | 0.556 | 1 |

TABLE 1-continued

| Cpd | IC$_{50}$(μM) CDK1 | IC$_{50}$(μM) VEGF-R2 | IC$_{50}$(μM) HER2 | IC$_{50}$(μM) Aurora-A | IC$_{50}$(μM) Ret |
|---|---|---|---|---|---|
| 36 | 0.0223 | 100 | ND | 1 | 100 |
| 37 | 0.035 | 0.211 | ND | 0.386 | 1.62 |
| 38 | 0.0096 | 0.081 | ND | 0.112 | 0.821 |
| 39 | 0.168 | 1.655 | ND | 0.735 | 100 |
| 40 | 0.010 | 0.149 | ND | 0.084 | 1 |
| 41 | 0.0063 | 1.642 | 100 | 0.1816 | 100 |
| 42 | 0.002 | 7.879 | ND | 0.917 | 10 |
| 43 | 0.0066 | 2.777 | ND | 0.262 | 3.721 |
| 44 | 0.0006 | 0.4934 | ND | 0.1423 | 1.619 |
| 45 | 0.00095 | 0.5826 | ND | 0.3165 | 1.54 |
| 46 | 0.0016 | 0.3413 | ND | 0.4656 | 1.117 |
| 47 | 0.0014 | 0.8816 | ND | 0.972 | 1.399 |
| 48 | 0.0006 | 0.8754 | ND | 0.8598 | 3.52 |
| 49 | 0.00196 | 0.7503 | ND | 0.3333 | 2.278 |
| 50 | 0.0011 | 0.9588 | ND | 0.9024 | 3.07 |
| 51 | 0.0026 | 1.253 | ND | 0.8951 | 2.67 |
| 52 | 0.0087 | 0.3224 | ND | 0.07566 | 0.5402 |
| 53 | 0.0441 | 1.308 | ND | 0.4075 | 2.361 |
| 54 | 0.06122 | 2.313 | ND | 0.9083 | 4.059 |
| 55 | 0.04084 | 0.3419 | ND | 0.7854 | 1.147 |
| 56 | 0.1048 | 1.036 | ND | 0.8595 | 1.235 |
| 57 | 0.2833 | 10 | ND | 3.976 | 100 |
| 58 | 0.109 | 1.541 | ND | 0.5662 | 100 |
| 59 | 0.062 | 0.55 | ND | 0.4374 | 55 |
| 60 | 0.03727 | 2.463 | ND | 1.513 | 10 |
| 61 | 0.1285 | 10 | ND | 2.253 | 100 |
| 62 | 0.5002 | 2.673 | ND | 0.7616 | 10 |
| 63 | 2.115 | 10 | ND | 4.193 | 100 |
| 64 | 0.04984 | 10 | ND | 1.685 | 100 |
| 65 | 0.06029 | 1.068 | ND | 1.302 | 1.232 |
| 66 | 10 | 100 | ND | 100 | 100 |
| 67 | 0.1275 | 1 | ND | 2.363 | 100 |
| 68 | 0.0308 | 1 | ND | 0.3201 | 100 |
| 69 | 10.44 | 100 | ND | 100 | 100 |
| 70 | 3.211 | 100 | ND | 10 | 100 |
| 71 | 1.65 | 100 | ND | 10 | 100 |
| 72 | 0.6001 | 10 | 100 | 6.064 | 100 |
| 73 | 7.021 | 100 | 100 | 100 | 100 |
| 74 | 3.889 | 100 | 10 | 100 | 100 |
| 75 | 2.02 | 100 | ND | 10 | 100 |
| 76 | 1.352 | 10 | 100 | 100 | 100 |
| 77 | 0.0028 | 3.572 | ND | 0.3738 | 10 |
| 78 | 0.00426 | 6.708 | ND | 1.007 | 10 |
| 79 | 0.000764 | 0.927 | ND | 0.119 | 4.816 |
| 80 | 2.314 | 10 | ND | 10 | 10 |
| 81 | 1.869 | 100 | ND | 10 | 100 |

Assay to Measure Inhibition of Cell Proliferation

The ability of a test compound to inhibit the proliferation of cell growth was determined by measuring incorporation of $^{14}$C-labelled thymidine into newly synthesized DNA within the cells. This method was used on cell lines derived from carcinomas originating from several tissues such as HeLa cervical adenocarcinoma (American Type Culture Collection (ATCC), Virginia, Cat. #CCL-2), A375 malignant melanoma (ATCC CRL-1619), HCT-116 colon carcinoma (CCL-247). In this way the effect of a compound on cell growth of cells with many different phenotypes can be determined. Cells were trypsinized and counted and 3000-8000 cells were added to each well of a 96-well CytoStar tissue culture treated scintillating microplate (Amersham #RPNQ0160) in complete medium in a volume of 100 μL. Cells were incubated for 24 hours in complete medium at 37° C. in an atmosphere containing 5% $CO_2$.

Next, 1 μL of test compound in 100% DMSO was added to the wells of the plate. DMSO only was added to control wells. Cells were incubated for 24 more hours in complete medium at 37° C. in an atmosphere containing 5% $CO_2$. Methyl $^{14}$C-thymidine 56 mCi/mmol (NEN #NEC568 or Amersham #CFA532) was diluted in complete medium and 0.2 uCi/well was added to each well of the CytoStar plate in a volume of 20 μl. The plate was incubated for 24 hours at 37° C. plus 5% $CO_2$ in drug plus $^{14}$C-thymidine. The contents of the plate discarded into a $^{14}$C radioactive waste container by inverting the plate and the plate was washed twice with 200 μL PBS.

200 μL of PBS is added to each well. The top of the plate was sealed with a transparent plate sealer and a white plate backing sealer (Packard #6005199) was applied to the bottom of the plate. The degree of methyl $^{14}$C-thymidine incorporation was quantified on a Packard Top Count.

Antiproliferative effects of the compounds described above are provided below in Table 2

TABLE 2

| Cpd | IC$_{50}$(μM) HeLa | IC$_{50}$(μM) HCT116 | IC$_{50}$(μM) A375 |
|---|---|---|---|
| 1 | 0.056 | 0.022 | 0.066 |
| 2 | 0.33 | 0.56 | 0.75 |
| 3 | 0.3819 | 0.2598 | 0.4681 |
| 4 | 0.062 | 0.062 | 0.061 |
| 5 | 0.059 | 0.034 | 0.05 |
| 6 | 1.46 | 0.72 | 0.95 |
| 7 | 0.35 | 0.29 | 0.35 |
| 8 | 0.028 | 0.024 | 0.024 |
| 9 | 0.29 | 0.25 | 0.34 |
| 10 | 0.22 | 0.23 | 0.25 |
| 11 | 1.01 | 0.56 | 0.97 |
| 12 | 0.14 | 0.16 | 0.1 |
| 13 | 0.031 | 0.032 | 0.033 |
| 14 | 0.059 | 0.078 | 0.093 |
| 15 | 0.0082 | 0.007556 | 0.004668 |
| 16 | 0.3683 | 0.4096 | 0.6035 |
| 17 | 0.02425 | 0.02075 | 0.01402 |
| 18 | 0.001607 | 0.002249 | 0.001774 |
| 19 | 0.029 | 0.013 | 0.021 |
| 20 | 0.14 | 0.037 | 0.11 |
| 21 | 0.03148 | 0.01591 | 0.02953 |
| 22 | 0.035 | 0.018 | 0.055 |
| 23 | 0.03 | 0.025 | 0.024 |
| 24 | 0.034 | 0.018 | 0.031 |
| 25 | 0.062 | 0.068 | 0.04 |
| 26 | 0.026 | 0.01346 | 0.02219 |
| 27 | 0.007196 | 0.006394 | 0.004496 |
| 28 | 0.09516 | 0.1176 | 0.06756 |
| 29 | 0.3919 | 0.3807 | 0.4027 |
| 30 | 0.9558 | 0.6521 | 1.646 |
| 31 | 0.0992 | 0.1052 | 0.1104 |
| 32 | 0.2921 | 0.2539 | 0.2171 |
| 33 | 0.000993 | 0.000542 | 0.0000467 |
| 34 | 0.01135 | 0.00137 | 0.01571 |
| 35 | 0.09033 | 0.03305 | 0.03691 |
| 36 | 0.4666 | 0.2772 | 0.4482 |
| 37 | 0.194 | 0.08281 | 0.1846 |
| 38 | 0.03583 | 0.02158 | 0.04944 |
| 39 | 0.3838 | 0.2419 | 0.8623 |
| 40 | 0.06616 | 0.02444 | 0.05651 |
| 41 | 0.01014 | 0.01321 | 0.04196 |
| 42 | 0.001124 | 0.000353 | 0.000743 |
| 43 | 0.002923 | 0.002967 | 0.002421 |
| 44 | 0.01098 | 0.003983 | 0.008446 |
| 45 | 0.003367 | 0.002196 | 0.001674 |
| 46 | 0.000963 | 0.000545 | 0.000634 |
| 47 | 0.003023 | 0.002924 | 0.002878 |
| 48 | 0.002547 | 0.003015 | 0.00255 |
| 49 | 0.002517 | 0.002939 | 0.002823 |
| 50 | 0.002683 | 0.002834 | 0.002844 |
| 51 | 0.004662 | 0.003612 | 0.003519 |
| 52 | 0.1621 | 0.121 | 0.1338 |
| 53 | 0.1235 | 0.1267 | 0.09127 |
| 54 | 0.2808 | 0.2688 | 0.2148 |
| 55 | 0.292 | 0.2637 | 0.2329 |

TABLE 2-continued

| Cpd | IC$_{50}$(μM) HeLa | IC$_{50}$(μM) HCT116 | IC$_{50}$(μM) A375 |
|---|---|---|---|
| 56 | 1.1 | 0.7737 | 0.7274 |
| 57 | 0.1345 | 0.07324 | 0.09727 |
| 58 | 0.5139 | 0.222 | 0.2766 |
| 59 | 0.2914 | 0.3786 | 0.2507 |
| 60 | 0.04105 | 0.01752 | 0.04174 |
| 61 | 0.02601 | 0.01526 | 0.02144 |
| 62 | 1.084 | 0.5246 | 0.6216 |
| 63 | 34.72 | 40.01 | 16.38 |
| 64 | 0.1356 | 0.06893 | 0.1551 |
| 65 | 0.02689 | 0.01504 | 0.02181 |
| 66 | 52.17 | 10 | 10 |
| 67 | 0.393 | 0.2982 | 0.5042 |
| 68 | 0.02303 | 0.01295 | 0.03173 |
| 69 | 8.896 | 13.42 | 7.687 |
| 70 | 6.29 | 3.974 | 5.931 |
| 71 | 9.509 | 4.457 | 7.154 |
| 72 | 0.1438 | 0.07698 | 0.1647 |
| 73 | 4.157 | 3.509 | 3.948 |
| 74 | 4.525 | 3.762 | 3.02 |
| 75 | 1.99 | 1.585 | 2.811 |
| 76 | 0.2104 | 0.1574 | 0.2977 |
| 77 | 0.005976 | 0.00762 | 0.006157 |
| 78 | 0.003738 | 0.003128 | 0.002252 |
| 79 | 0.005902 | 0.004915 | 0.008583 |
| 80 | 2.579 | 3.865 | 4.541 |
| 81 | 13.18 | 4.541 | 2.811 |

In Vivo Models—Inhibition of Tumor Growth

The in vivo effect of a compound on the growth of human tumor cells can be evaluated by implanting human tumor cells into the hindflank of athymic mice and administering test compound to the mice. Human tumor cells originating from a variety of different tumor types, such as A375 human melanoma cells, are implanted subcutaneously into the hindflank of male athymic mice (Charles River) and allowed to establish a sizeable tumor for 6-10 days as determined by caliper measurements. Test compound is then administered by injecting the compound formulated in an appropriate vehicle intraperitoneally into the mice once a day for 30 days. The test compound can also be administered by other routes such as orally, subcutaneously or by intravenous infusion. The size of the tumor in this study is measured every four days and the degree of inhibition is determined by comparing drug-treated animals to animals that are injected with vehicle only.

The synergistic action or enhancement of conventional chemotherapeutic agent by a test compound can also be determined with this model by comparing animals treated with the standard therapy alone to animals treated with test compound plus the same standard therapy. An additive effect on the delay of tumor growth will be observed if synergistic action due to test compound is occurring.

While the foregoing specification teaches the principles of the present invention, with examples provided for the purpose of illustration, it will be understood that the practice of the invention encompasses all of the usual variations, adaptations and modifications as come within the scope of the following claims and their equivalents.

What is claimed is:
1. A compound selected from the group consisting of:

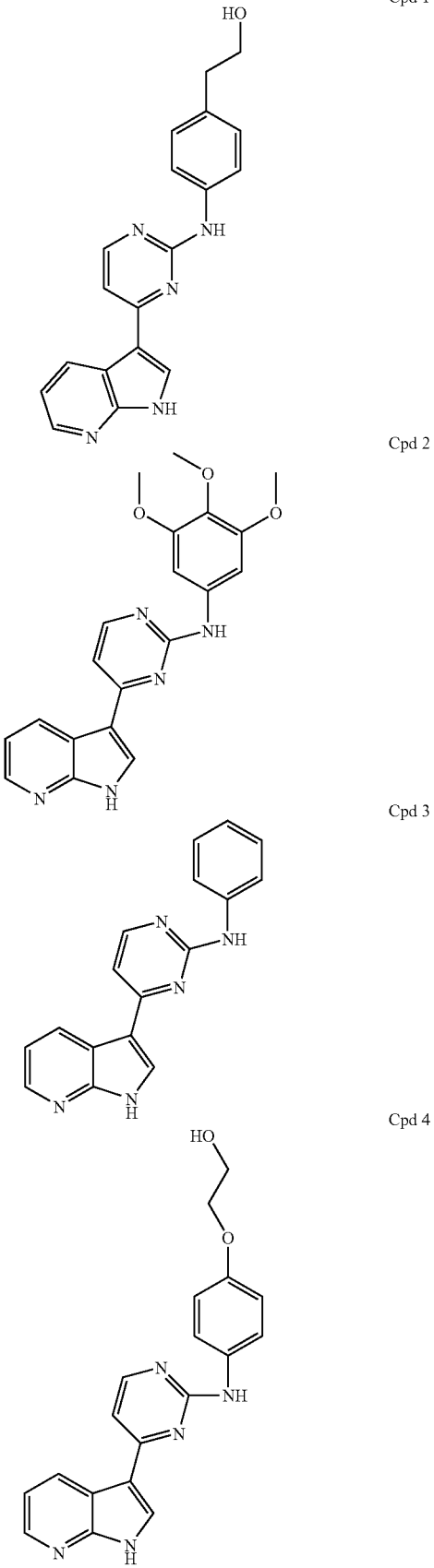

-continued
Cpd 5
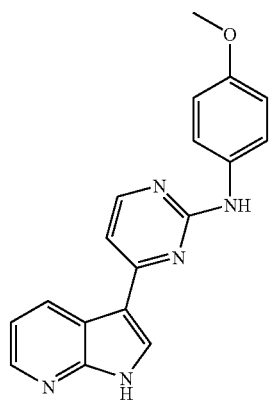
Cpd 6
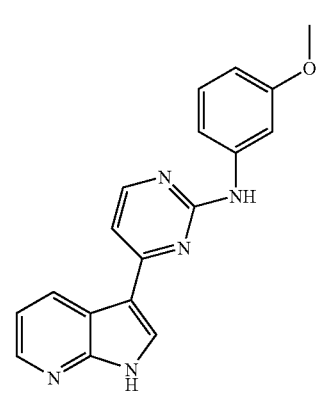
Cpd 7
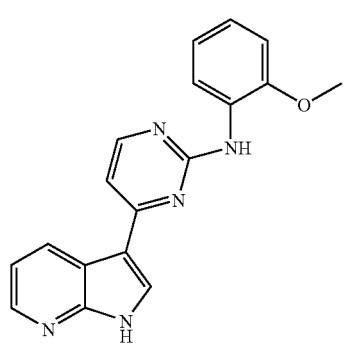
Cpd 8
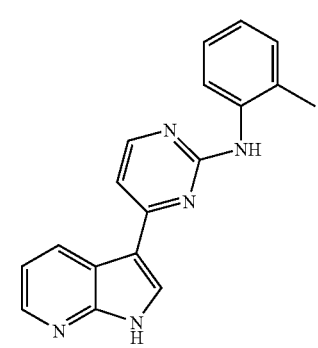
-continued
Cpd 9
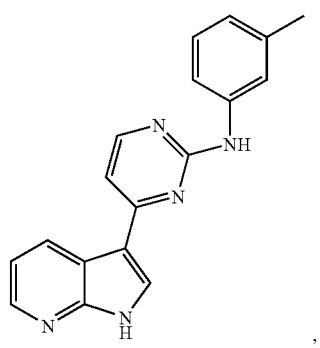
Cpd 10
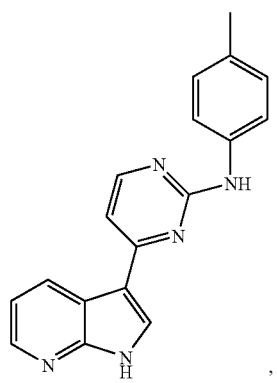
,
Cpd 11
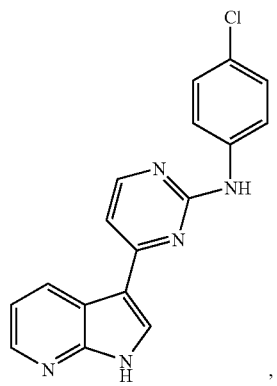
,
Cpd 12
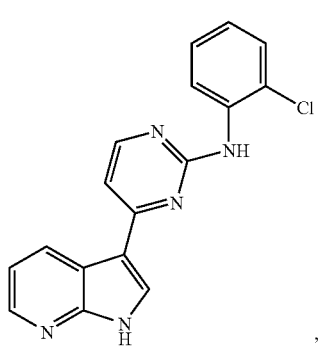
, -continued
Cpd 13
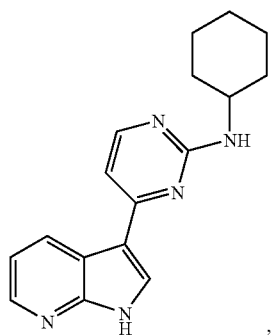
Cpd 14
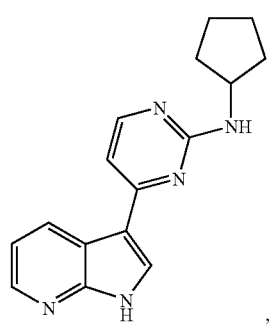
Cpd 15
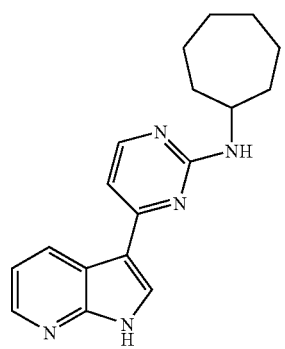
Cpd 17
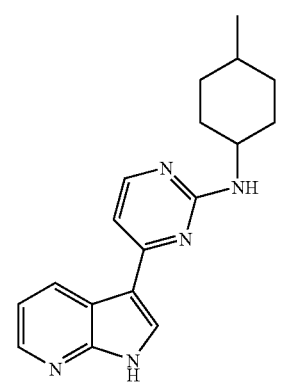
-continued
Cpd 18
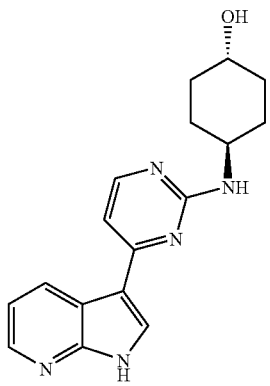
Cpd 19
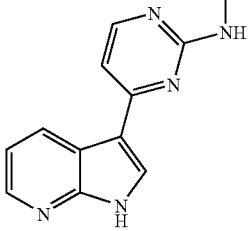
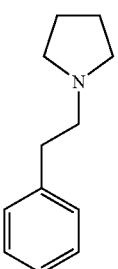
Cpd 20
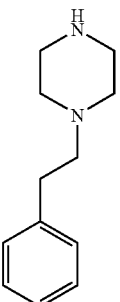

-continued
Cpd 21
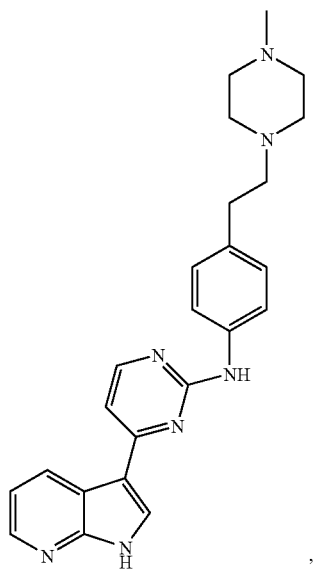
Cpd 22
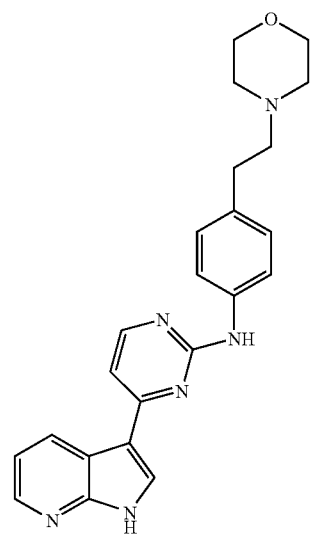
Cpd 23
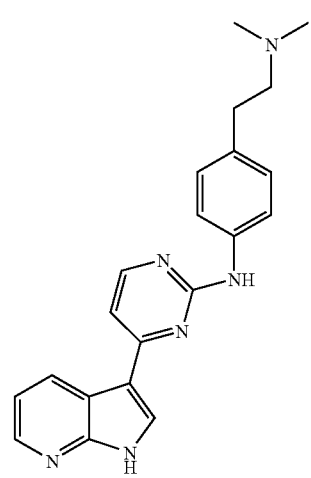
-continued
Cpd 24
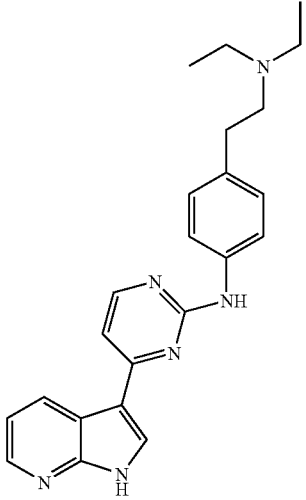
Cpd 25
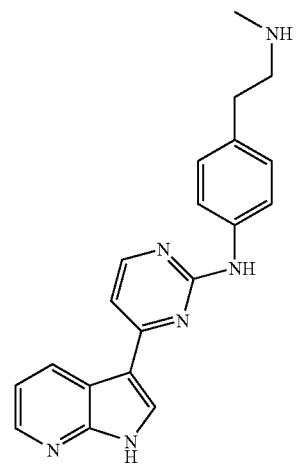
Cpd 26

-continued
Cpd 27
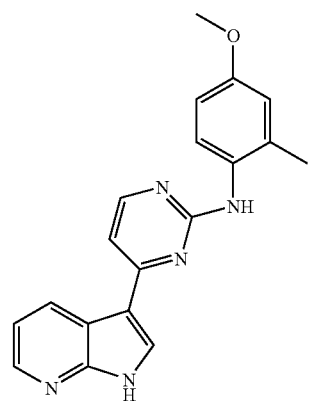
Cpd 28
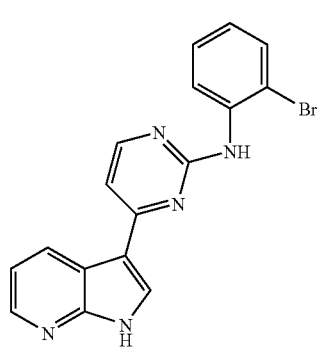
Cpd 29
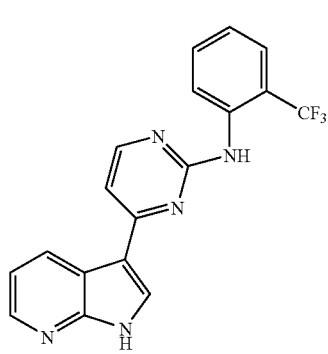
Cpd 30
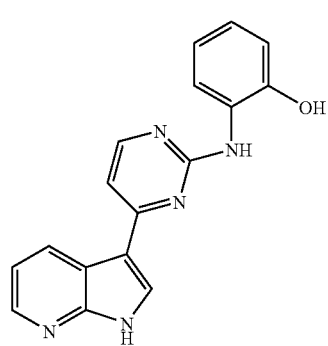
-continued
Cpd 31
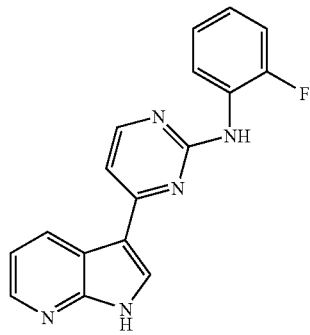
Cpd 32
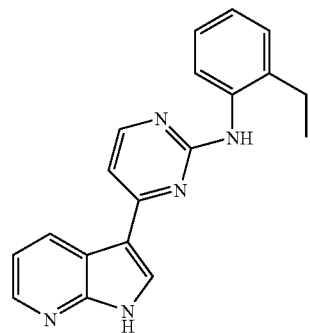
Cpd 33
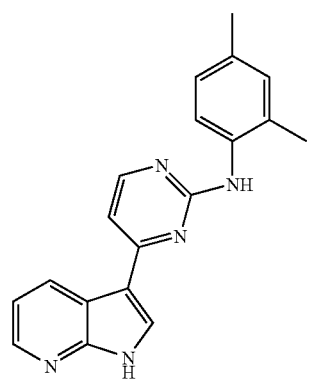
Cpd 34
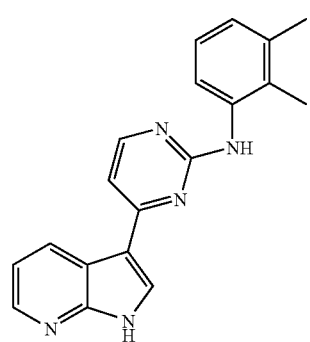

-continued
Cpd 35
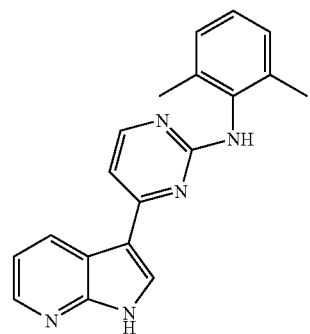
Cpd 36
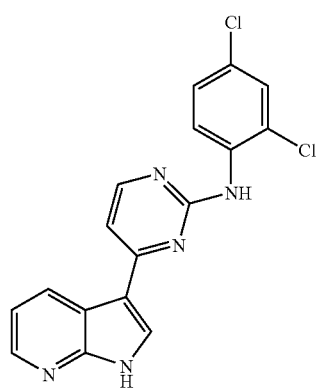
Cpd 37
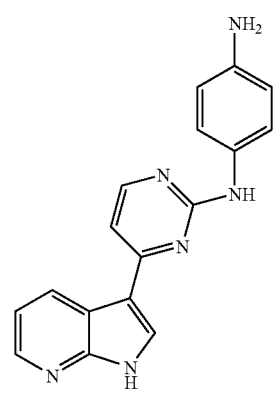
Cpd 38
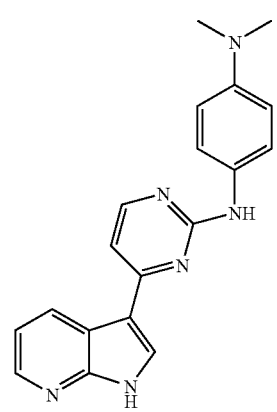
-continued
Cpd 39
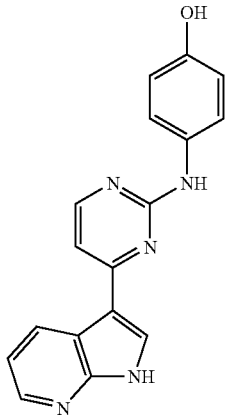
Cpd 40
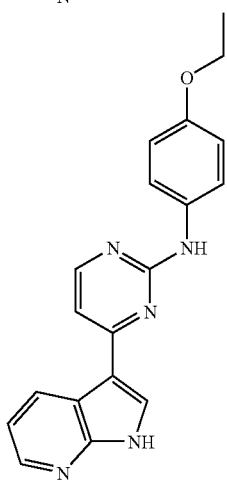
Cpd 41
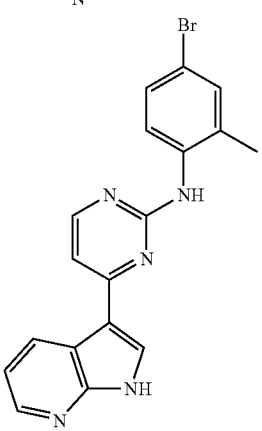
Cpd 42
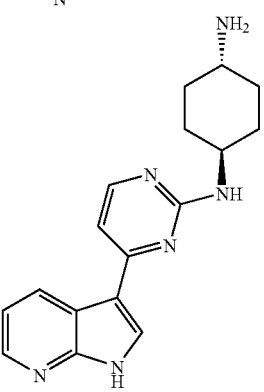

-continued
Cpd 43
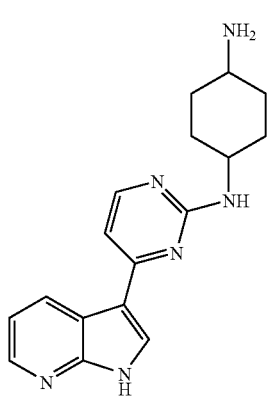
Cpd 44
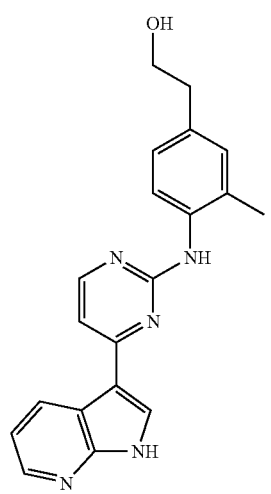
Cpd 45
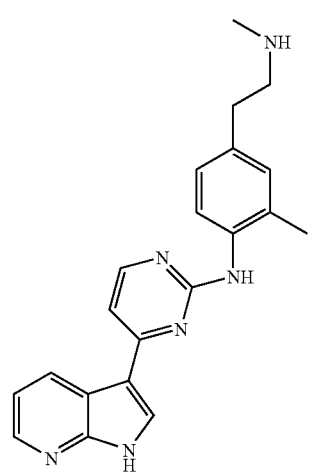
-continued
Cpd 46
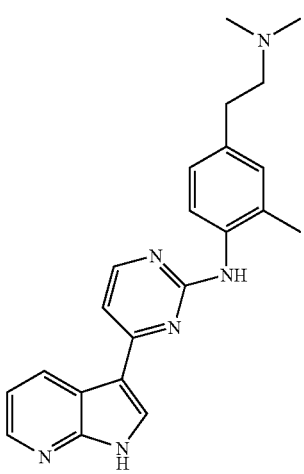
Cpd 47
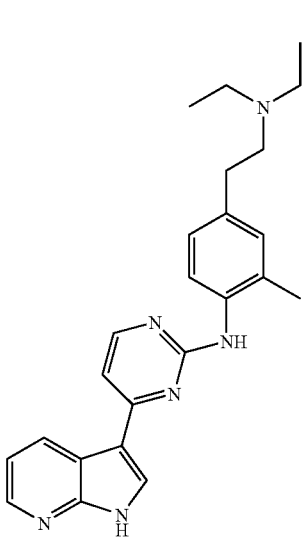
Cpd 48
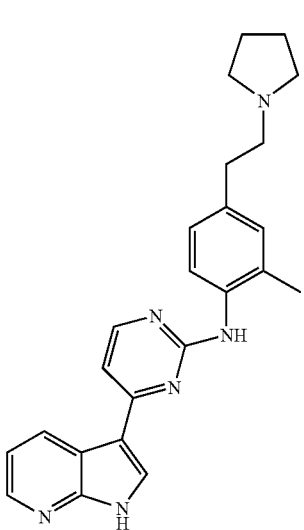

-continued
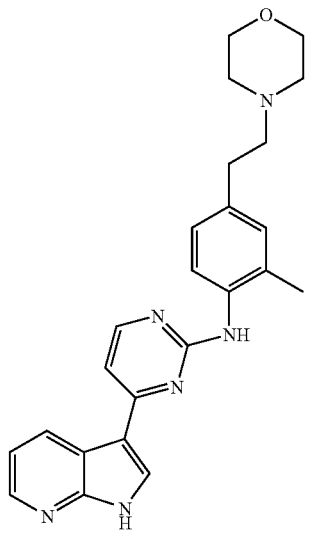
Cpd 49
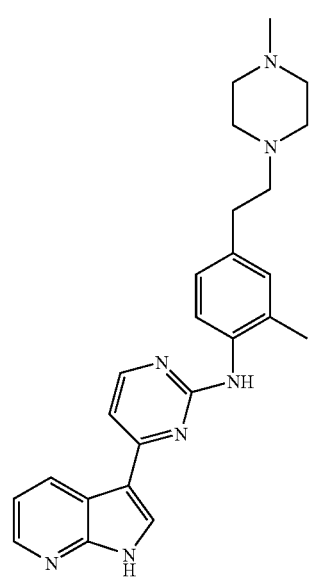
Cpd 50
Cpd 51
-continued
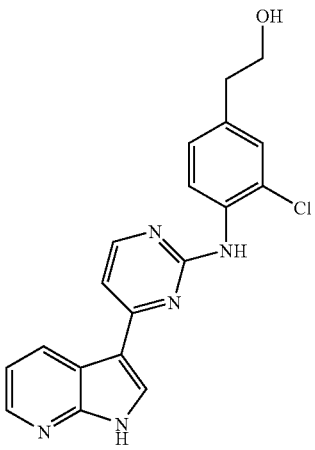
Cpd 52
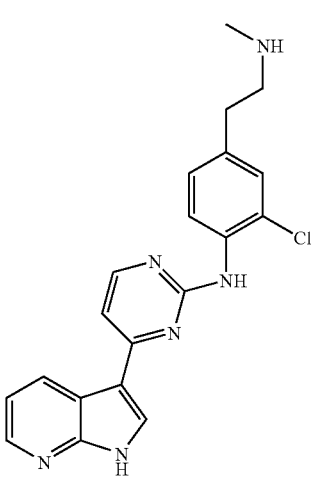
Cpd 53
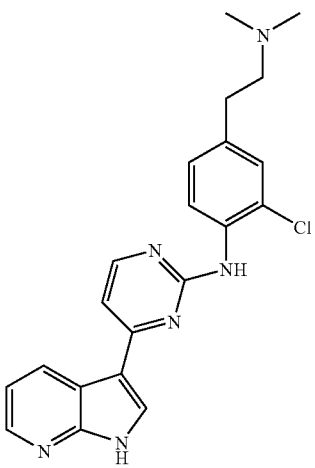
Cpd 54

-continued
Cpd 55
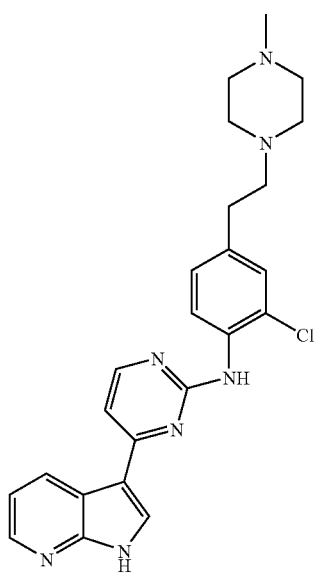
Cpd 56
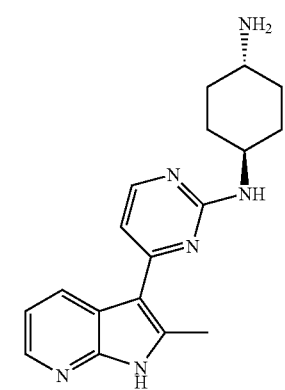
Cpd 57
-continued
Cpd 58
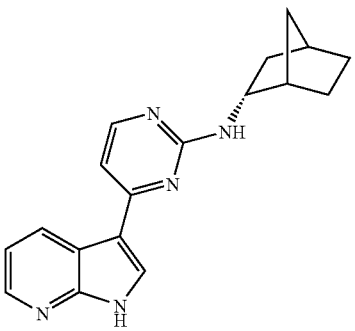
Cpd 59
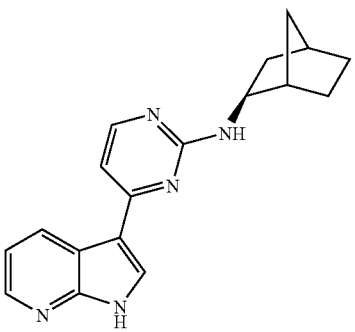
Cpd 60
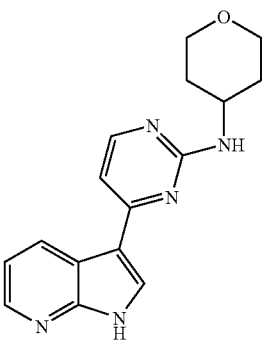
Cpd 61

Cpd 62
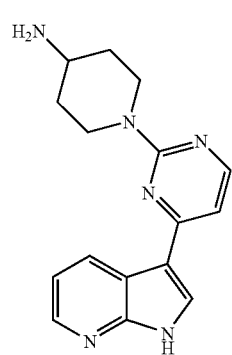
Cpd 63
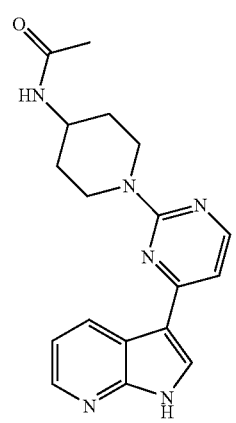
Cpd 64
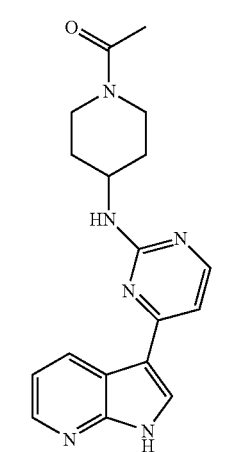
Cpd 65
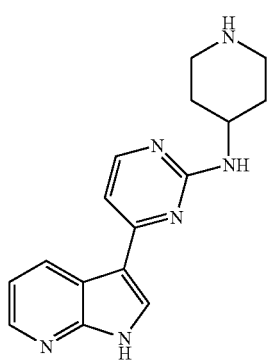
Cpd 66
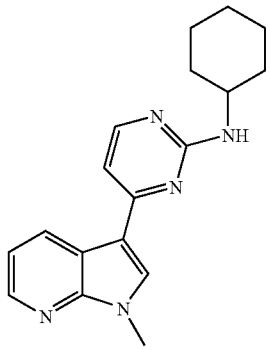
Cpd 67
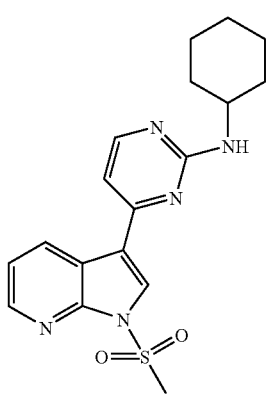
Cpd 68
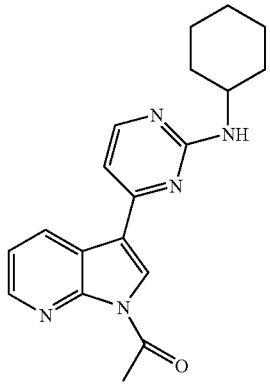
Cpd 69
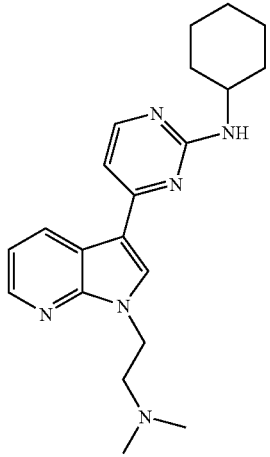

-continued
Cpd 70
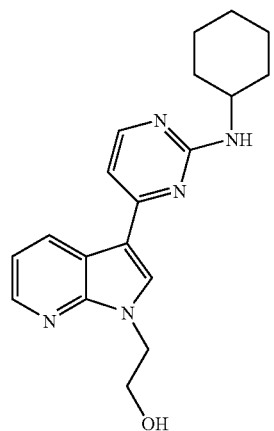
Cpd 71
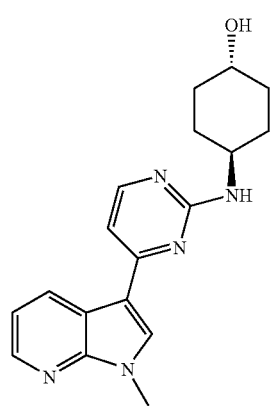
Cpd 72
-continued
Cpd 73
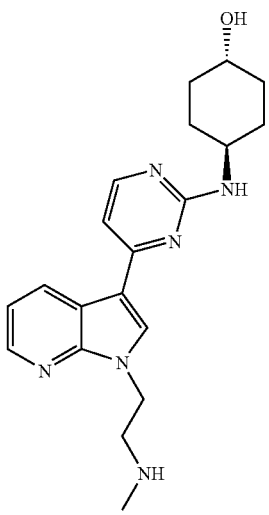
Cpd 74
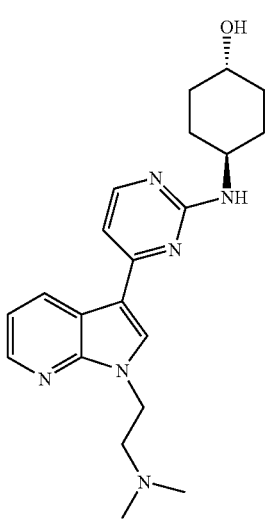
Cpd 75
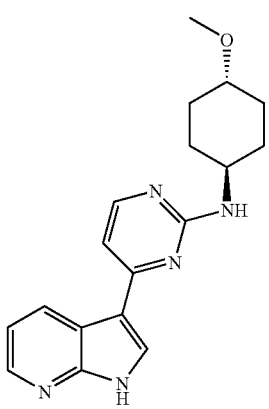

-continued
Cpd 76
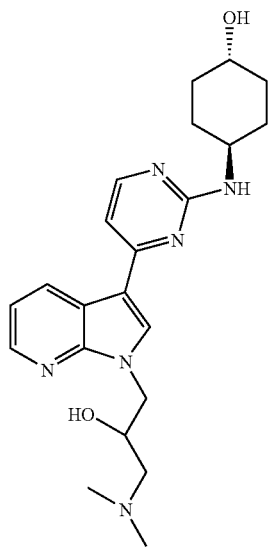
Cpd 77
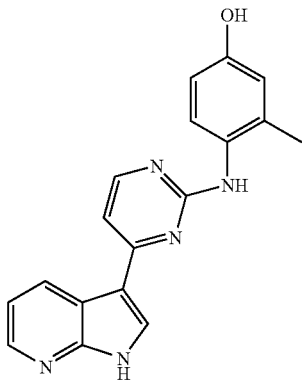
Cpd 78
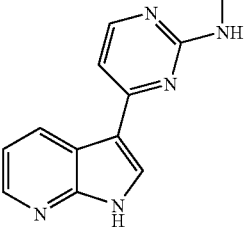
-continued
Cpd 79
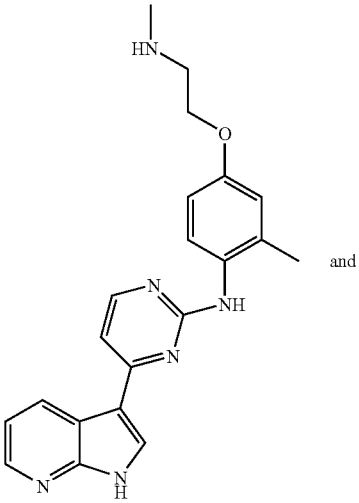
Cpd 80
and
Cpd 81
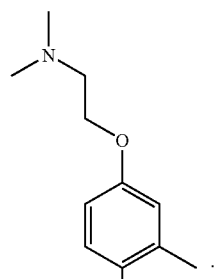
2. The compound of claim 1, wherein said compound is Cpd 1.
3. The compound of claim 1, wherein said compound is Cpd 2.
4. The compound of claim 1, wherein said compound is Cpd 3.
5. The compound of claim 1, wherein said compound is Cpd 4.

6. The compound of claim 1, wherein said compound is Cpd 5.

7. The compound of claim 1, wherein said compound is Cpd 6.

8. The compound of claim 1, wherein said compound is Cpd 7.

9. The compound of claim 1, wherein said compound is Cpd 8.

10. The compound of claim 1, wherein said compound is Cpd 9.

11. The compound of claim 1, wherein said compound is Cpd 10.

12. The compound of claim 1, wherein said compound is Cpd 11.

13. The compound of claim 1, wherein said compound is Cpd 12.

14. The compound of claim 1, wherein said compound is Cpd 13.

15. The compound of claim 1, wherein said compound is Cpd 14.

16. The compound of claim 1, wherein said compound is Cpd 15.

17. The compound of claim 1, wherein said compound is Cpd 17.

18. The compound of claim 1, wherein said compound is Cpd 18.

19. The compound of claim 1, wherein said compound is Cpd 19.

20. The compound of claim 1, wherein said compound is Cpd 20.

21. The compound of claim 1, wherein said compound is Cpd 21.

22. The compound of claim 1, wherein said compound is Cpd 22.

23. The compound of claim 1, wherein said compound is Cpd 23.

24. The compound of claim 1, wherein said compound is Cpd 24.

25. The compound of claim 1, wherein said compound is Cpd 25.

26. The compound of claim 1, wherein said compound is Cpd 26.

27. The compound of claim 1, wherein said compound is Cpd 27.

28. The compound of claim 1, wherein said compound is Cpd 28.

29. The compound of claim 1, wherein said compound is Cpd 29.

30. The compound of claim 1, wherein said compound is Cpd 30.

31. The compound of claim 1, wherein said compound is Cpd 31.

32. The compound of claim 1, wherein said compound is Cpd 32.

33. The compound of claim 1, wherein said compound is Cpd 33.

34. The compound of claim 1, wherein said compound is Cpd 34.

35. The compound of claim 1, wherein said compound is Cpd 35.

36. The compound of claim 1, wherein said compound is Cpd 36.

37. The compound of claim 1, wherein said compound is Cpd 37.

38. The compound of claim 1, wherein said compound is Cpd 38.

39. The compound of claim 1, wherein said compound is Cpd 39.

40. The compound of claim 1, wherein said compound is Cpd 40.

41. The compound of claim 1, wherein said compound is Cpd 41.

42. The compound of claim 1, wherein said compound is Cpd 42.

43. The compound of claim 1, wherein said compound is Cpd 43.

44. The compound of claim 1, wherein said compound is Cpd 44.

45. The compound of claim 1, wherein said compound is Cpd 45.

46. The compound of claim 1, wherein said compound is Cpd 46.

47. The compound of claim 1, wherein said compound is Cpd 47.

48. The compound of claim 1, wherein said compound is Cpd 48.

49. The compound of claim 1, wherein said compound is Cpd 49.

50. The compound of claim 1, wherein said compound is Cpd 50.

51. The compound of claim 1, wherein said compound is Cpd 51.

52. The compound of claim 1, wherein said compound is Cpd 52.

53. The compound of claim 1, wherein said compound is Cpd 53.

54. The compound of claim 1, wherein said compound is Cpd 54.

55. The compound of claim 1, wherein said compound is Cpd 55.

56. The compound of claim 1, wherein said compound is Cpd 56.

57. The compound of claim 1, wherein said compound is Cpd 57.

58. The compound of claim 1, wherein said compound is Cpd 58.

59. The compound of claim 1, wherein said compound is Cpd 59.

60. The compound of claim 1, wherein said compound is Cpd 60.

61. The compound of claim 1, wherein said compound is Cpd 61.

62. The compound of claim 1, wherein said compound is Cpd 62.

63. The compound of claim 1, wherein said compound is Cpd 63.

64. The compound of claim 1, wherein said compound is Cpd 64.

65. The compound of claim 1, wherein said compound is Cpd 65.

66. The compound of claim 1, wherein said compound is Cpd 66.

67. The compound of claim 1, wherein said compound is Cpd 67.

68. The compound of claim 1, wherein said compound is Cpd 68.

69. The compound of claim 1, wherein said compound is Cpd 69.

70. The compound of claim 1, wherein said compound is Cpd 70.

71. The compound of claim 1, wherein said compound is Cpd 71.

72. The compound of claim 1, wherein said compound is Cpd 72.

73. The compound of claim 1, wherein said compound is Cpd 73.

74. The compound of claim 1, wherein said compound is Cpd 74.

75. The compound of claim 1, wherein said compound is Cpd 75.

76. The compound of claim 1, wherein said compound is Cpd 76.

77. The compound of claim 1, wherein said compound is Cpd 77.

78. The compound of claim 1, wherein said compound is Cpd 78.

79. The compound of claim 1, wherein said compound is Cpd 79.

80. The compound of claim 1, wherein said compound is Cpd 80.

81. The compound of claim 1, wherein said compound is Cpd 81.

82. A pharmaceutical composition comprising an effective amount of a compound of claim 1 and a pharmaceutically acceptable carrier.

83. The pharmaceutical composition of claim 82, wherein the effective amount of the compound is in a range of from about 0.001 mg/kg to about 300 mg/kg of body weight per day.

84. A process for preparing a pharmaceutical composition comprising the step of admixing a compound of claim 1 and a pharmaceutically acceptable carrier.

85. A method for treating or ameliorating colorectal cancer, comprising administering to the patient an effective amount of a compound of claim 1.

86. The method of claim 85, wherein the effective amount of the compound is from about 0.001 mg/kg/day to about 300 mg/kg/day.

87. The method of claim 86, wherein the amount of the compound is effective to induce remission of a chronic form of a cancer.

88. The method of claim 86, wherein the amount of the compound is effective at a low dose to inhibit unregulated kinase activity.

* * * * *